US011642077B2

(12) United States Patent
Correa Ramírez et al.

(10) Patent No.: US 11,642,077 B2
(45) Date of Patent: May 9, 2023

(54) SLEEP MONITORING SYSTEM WITH OPTIONAL ALARM FUNCTIONALITY

(71) Applicant: Fitbit, Inc., San Francisco, CA (US)

(72) Inventors: Juan Ignacio Correa Ramírez, Bogotá (CO); Conor Joseph Heneghan, Campbell, CA (US); Lindsey Michelle Sunden, San Francisco, CA (US); Lin Yang, Fremont, CA (US); Lukas Bielskis, San Francisco, CA (US); Thomas Samuel Elliot, San Francisco, CA (US); Benjamin B. Perkins, San Francisco, CA (US); Priya Vijay Sheth, San Francisco, CA (US); Jose Roberto Melgoza, San Francisco, CA (US); Nicholas Adrian Myers, Oakland, CA (US); Chris H. Sarantos, San Francisco, CA (US); Andrew Larsen Axley, Mountain View, CA (US); Jaydip Das, Cupertino, CA (US); Samuel Barry Tellman, San Francisco, CA (US); Man-Chi Liu, San Francisco, CA (US); Jeffrey Andrew Fisher, Mountain View, CA (US)

(73) Assignee: FITBIT, INC., San Francisco, CA (US)

( * ) Notice: Subject to any disclaimer, the term of this patent is extended or adjusted under 35 U.S.C. 154(b) by 1231 days.

(21) Appl. No.: 16/097,174

(22) PCT Filed: Apr. 28, 2017

(86) PCT No.: PCT/US2017/030259
§ 371 (c)(1),
(2) Date: Oct. 26, 2018

(87) PCT Pub. No.: WO2017/190085
PCT Pub. Date: Nov. 2, 2017

(65) Prior Publication Data
US 2020/0178887 A1 Jun. 11, 2020

Related U.S. Application Data

(60) Provisional application No. 62/434,910, filed on Dec. 15, 2016, provisional application No. 62/329,979, filed on Apr. 29, 2016.

(51) Int. Cl.
*A61B 5/00* (2006.01)
*A61B 5/0205* (2006.01)
(Continued)

(52) U.S. Cl.
CPC ........ *A61B 5/4815* (2013.01); *A61B 5/02055* (2013.01); *A61B 5/117* (2013.01);
(Continued)

(58) Field of Classification Search
CPC . A61B 5/4815; A61B 5/02055; A61B 5/1115; A61B 5/117; A61B 5/4809;
(Continued)

(56) References Cited

U.S. PATENT DOCUMENTS 4,836,219 A 6/1989 Hobson et al.
5,724,990 A 3/1998 Ogino
(Continued)

FOREIGN PATENT DOCUMENTS

| CN | 103717125 | 4/2014 |
| CN | 103919536 | 7/2014 |

(Continued)

OTHER PUBLICATIONS

U.S. Office Action, dated Dec. 15, 2016, issued in U.S. Appl. No. 15/171,049.
(Continued)

*Primary Examiner* — Ryan W Sherwin
(74) *Attorney, Agent, or Firm* — Dority & Manning, P.A.

(57) ABSTRACT

Sleep tracking systems and techniques for monitoring two or more co-sleepers in a single bed are disclosed. Such systems and techniques may incorporate sleeper identification, as well as various non-user-specific aspects. Some implementations may incorporate user-specific or user-tailored alarm functionality.

20 Claims, 37 Drawing Sheets

(51) Int. Cl.
| | |
|---|---|
| *A61B 5/11* | (2006.01) |
| *A61B 5/117* | (2016.01) |
| *G04G 13/02* | (2006.01) |
| *G04G 15/00* | (2006.01) |
| *G04G 21/02* | (2010.01) |
| *G04G 99/00* | (2010.01) |
| *A61B 90/00* | (2016.01) |
| *A61B 5/024* | (2006.01) |
| *A61B 5/08* | (2006.01) |
| *A61B 5/113* | (2006.01) |

(52) U.S. Cl.
CPC .......... *A61B 5/1115* (2013.01); *A61B 5/4809* (2013.01); *A61B 5/4812* (2013.01); *A61B 5/6892* (2013.01); *A61B 5/7278* (2013.01); *A61B 5/746* (2013.01); *G04G 13/02* (2013.01); *G04G 15/006* (2013.01); *G04G 21/025* (2013.01); *G04G 99/00* (2013.01); A61B 5/02405 (2013.01); A61B 5/0816 (2013.01); A61B 5/1102 (2013.01); A61B 5/113 (2013.01); A61B 5/7203 (2013.01); A61B 5/7264 (2013.01); A61B 2090/064 (2016.02); A61B 2562/0247 (2013.01); A61B 2562/0252 (2013.01); A61B 2562/0266 (2013.01); A61B 2562/066 (2013.01); A61B 2562/168 (2013.01)

(58) Field of Classification Search
CPC ... A61B 5/4812; A61B 5/6892; A61B 5/7278; A61B 5/746; A61B 5/02405; A61B 5/0816; A61B 5/1102; A61B 5/113; A61B 5/7203; A61B 5/7264; A61B 2090/064; A61B 2562/0247; A61B 2562/0252; A61B 2562/0266; A61B 2562/066; A61B 2562/168; A61B 5/4806; A61B 5/024; A61B 5/1036; A61B 5/7207; A61B 5/74; G04G 13/02; G04G 15/006; G04G 21/025; G04G 99/00; G16H 50/20
See application file for complete search history.

(56) References Cited

U.S. PATENT DOCUMENTS

| | | | |
|---|---|---|---|
| 5,902,250 | A | 5/1999 | Verrier et al. |
| 6,964,641 | B2 | 11/2005 | Cho et al. |
| 7,306,567 | B2 | 12/2007 | Loree, IV |
| 7,578,793 | B2 | 8/2009 | Tadros et al. |
| 7,674,230 | B2 | 3/2010 | Reisfeld |
| 8,002,553 | B2 | 8/2011 | Hatlestad et al. |
| 8,273,035 | B2 | 9/2012 | Russo et al. |
| 8,292,819 | B2 | 10/2012 | Kuo et al. |
| 8,548,770 | B2 | 10/2013 | Yuen et al. |
| 8,606,356 | B2 | 12/2013 | Lee et al. |
| 8,684,900 | B2 | 4/2014 | Tran |
| 8,690,751 | B2 | 4/2014 | Auphan |
| 8,712,723 | B1 | 4/2014 | Kahn et al. |
| 8,764,651 | B2 | 7/2014 | Tran |
| 8,793,522 | B2 | 7/2014 | Rahman et al. |
| 8,812,259 | B2 | 8/2014 | Messenger et al. |
| 8,942,779 | B2 | 1/2015 | Halperin et al. |
| 9,675,281 | B2 | 6/2017 | Arnold et al. |
| 9,808,185 | B2 | 11/2017 | Arnold et al. |
| 9,820,680 | B2 | 11/2017 | Muzet |
| 10,092,219 | B2 | 10/2018 | Arnold et al. |
| 10,311,745 | B2 | 6/2019 | Arnold et al. |
| 10,325,514 | B2 | 6/2019 | Arnold et al. |
| 2004/0087878 | A1 | 5/2004 | Krausman et al. |
| 2005/0043652 | A1 | 2/2005 | Lovett et al. |
| 2005/0113650 | A1 | 5/2005 | Pacione et al. |
| 2005/0190065 | A1 | 9/2005 | Ronnholm |
| 2005/0190068 | A1 | 9/2005 | Gentry et al. |
| 2005/0209511 | A1 | 9/2005 | Heruth et al. |
| 2005/0209512 | A1 | 9/2005 | Heruth et al. |
| 2006/0020177 | A1 | 1/2006 | Seo et al. |
| 2006/0031102 | A1 | 2/2006 | Teller et al. |
| 2006/0224051 | A1 | 10/2006 | Teller et al. |
| 2006/0241359 | A1 | 10/2006 | Nagai et al. |
| 2006/0281978 | A1 | 12/2006 | Crucilla |
| 2007/0161873 | A1 | 7/2007 | Ni et al. |
| 2007/0191742 | A1 | 8/2007 | Park |
| 2007/0208233 | A1 | 9/2007 | Kovacs |
| 2008/0287751 | A1 | 11/2008 | Stivoric et al. |
| 2008/0306351 | A1 | 12/2008 | Izumi |
| 2009/0164219 | A1 | 6/2009 | Yeung et al. |
| 2010/0056907 | A1 | 3/2010 | Rappaport et al. |
| 2010/0099954 | A1 | 4/2010 | Dickinson et al. |
| 2010/0102130 | A1 | 4/2010 | Madej et al. |
| 2010/0125215 | A1 | 5/2010 | Kuo et al. |
| 2010/0295684 | A1 | 11/2010 | Hsieh et al. |
| 2011/0015495 | A1 | 1/2011 | Dothie et al. |
| 2011/0230790 | A1 | 9/2011 | Kozlov |
| 2011/0252684 | A1 | 10/2011 | Ufer et al. |
| 2011/0267196 | A1 | 11/2011 | Hu et al. |
| 2011/0295083 | A1 | 12/2011 | Doelling et al. |
| 2012/0253220 | A1 | 4/2012 | Rai et al. |
| 2012/0142443 | A1 | 6/2012 | Savarese et al. |
| 2012/0316455 | A1 | 12/2012 | Rahman et al. |
| 2012/0316471 | A1 | 12/2012 | Rahman et al. |
| 2013/0018284 | A1 | 1/2013 | Kahn et al. |
| 2013/0096843 | A1 | 4/2013 | Yuen et al. |
| 2013/0237770 | A1 | 9/2013 | Sullivan et al. |
| 2014/0058703 | A1 | 2/2014 | Kimishima et al. |
| 2014/0073486 | A1 | 3/2014 | Ahmed et al. |
| 2014/0088378 | A1 | 3/2014 | Muzet |
| 2014/0089243 | A1 | 3/2014 | Oppenheimer |
| 2014/0135594 | A1 | 5/2014 | Yuen et al. |
| 2014/0172362 | A1 | 6/2014 | Burton et al. |
| 2014/0176422 | A1 | 6/2014 | Brumback et al. |
| 2014/0176475 | A1 | 6/2014 | Myers et al. |
| 2014/0180022 | A1 | 6/2014 | Stivoric et al. |
| 2014/0200474 | A1 | 7/2014 | Selvaraj et al. |
| 2014/0236036 | A1 | 8/2014 | De Haan et al. |
| 2014/0275854 | A1 | 9/2014 | Venkatraman et al. |
| 2014/0316305 | A1 | 10/2014 | Venkatraman et al. |
| 2014/0316584 | A1 | 10/2014 | Matsuoka et al. |
| 2014/0347366 | A1 | 11/2014 | Emori et al. |
| 2014/0364770 | A1 | 12/2014 | Slonneger et al. |
| 2014/0371635 | A1 | 12/2014 | Shinar et al. |
| 2015/0026647 | A1 | 1/2015 | Park et al. |
| 2015/0057967 | A1 | 2/2015 | Albinali |
| 2015/0164238 | A1 | 6/2015 | Benson et al. |
| 2015/0173671 | A1 | 6/2015 | Paalasmaa et al. |
| 2015/0320588 | A1* | 11/2015 | Connor ................. A61F 7/0085 607/104 |
| 2015/0355605 | A1* | 12/2015 | Franceschetti ....... H05B 1/0272 340/575 |
| 2015/0355612 | A1 | 12/2015 | Franceschetti et al. |
| 2016/0007914 | A1* | 1/2016 | Xu ....................... A61B 5/7455 600/534 |
| 2016/0007934 | A1 | 1/2016 | Arnold et al. |
| 2016/0022175 | A1 | 1/2016 | Arnold et al. |
| 2016/0022201 | A1 | 1/2016 | Arnold et al. |
| 2016/0022203 | A1 | 1/2016 | Arnold et al. |
| 2016/0051184 | A1 | 2/2016 | Wisbey et al. |

(56) References Cited

U.S. PATENT DOCUMENTS

| | | |
|---|---|---|
| 2016/0066716 A1 | 3/2016 | Rao |
| 2016/0151603 A1 | 6/2016 | Shouldice et al. |
| 2016/0235359 A1 | 8/2016 | Cho et al. |
| 2016/0246259 A1 | 8/2016 | Zhang |
| 2016/0270718 A1 | 9/2016 | Heneghan et al. |
| 2017/0312477 A1 | 11/2017 | Hashizaki et al. |
| 2017/0347946 A1 | 12/2017 | Arnold et al. |
| 2017/0347949 A1 | 12/2017 | Arnold et al. |
| 2017/0352287 A1 | 12/2017 | Arnold et al. |
| 2018/0064388 A1 | 3/2018 | Heneghan et al. |
| 2019/0038185 A1 | 2/2019 | Arnold et al. |
| 2019/0371197 A1 | 12/2019 | Arnold et al. |

FOREIGN PATENT DOCUMENTS

| | | |
|---|---|---|
| CN | 104812300 | 7/2015 |
| EP | 2 380 493 | 10/2011 |
| JP | 2008194400 | 8/2008 |
| KR | 101 439 463 | 9/2014 |
| WO | WO 2012/170586 | 12/2012 |
| WO | WO 2012/170924 | 12/2012 |
| WO | WO 2012/171032 | 12/2012 |
| WO | WO 2014/047310 | 3/2014 |
| WO | WO 2015/119726 | 8/2015 |
| WO | WO 2015/127067 | 8/2015 |
| WO | WO 2016/003269 | 1/2016 |
| WO | WO 2018/048951 | 3/2018 |

OTHER PUBLICATIONS

U.S. Final Office Action, dated Jun. 15, 2017, issued in U.S. Appl. No. 15/171,049.
U.S. Office Action, dated May 3, 2018, issued in U.S. Appl. No. 15/171,049.
U.S. Notice of Allowance, dated Dec. 31, 2018, issued in U.S. Appl. No. 15/171,049.
U.S. Office Action, dated Nov. 30, 2016, issued in U.S. Appl. No. 15/192,455.
U.S. Final Office Action, dated Jun. 21, 2017, issued in U.S. Appl. No. 15/192,455.
U.S. Office Action, dated May 14, 2018, issued in U.S. Appl. No. 15/192,455.
U.S. Notice of Allowance, dated Dec. 31, 2018, issued in U.S. Appl. No. 15/192,455.
U.S. Office Action, dated Dec. 28, 2016, issued in U.S. Appl. No. 15/199,113.
U.S. Final Office Action, dated Jul. 28, 2017, issued in U.S. Appl. No. 15/199,113.
U.S. Office Action, dated Mar. 6, 2019, issued in U.S. Appl. No. 15/438,643.
U.S. Final Office Action, dated Oct. 11, 2019, issued in U.S. Appl. No. 15/438,643.
U.S. Office Action, dated Jun. 24, 2016, issued in U.S. Appl. No. 14/859,192.
U.S. Office Action, dated Feb. 8, 2017, issued in U.S. Appl. No. 14/859,192.
U.S. Notice of Allowance, dated Aug. 17, 2017, issued in U.S. Appl. No. 14/859,192.
U.S. Office Action, dated Apr. 18, 2016, issued in U.S. Appl. No. 14/877,912.
U.S. Final Office Action, dated Dec. 1, 2016, issued in U.S. Appl. No. 14/877,912.
U.S. Office Action, dated Jul. 24, 2017, issued in U.S. Appl. No. 14/877,912.
U.S. Office Action, dated Jan. 25, 2018, issued in U.S. Appl. No. 14/877,912.
U.S. Notice of Allowance, dated May 11, 2018, issued in U.S. Appl. No. 14/877,912.
U.S. Office Action, dated Apr. 22, 2016, issued in U.S. Appl. No. 14/877,920.
U.S. Final Office Action, dated Aug. 30, 2016, issued in U.S. Appl. No. 14/877,920.
U.S. Notice of Allowance, dated Feb. 13, 2017, issued in U.S. Appl. No. 14/877,920.
U.S. Office Action, dated Jun. 1, 2016, issued in U.S. Appl. No. 14/877,922.
U.S. Final Office Action, dated Nov. 16, 2016, issued in U.S. Appl. No. 14/877,922.
U.S. Office Action, dated Mar. 11, 2019, issued in U.S. Appl. No. 16/058,423.
U.S. Final Office Action, dated Jul. 30, 2019, issued in U.S. Appl. No. 16/058,423.
U.S. Office Action, dated Dec. 16, 2019, issued in U.S. Appl. No. 16/058,423.
International Search Report and Written Opinion—PCT/US17/50344—ISA/EPO—dated Mar. 2, 2018.
International Preliminary Report on Patentability—PCT/US17/50344—ISA/EPO—dated Mar. 21, 2019.
Chinese First Office Action, dated Nov. 1, 2019, in Application No. CN 201910277917.9.
Ribeiro, Pedro Ramiro Guimaraes, "Sensor based sleep patterns and nocturnal activity analysis," Faculdade de Engenharia da Universidade do Porto, Jul. 17, 2014, 38 pages.
International Search Report and Written Opinion—PCT/US17/30259—ISA/EPO—dated Oct. 4, 2017.
Banerjee et al., "Monitoring Patients in Hospital Beds Using Unobstrusive Depth Sensors," IEEE. 2014. 4 pgs.
"BPMS System Seating & Positioning Analysis," Tekscan. Document metadata indicates creation date of Oct. 30, 2015. 2 pgs.
"Eccentric Rotating Mass Vibration Motors," Precision Microdrives. Downloaded Nov. 9, 2016. 5 pgs.
"LifeBed," Hoana Medical, Inc. Downloaded Apr. 1, 2016. 3 pgs.
"Linear Resonant Actuators—LRAs," Precision Microdrives. Downloaded Nov. 9, 2016. 6 pgs.
"Optical Measurement Solutions," HBM Fiber Sensing. Document metadata indicates creation date of Oct. 30, 2015. 12 pgs.
"Science Behind the Sleep Tracker," Beddit. Downloaded Apr. 8, 2016. 9 pgs.
"The Smart Bed: The Ideal Platform for Improved Health and Better Care," BAM Labs. Jul. 2012. 9 pgs.

\* cited by examiner

SLEEP MONITORING SYSTEM WITH OPTIONAL ALARM FUNCTIONALITY

CROSS-REFERENCE TO RELATED APPLICATIONS

This application claims benefit of priority under 35 U.S.C. § 119(e) to U.S. Provisional Patent Application Nos. 62/329,979, filed Apr. 29, 2016, and titled "SLEEP MONITORING SYSTEM," and 62/434,910, filed Dec. 15, 2016, and titled "SLEEP MONITORING SYSTEM WITH OPTIONAL ALARM FUNCTIONALITY," both of which are hereby incorporated by reference herein in their entireties.

BACKGROUND

Sleep monitoring systems may be used in hospitals and other patient-care facilities to monitor patients for vital signs and other biometric data. Such systems are typically designed for use with hospital beds and thus with single individuals.

SUMMARY

The present inventors have conceived of various useful systems, techniques, and apparatuses that may be used, among other things, to facilitate simultaneous sleep data collection for multiple people, e.g., two people, that sleep in a bed together. The present inventors also conceived of other functionality as well.

In some implementations, a sleep monitoring system is provided that includes one or more carriers configured to be placed above or under a bed mattress and under or over one or more people lying on the bed mattress. The sleep monitoring system may also include one or more first sensors distributed across at least one of the one or more carriers, the one or more first sensors being of a first type of sensor, and one or more second sensors distributed across at least one of the one or more carriers, the one or more second sensors being of a second type of sensor different from the first type of sensor. The sleep monitoring system may also include one or more processors and one or more computer readable storage devices that include computer executable instructions that, when executed by the one or more processors, cause the one or more processors to obtain global sensor data from the one or more first sensors and the one or more second sensors and to generate sleep data for a sleeper from the global sensor data, the sleep data including data regarding one or more physiological metrics of the sleeper.

In some implementations, a sleep monitoring system may be provided that includes one or more processors and a computer readable storage device that includes computer executable instructions that, when executed by the one or more processors, cause the one or more processors to obtain global sensor data from a plurality of first sensors that are spatially distributed across a bed, analyze the global sensor data and extract first extracted sensor data regarding a first person from the global sensor data and second extracted sensor data regarding a second person from the global sensor data, identify a first component in the global sensor data caused by motions of the first person, and reduce a contribution of the first component to the second extracted sensor data.

In some implementations, a sleeper identification system is provided. The sleeper identification system may include one or more processors and a computer readable storage device that includes computer executable instructions that, when executed by the one or more processors, cause the one or more processors to: obtain first sleep data for a first person from a sleep monitoring system, the first sleep data based, at least in part, on first extracted sensor data collected from a sleep monitoring sensor apparatus; determine that the first person is associated with a first user account based, at least in part, on the first sleep data or the first extracted sensor data; and associate the first sleep data with the first user account.

In some implementations, a wake-up alarm system may be provided. The wake-up alarm system may include one or more carriers configured to be placed above or under a bed mattress having a thickness along a first axis, a width along a second axis, and a length along a third axis. The thickness may be less than the width, the width may be less than the length, and the first axis, the second axis, and the third axis may all be perpendicular to one another. The wake-up alarm system may further include a first alarm, a second alarm, one or more processors, and a memory. The first alarm and the second alarm may be located in positions on the one or more carriers that are spaced apart along an axis parallel to the second axis by at least 40% of the width when the one or more carriers are placed above or under the bed mattress in an in-use configuration, the one or more processors may be communicatively connected with the memory, the first alarm, and the second alarm, and the memory may store instructions that, when executed by the one or more processors, cause the one or more processors to: activate the first alarm responsive to a first signal and activate the second alarm responsive to a second signal that is independent from the first signal.

These and other implementations are discussed below, and this disclosure is not limited to only the implementations summarized above; additional implementations will be evident from the discussion below.

BRIEF DESCRIPTION OF THE DRAWINGS

The included drawings are for illustrative purposes and serve only to provide examples of possible structures for the concepts disclosed herein. These drawings in no way limit any changes in form and detail that may be made by one skilled in the art without departing from the spirit and scope of the disclosed embodiments.

Figure 1:
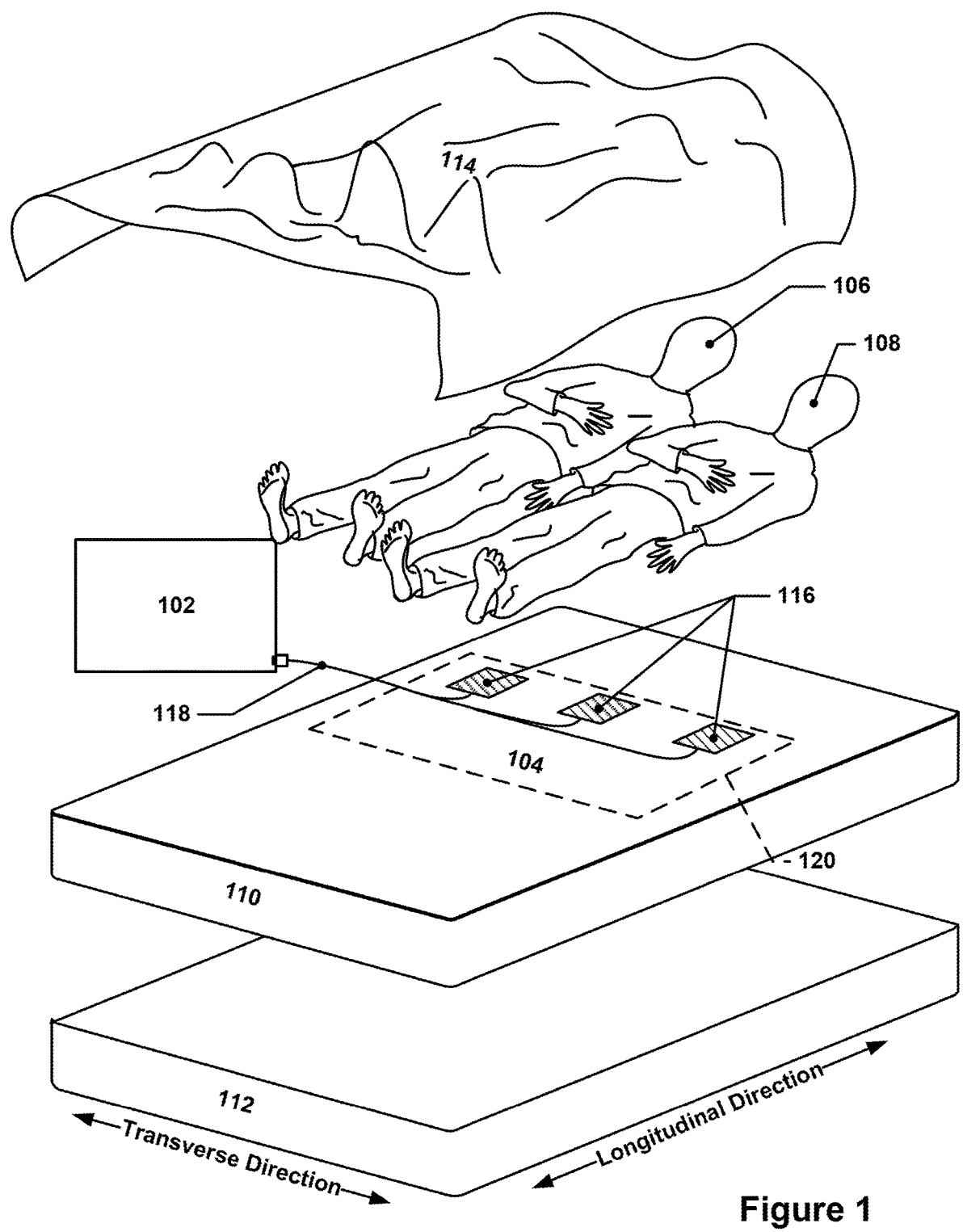
FIG. 1 depicts an exploded view of one example of a sleep monitoring system.

Throughout the drawings, the same reference numerals and characters, or reference numbers sharing the same last two digits, unless otherwise stated or suggested by the text or Figures, are used to denote like features, elements, components, or portions of the illustrated embodiments. Moreover, while the subject concepts will now be described in detail with reference to the drawings, the description is done in connection with the illustrative embodiments. It is intended that changes and modifications can be made to the described embodiments without departing from the true scope and spirit of the disclosed subject matter, as defined by the appended claims.

DETAILED DESCRIPTION

The present inventors have conceived of a sleep monitoring system that tracks and monitors various physiological parameters for multiple users, such as a couple, parents and a child, or couple and a pet, sleeping in a common bed. The sleep monitoring system may include or be connected with a sleep monitoring sensor apparatus, which may include a sensor mesh of at least two first sensors of a particular type, e.g., motion sensors or pressure sensors, that are spatially separated from one another on a carrier. The term "carrier" is used herein to refer to a substrate that acts as a carrier for a sensor mesh in a sleep monitoring sensor apparatus. The carrier may, for example, be a thin, flexible sheet of material or may be a woven material or textile, such as cotton, silk, nylon, etc. The carrier may be in the form of a pad, bedsheet, blanket, duvet or comforter cover, fitted sheet, or mattress pad. The sleep monitoring sensor apparatus may include one carrier or multiple carriers in different implementations, e.g., a carrier, such as a mattress pad, with pressure sensors that is located beneath a person who is sleeping in the bed, and another carrier, such as a blanket, that may have accelerometers and is located above the person in the bed. In some implementations, the sensor mesh may also include one or more second sensors of at least one other type (or multiple additional sensor sets, each featuring a different type of sensor) that may provide a different type of data from the other sensors, e.g., the first sensors, in the sensor mesh. As used herein, the term "sensor mesh" refers to an array or arrangement of sensors over a distributed area; such meshes may be one-dimensional, two-dimensional, or three-dimensional. For example, in some implementations, two sensors may be spaced apart some distance across a bed, forming a single-dimensional array or arrangement. In another implementation, two sensors may be stacked on top of one another, thereby forming a single-dimensional array in a direction generally perpendicular to the bed's upper surface. In another implementation, three or more sensors may be arranged along two different, non-colinear axes, thereby forming a two-dimensional array or arrangement. It is to be understood that while the sensors may be spaced apart in a regular fashion, e.g., each equidistant from neighboring sensors, some implementations may feature non-equal spacing or other asymmetry. Data from these sensors may be captured and analyzed using data extraction techniques, such as independent component analysis, in order to separate out signals that are attributable to each person in the bed.

FIG. 1 depicts an exploded view of one example of a sleep monitoring system. In FIG. 1, a mattress 110 for two sleepers, first sleeper 106 and second sleeper 108, is shown. Located beneath the first sleeper 106 and the second sleeper 108 is a sleep monitoring sensor apparatus 104, which may be communicatively connected with a sleep monitoring system 102 by a communications interface 118, which is, in this example, a cable or other hard-wired connection. The sleepers may be covered by a blanket 114 or other covering, and the mattress 110 may rest on a box spring 112 or other support, e.g., a bed frame (not shown) or, if desired, the floor. The term "sleeper" is used herein to refer to a person that is sleeping (or attempting to sleep) in a bed. The term "co-sleeper" may be used herein to refer to a person that is sleeping or attempting to sleep in a bed occupied by one or more additional people, although the term "sleeper" may also be used to refer to one of two or more people sleeping in a common bed.

The sleep monitoring sensor apparatus 104 may include a plurality of sensors 116 (also referred to as a sensor mesh) that are spatially distributed across a carrier 120 of the sleep monitoring sensor apparatus 104.

It is to be understood that the data that is collected from each of the sensors in the sensor mesh in such a system is not definitively pre-associated with a particular individual, as would be the case, for example, in a hypothetical system with a plurality of sensors in which the sensors located on the left half of a mattress are pre-associated with a person known to sleep on the left side of the bed and in which the other sensors, located on the right half of the mattress, are pre-associated with a person known to sleep on the right side of the bed. In such a hypothetical system, these two sets of sensors may, in effect, be operated as two independent sensor networks, each measuring data assumed to be produced by a different person. However, if a person who normally sleeps on the right side of the bed strays into the left side of the bed while the person who normally sleeps on the left side of the bed is also there, then the sensors on the left side of the bed may measure physical phenomena caused by both the right-side sleeper and the left-side sleeper but may only attribute such signals to the left-side sleeper, which can lead to inaccurate measurements of the left-side sleeper's physiological condition and/or sleep characteristics.

In contrast, the sensor meshes in the systems described herein may collect data across a distributed area of a bed without a pre-set allocation of each sensor to a particular user; such data is referred to herein as "global sensor data," which is used herein to refer to a collection of sensor data streams that are obtained from a sensor mesh of a sleep monitoring sensor apparatus. The global sensor data may include data or data streams from multiple sensors of the same type, although in some implementations, the global sensor data may include data streams for multiple sets of sensors, each set of sensors having a plurality of sensors and each set of sensors having a different type of sensor. In some instances, the ordinal indicators first, second, etc., may be used to refer to different subportions of the global sensor data, e.g., "first global sensor data" may be used to refer to the global sensor data arising from a plurality of first sensors (of a first type), and "second global sensor data" may be used to refer to the global sensor data arising from a plurality of second sensors (of a second type). Global sensor data may take the form of a spatially distributed set of pressure readings over time, a spatially distributed set of acceleration or other movement-related readings over time, a spatially distributed set of temperature measurement readings over time, and so forth, as well as combinations thereof.

The global sensor data may include a signal from each sensor in the sensor mesh. Depending on the number of people in the bed, the relative activity levels of people in the bed, and the relative position of each sensor with respect to the people in the bed, each sensor signal may be entirely attributable to the movements or physiological state of only one person in the bed or may be attributable to the movements or physiological states of two or more people in the bed.

The sleep monitoring system may analyze the global sensor data using any of a variety of different analysis techniques, such as independent component analysis or other techniques, in order to identify and extract signals from the global sensor data that are specific to each of the people in the bed. Such techniques may be used to extract such signals regardless of whether each person remains in a particular position on the bed or shifts around the bed over time, including situations in which two people end up sleeping next to one another on one side of the bed. The signals that are extracted and associated with a particular person in the bed are referred to herein as "extracted sensor data," e.g., first extracted sensor data for a first person in the bed, second extracted sensor data for a second person in the bed, etc. For ease of discussion, the examples discussed herein will assume that there are two people in a bed, but it is to be understood that the techniques and systems discussed herein are also applicable to situations in which there are more than two people sleeping in a bed, e.g., such as parents and one or more children.

Once the sleep monitoring system has extracted different sets of extracted sensor data that are each attributable to a different person in the bed from the global sensor data, the sleep monitoring system may utilize the extracted sensor data in a variety of ways. For example, the sleep monitoring system may perform further analysis on the extracted sensor data in order to generate data regarding various sleep-related or physiological metrics, e.g., total time asleep, number of waking events during a sleep session, heart rate over time during a sleep session, and the like, which are referred to herein as "sleep data." Thus, the term "sleep data" is used herein to refer to data that describes a physiological condition or other metric associated with particular sleeper's sleep activity. Sleep data may be derived, at least in part, from data obtained from the sensor mesh of the sleep monitoring sensor apparatus. Examples of sleep data may include, but are not limited to: breathing rate during a sleep session, heart rate and/or resting heart rate, average heart rate and/or resting heart rate, heart rate variability and/or resting heart rate variability, body temperature, bed temperature, total time actually spent asleep during a sleep session, total time actually spent awake during a sleep session, time in bed or sleep session duration, the number of wake events that occur during a sleep session after sleep onset occurs, the number of times that a person gets out of bed during a sleep session (and subsequently re-enters the bed during the sleep session), time spent in one or more of the five commonly-recognized sleep stages of Wake, N1, N2, N3, and REM during the sleep session, and time spent in one or more of other commonly recognized sleep stages, e.g., deep sleep, light sleep, REM sleep, or any other determinable sleep state.

Each of these types of sleep data may be determined on a continuous basis, e.g., driven by the sampling rate of the sensors used, or discretized into regular epochs or periods, e.g., determined for every 30 seconds or 60 seconds. The different types of sleep data may also be processed in one or more ways in order to remove noise or provide a more representative signal, e.g., by averaging or by assigning a value based on an overall trend indicated by data within a period or epoch. For example, a person may experience multiple sleep stages during a particular epoch or period, but the sleep monitoring system may assign a sleep stage to that epoch that is representative of the predominant sleep stage experienced during that epoch. Thus, for example, each sleep data measurement period may have a length of one minute, and may include measurements such as average heart rate during that period, maximum heart rate during that period, average breathing rate during that period, and predominant sleep stage during that period. It is also to be understood that sleep data may be organized according to multiple different schemes, e.g., some sleep data for a sleeper may be provided based on one-minute epochs, whereas other sleep data for the same sleeper during the same timeframe may be provided based on 10-minute epochs—the same epoch size does not necessarily need to be used for all sleep data for a sleeper.

The sleep monitoring system may obtain such data without requiring the sleeper(s) to wear any sensor devices, i.e., the sleeper need not wear a fitness tracking device in order for the sleep data to be obtained (although if the sleeper wears a fitness tracking device, this may enable certain of the techniques discussed herein). The terms "sleep session" or "time in bed," used interchangeably herein, refer to an interval of time during which a person is engaged in the act of sleeping or trying to go to sleep. It is bounded by the person's bedtime, which generally refers to time at which the person has gone to bed and is trying or preparing to go to sleep, and the person's waketime, which refers to the time when the person gets up without going back to sleep. It is to be understood that a sleep session may be punctuated by various periods of wakefulness, e.g., when the person gets up to use the bathroom or when the person's sleep is interrupted by other, external stimuli, such as changing the diaper of a crying baby or feeding a baby, but such waking events generally do not signal the end of the sleep session if the person then goes back to sleep soon afterwards. The term "bedtime" is used herein to refer to the time at which a person goes to bed, i.e., has climbed into bed and is sitting, lying, or otherwise on the mattress or bed. The bedtime may, in some cases, be simultaneous or near-simultaneous with the onset of actual sleep, although most people spend some time in bed before falling asleep, e.g., reading or using a tablet or smartphone. Correspondingly, the term "waketime" is used herein to refer to the time at which a person wakes up from a sleep session without then going back to sleep (for a significant period of time, e.g., without going back to sleep for at least an hour or more—obviously the person will need to go back to sleep at some point). The term "sleep onset" is used herein to refer to the moment in a sleep session when a person first drifts off to sleep. The term "sleep onset latency" refers to the amount of time that elapses between when a person first goes to bed, i.e., the bedtime, and when sleep onset occurs. All of these parameters, e.g., bedtime, sleep session (in terms of duration, start time/end time, etc.), waketime, and so forth, may be viewed as data structures representative of such information, and may be stored in memory by a computing system or otherwise processed by such a computing system.

In some implementations, the extracted sensor data from one person may be used to correct the extracted sensor data or the sleep data for another person. For example, if two people are sleeping close to one another in bed and the first person is a restless sleeper, their movements may not only be evident in the first extracted sensor data for the first person, but may also be reflected in the second extracted sensor data for the second person. For example, if the first person tosses and turns, a first pressure sensor located beneath the first person may register pressure changes caused by the first person's movements. However, because mattresses are flexible and compliant, such movements may also cause the mattress to flex and bounce in response, which may, in turn, cause sympathetic movements in the second person, which may cause a second pressure sensor located beneath the second person to register pressure changes as well, likely of a lesser magnitude than those registered by the first pressure sensor. The term "driving" is used herein, in combination with terms such as "motion," "movement," "signal," "component," or "oscillations," to refer to events or signals attributable to the movement of one co-sleeper that cause "sympathetic" events or signals in the extracted sensor data of another co-sleeper. The term "sympathetic" is used herein to indicate movements or data artifacts associated with one co-sleeper that are driven by driving movements made by the other co-sleeper. Thus, for example, if person A moves and produces a localized oscillation in the extracted sensor data for person A, there may be a corresponding sympathetic movement by person B, who is sleeping in the same bed as person A, that is driven by the driving movement of person A. This may result in a sympathetic localized oscillation in the extracted sensor data for person B that occurs at the same time as the driving localized oscillation in the extracted sensor data for person A.

The pressure changes registered by the second sensor but caused by motion of the first person would thus be observable in the second extracted sensor data for the second person. These sympathetic movements of the second person, however, are not necessarily indicative of restlessness on the part of the second person, and it may be undesirable to determine or calculate sleep data for the second person such that it is based on such movements. Accordingly, in some implementations, the system may take steps to mitigate or correct such "sympathetic" artifacts in a particular person's sleep data or extracted sensor data.

The sleep monitoring system, in some implementations, may also include a sleeper identification component or engine (SIC or SIE) that may, based at least in part on the data collected by the sensor mesh, associate the sleep data collected for a particular sleeper with a particular user account. For example, a given sleep monitoring system connected to a sensor mesh installed in a bed may have been associated with two separate individuals, both of whom sleep in the bed, during a registration process. Each of these people may have different physiological characteristics, e.g., weight, resting breathing rate, resting heart rate, sleep patterns, etc., that may be observable in some way in the person's sleep data. The system may, based on such differing characteristics, determine that sleep data collected for a particular individual is sleep data for a specific one of the two individuals registered with the sleep monitoring system, and may then associate such sleep data with a user account of that individual.

The present inventors have also conceived of a different sleep monitoring system that may include a sleep monitoring sensor apparatus that does not necessarily include a plurality of sensors of a first type. In such an alternative implementation, the sleep monitoring sensor apparatus may include at least one first sensor of a first type and at least one second sensor of a second, different type, e.g., at least one pressure sensor and at least one accelerometer, or at least one pressure sensor and at least one temperature sensor. Such a sleep monitoring system may use the data obtained from the different sensors that are included to determine sleep data for a sleeper that is sleeping in a bed that is equipped with such a sleep monitoring sensor apparatus. In some implementations, such a sleep monitoring system may nonetheless include multiple sensors of the same type that are spatially distributed across a carrier, similar to the sleep monitoring system implementations discussed earlier above.

For sleep monitoring systems having two different types of sensors, regardless of whether there are multiple instances of each type of sensor or only single instances of each type of sensor, the inclusion of different sensor types may facilitate certain types of enhanced functionality. For example, some sensors, such as piezoresistive pressure sensors or force-sensitive resistor pressure sensors, may be well suited for monitoring whether or not a person is present in the bed (by virtue of their weight being detected by the pressure sensor) or the person's breathing rate. Other sensors, such as accelerometers, for example, may be better at measuring gross movement events, e.g., sudden movements indicating restless sleep. Thus, such sleep monitoring systems may provide enhanced functionality over sleep monitoring systems using only a single type of sensor. It is to be understood that reference to sensors of a "type of sensor," as the term is used herein, refers to sensors that share a common operating principle and that measure the same physical phenomena. In many instances, such sensors may all be of the same model or may otherwise be structurally similar or identical, although different sensor models may be used as well and still be of the same "type." For example, MEMS-based accelerometers may be used that all operate under the same general principles of operation, but that have different sensitivities or dynamic ranges, but such sensors may still be viewed as being of the same "type."

Some sensors only respond to changes (e.g., accelerometers or piezoelectric sensors) in a physical condition or state, in which case it is possible that only active movement of the person is detected. Other sensors such as a piezoresistive, capacitive, or load cell-based sensors also may provide an absolute value of a steady-state value, in addition to detecting changes in the value. For example, a piezoresistive pressure sensor may generate a resistance that is proportionate to the amount of pressure (or distributed force) that it is subjected to; such a resistance may remain generally constant if the pressure does not change, thereby allowing for continuous monitoring of a steady state condition, e.g., is a person in the bed? In contrast, a piezoelectric pressure sensor may generate an electrical charge in response to a change in pressure, but such a charge may quickly dissipate in the absence of further pressure changes. Such sensors may thus be poorly suited to determining if a person is in or out of a bed, but may be well adapted for measuring other physiological characteristics, such as the occurrence of gross movement and even, in some implementations, less noticeable movements. As used herein, the term "gross movement" refers to body movements such as limb movements or body reorientations or repositioning; gross movement does not include a person's natural breathing movements or heartbeat-related movements, as well as minor shifts in position or orientation, e.g., movements of one or two centimeters.

A preferred embodiment may include sensors of both types. By detecting absolute pressure levels at distributed locations across a sensor mesh, it is possible to estimate the center of gravity of the subject, and hence infer body location. By analyzing the pattern of absolute pressure across the different sensor units, it is also possible to infer body position (e.g., prone versus supine versus side sleeping).

The above discussion provides a high-level overview of the systems and techniques discussed herein. The following discussion, in which reference to the Figures is made, elaborates further on these, and other, concepts.

Sleep Monitoring Sensor Apparatus

As discussed above, the sleep monitoring system may utilize a sleep monitoring sensor apparatus that includes a sensor mesh of spatially-distributed sensors distributed on a carrier of some sort.

The carrier may, for example, be a sheet, coverlet, mattress pad, or other article designed to be used with a mattress of a particular size. In some implementations, the carrier may be sized smaller than a particular mattress size so as to be usable with multiple different mattress sizes, e.g., the carrier may, for example, have a width of 52" so as to allow it to be placed underneath a mattress pad for a full-size mattress, a queen-size mattress, or a king-size mattress. This example is to be understood to be non-limiting, and smaller sized carriers may be used in some implementations. In some implementations, the carrier may be provided by a fitted sheet, e.g., a sheet sized for a specific mattress size and having elastically-hemmed corners to allow the fitted sheet to be slipped over a mattress of that mattress size. In some implementations, the carrier may be designed to be placed under a mattress.

The sensor mesh may be permanently woven or installed into or onto the carrier, or may be removable, e.g., to facilitate washing or replacement of the carrier. In such removable implementations, the sensor mesh may include individual sensors located at the ends of individual cables or cable branches that are each routed through the carrier to the sensor locations, or the sensor mesh may be mounted on a secondary carrier that is designed to be slipped inside of the carrier, e.g., a backing sheet or flexible printed circuit substrate (secondary carrier) that may be inserted into a cotton cover or mattress pad (the carrier). Such a configuration may allow the carrier to be washed without risking damaging the sensors. In some implementations, the sensor mesh may be constructed so as to be waterproof, e.g., by using washable piezo-resistive fabric (for pressure sensors) that is attached to a waterproof and heat-insensitive connector. Sensors such as accelerometers may be waterproofed by encasing them in waterproof enclosures or coating them with a waterproof conformal coating.

Figure 2:
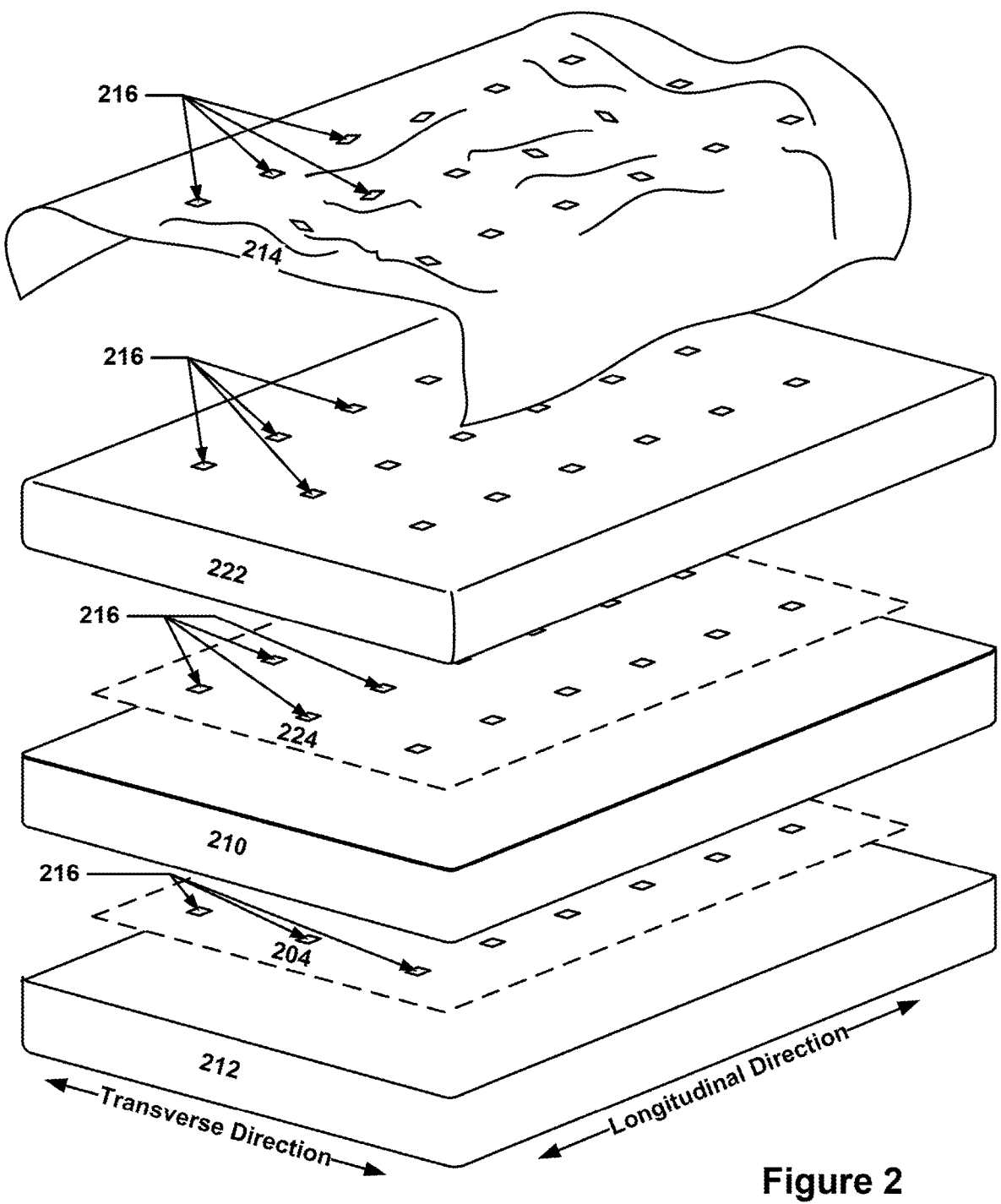
FIG. 2 depicts an exploded view of a typical bed arrangement and shows the various locations that a sleep monitoring sensor apparatus may be located.

FIG. 2 depicts an exploded view of a typical bed arrangement and shows the various locations that a sleep monitoring sensor apparatus may be located. As can be seen, the bed arrangement may include, for example, a blanket or sheet 214, a fitted sheet 222, a mattress pad 224 (which may be fitted, similar to a fitted sheet, or may simply be an overlay), a mattress 210, and a box spring 212. It is to be understood that some of these components may be omitted, depending on the sleep preferences of the user. For example, many beds do not utilize a box spring, and so a box spring may be optional. Sleep monitoring sensor apparatuses having sensors 216 may be configured to be located in any of a variety of locations in a bed arrangement. For example, a sleep monitoring sensor apparatus such as that represented by carrier 204 may be located in between the box spring 212 and the mattress 210. Alternatively, a sleep monitoring sensor apparatus may be integrated into the mattress pad 224, in which case the mattress pad 224 may include or form the carrier. In some other implementations, the sensors 216 may be integrated with the fitted sheet 222, which may form or include the carrier. In yet other implementations, the sensors 216 may be integrated into the blanket or sheet 214. It is to be understood that some implementations of a sleep monitoring sensor apparatus may include multiple carriers that may be integrated into a common bed accessory, e.g., multiple carriers that may be inserted into a mattress pad, or may include multiple carriers that may be distributed between two or more different bed accessories, e.g., a first carrier with pressure sensors that may be integrated into a mattress pad and a second carrier with accelerometers that may be integrated with a blanket or sheet.

The number of sensors in the sensor mesh may be as few as two, but additional sensors may increase the sensitivity and fidelity of the sleep monitoring system. For example, a 2×2 grid of sensors may be used in some implementations, or a 1×3 array of sensors may be used in other implementations. The number of sensors used may also be much higher, e.g., an 8×8 array of sensors. The number and arrangement of sensors may be selected according to a variety of factors (desired degree of sensor coverage, cost, complexity, etc.), although in most implementations, there will be at least two sensors spaced apart from one another on the carrier in at least the transverse direction, and potentially also in the longitudinal direction. This spatial distribution of sensors in the transverse direction allows the sleep monitoring system to monitor two different sleepers who sleep in the same bed and who may not remain neatly on their respective "sides" of the bed—the transverse orientation may allow for the relative positioning of each sleeper in the bed to be dynamically determined, at least with respect to the left-right direction and for extracted sensor data to be associated with each sleeper. The term "longitudinal," with respect to an axis or direction of a bed mattress or sensor mesh used with a bed mattress, refers to an axis or direction that is parallel to an edge of the mattress and that extends in a direction generally associated with the head-to-foot (or vice-versa) direction a person would normally assume when sleeping in the bed. For most mattresses, such as twin, full, queen, king, and California king size mattresses, the longitudinal direction or axis would be parallel to one of the longer edges of the mattress. Conversely, the term "transverse," with respect to an axis or direction of a bed mattress or sensor mesh used with a bed mattress, refers to an axis or direction that is parallel to an edge of the mattress and that extends in a direction generally associated with the left-to-right (or vice-versa) direction a person would normally assume when sleeping in the bed. For most mattresses, such as twin, full, queen, king, and California king size mattresses, the transverse direction or axis would be parallel to one of the shorter edges of the mattress.

Figure 3:
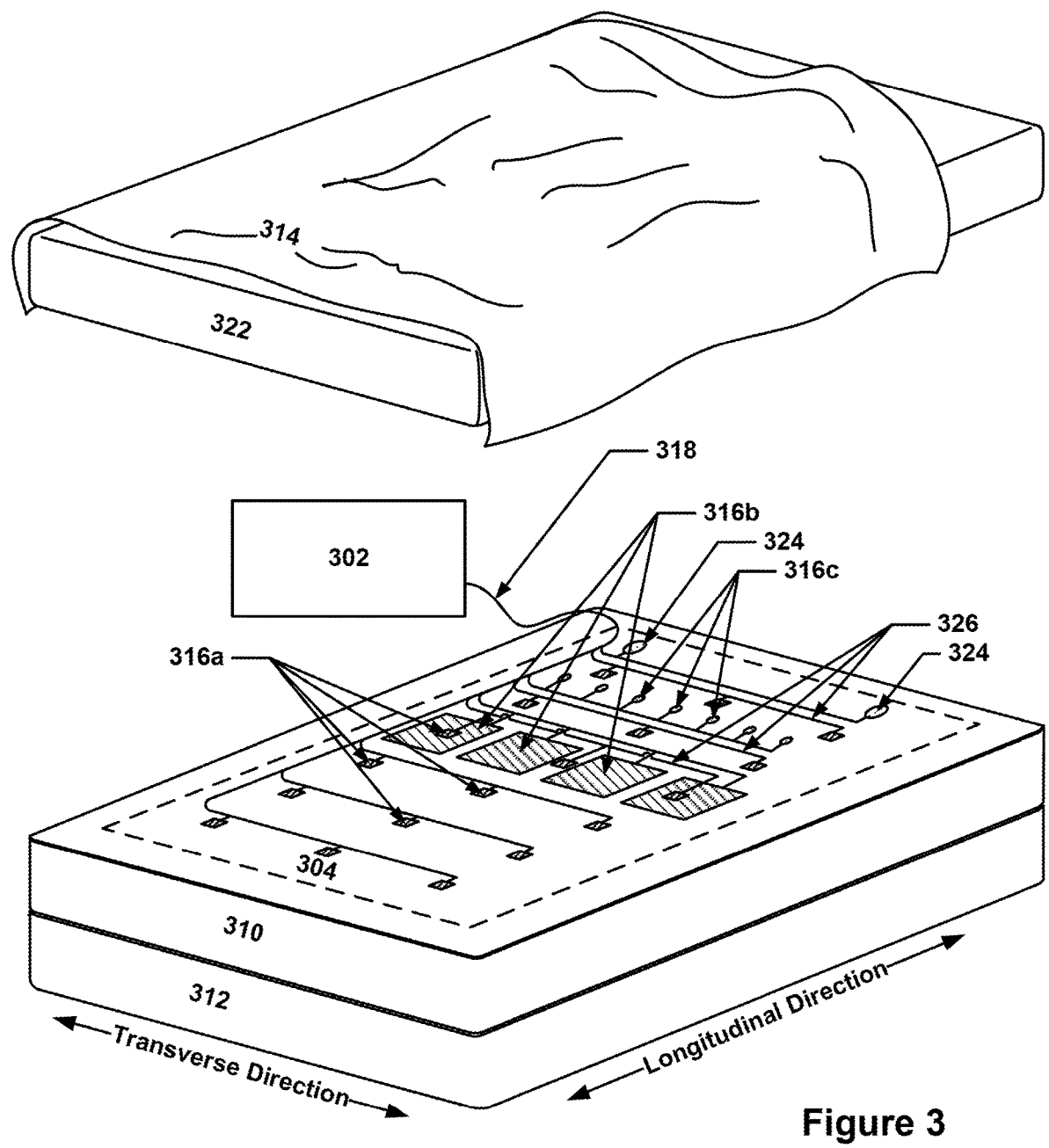
FIG. 3 depicts an example sleep monitoring sensor apparatus that may be placed under a fitted sheet.

The sensor mesh may include only one type of sensor, or may include multiple different types of sensor. FIG. 3 depicts an example sleep monitoring sensor apparatus that may be placed under a fitted sheet, e.g., on top of a mattress 310. The sleep monitoring sensor apparatus may include, for example, a carrier with a sensor mesh having a plurality of spaced-apart first sensors of a first type and, optionally, a plurality of spaced-apart second sensors of a second type; the first type may be different from the second type. In a further example, the sensor mesh may include a plurality of spaced-apart third sensors of a third type, with the third type different from the first and second types. For example, in FIG. 3, a carrier 304 is depicted that includes a sensor mesh that includes a 3×6 array of first sensors 316a, a 4×1 array of second sensors 316b, and a 7×1 array of third sensors 316c. Each of these sensor arrays may include different types of sensors, e.g., the first sensors may all be accelerometers, the second sensors may all be pressure sensors, and the third sensors may all be temperature sensors. Each sensor array may extend over coextensive areas, or may extend over differently-sized areas (as shown in the example of FIG. 3). Additionally, some sensors, such as some of the sensors 316a, may be stacked on top of other sensors, e.g., such as sensors 316b. This may provide additional benefit in that collocated, e.g., stacked, sensors may be assumed to be responsive to the same inputs, which may allow for more effective signal processing and better correlation between sensor data streams. For example, if it is determined from pressure data from an array of pressure sensors that a particular pressure sensor is closest to a person's torso, then a collocated accelerometer may also be determined to be closest to the person's torso, thus providing insight as to the source of the acceleration data collected by that accelerometer. The sensors 316a/b/c may be connected to electrical cabling or traces 326 that may allow power and data signals to be transmitted to or from the sensors 316a/b/c; the electrical cabling or traces 326 may be configured to communicate sensor data to the sleep monitoring system via a communications interface 318, which, in this example, is a cable, although other implementations may, as discussed later herein, utilize a wireless connection of some type for communications interface 318. The sleep monitoring sensor apparatus may be connected with a sleep monitoring system 302, which may extract data from the sensors and then calculate or determine one or more types of sleep data for sleepers in the bed using such extracted sensor data.

There is no upper limit to the number of sensor arrays of different types of sensors that may be included in the sensor mesh. The sensors of each type may be collocated with corresponding sensors of the other types, e.g., there may be three 4×4 arrays of three different sensor types, and each array location for the three different sensor types may correspond with an array location of sensors of the other two sensor types, or the sensors of each type may be arranged in different arrays, e.g., there may be a 4×4 array of first sensors of a first type, a 2×3 array of second sensors of a second type, and a 1×2 array of third sensors of a third type. Thus, while some implementations may feature multiple collocated sensors of different types, other implementations may have such sensors arranged differently. In implementations where two or more sensors of different types are collocated (or positioned very near to one another, e.g., within a centimeter or so), the collocated sensors may be integrated into a single sensor package or module, if desired, to facilitate assembly/integration of the sensors with the sensor mesh. It is to be understood that such an integrated sensor package would still include multiple sensors of different types, notwithstanding their integration into a single unitary assembly.

Different sensor types may be used to collect different types of data that may be used to evaluate different physiological metrics. For example, a mesh of pressure sensors may be used to measure a pressure distribution across a mattress and variations in pressure sensed by such pressure sensors may indicate one or more of gross movement of a sleeper, breathing rate of the sleeper, and heart rate of the sleeper. A mesh of temperature sensors may be used to measure a temperature distribution across a mattress, which may allow for body temperature of a sleeper to be monitored. Motion sensors may be used to measure gross movement and breathing rate of the sleeper. The term "motion sensor(s)" is used herein to refer to the broad class of sensors that measure, in some way, the rate of movement of the sensor itself with respect to a fixed, environmental frame of reference. Motion sensors may include accelerometers (which measure acceleration), magnetometers (which measure angular motion with respect to the local electromagnetic field), and gyroscopic sensors, which measure angular motion with respect to the global environment). Other types of sensors may also be thought of as motion sensors as well, and the above examples are not to be viewed as limiting. Pressure sensors are not considered to be motion sensors for the purposes of this disclosure since pressure sensors measure pressure exerted on them but do not provide insight as to the movement of the pressure sensors themselves.

A variety of different pressure sensors may be suitable for use in the sensor mesh. Such pressure sensors may include, for example, piezo-resistive pressure sensors, piezo-electric pressure sensors, and capacitive force sensors, which may be used as pressure sensors when their sensitive surface area is taken into account. Piezo-resistive pressure sensors are sensors that have a layer of piezo-resistive material that changes its resistance in response to pressure that is exerted on the layer; the resistance changes in a manner proportionate to the amount of pressure that is exerted on the layer, thereby providing a mechanism for determining how much pressure is exerted on the piezo-resistive pressure sensor's active area. Piezo-electric pressure sensors are sensors that have a layer of piezo-electric material that produces an electrical charge in response to pressure that is exerted on the layer; the amount of electrical charge generated is proportionate to the amount of pressure that is exerted on the layer, thereby providing a mechanism for determining how much pressure is exerted on the piezo-electric pressure sensor's active area. It is to be understood that such pressure sensors may also be thought of as "force" sensors, as pressure is simply force divided by area, so force sensors that are capable of sensing force applied over a distributed area may also be suitable. Capacitive force or pressure sensors may include a flexible dielectric layer that separates two electrode layers; changes in the dielectric layer thickness, such as may be caused by pressure exerted on the dielectric layer, may cause a change in capacitance between the electrodes across the dielectric layer, which may be measured to obtain an indication of the amount of such deformation that has occurred. These types of pressure sensors may be procured in very thin configurations, allowing them to be stitched or woven into a textile-based carrier, such as a mattress pad, relatively unobtrusively, e.g., such that a person sleeping on the carrier will not be discomfited by the presence of the sensors. The sensors may be connected with downstream electronics by way of discrete wires or by circuit traces that may, for example, be provided on the carrier.

Pressure sensors may be used to obtain a variety of insights regarding a person sleeping or resting on such sensors. As a person breathes, the amount of pressure that the person may exert on a pressure sensor, if the pressure sensor is in a position to register it, fluctuates in rhythm with the person's breathing, resulting in a pressure measurement signal that indicates the breathing rate of the person. Similarly, in some circumstances, even the minute movements associated with a person's heart rate may produce measurable pressure fluctuations in a pressure sensor, allowing such a pressure sensor to be used as a ballistocardiogram sensor.

Other sensors, as mentioned above, that may be used as an alternative to or complement of pressure-measurement sensors are motion sensors, such as accelerometers, magnetometers, gyroscopic sensors, etc. Such motion sensors may register movement of the sleeper, rather than pressure exerted by the sleeper. Motion sensors may, for example, register small vibrations in the carrier caused by nearby motions of the sleeper, or may register larger-scale displacements of the motion sensor, such as may be caused by the sleeper moving a leg in a way that causes the motion sensor to be displaced, as may occur if the motion sensor is woven or embedded into a sheet placed over the sleeper and the sleeper's movement causes the sheet to move. If such motion sensors are used, they may be selected from relatively sensitive, low-range sensors, as the movements that will be measured will be relatively low in magnitude. For example, accelerometers that are sensitive to sub-milli-g (where "g" refers to a standard earth gravity) accelerations may be used, as the accelerations that may typically be measured by such sensors when used in a sleep monitoring system may be in the sub-g range, e.g., 0.01 g.

The sleep monitoring sensor apparatus may be a discrete component or may be part of a larger system of components. For example, the sleep monitoring sensor apparatus may feature one or more cables that may be used to connect the sleep monitoring sensor apparatus to the sleep monitoring system. Such a cable or cables may constitute a communications interface that allows the sleep monitoring system to obtain data from the sensors in the sensor mesh. The cable or cables may be hard-wired into the sleep monitoring system, i.e., not designed to be easily disconnected, or may be connected to the sleep monitoring system by a connector to facilitate installation. In some implementations, there may be no physical connection between the sleep monitoring sensor apparatus and the sleep monitoring system. In such implementations, data from the sensor mesh may be communicated to the sleep monitoring system through, for example, a wireless communications link, such as a Bluetooth or 802.11 connection, or through one or more intermediary devices, e.g., through a network-connected server (such a communications link may, in this case, constitute a communications interface between the sleep monitoring sensor apparatus and the sleep monitoring system). The sleep monitoring sensor apparatus may be provided power from an external transformer that plugs into a standard electrical outlet, a replaceable or rechargeable battery or batteries, or the sleep monitoring system itself.

In some implementations, the sleep monitoring sensor apparatus may obtain measurements over a distributed area using other techniques. In some such implementations, distributed-area sensors may be used that do not necessarily give rise to a sensor-mesh arrangement as discussed herein. In such implementations, such sensors may be spatially segregated if used in a multi-sleeper context, e.g., each sleeper may have their own set of one or more distributed-area sensors and data from each set of one or more distributed-area sensors may be assumed to be attributable to one sleeper. Such implementations may still utilize a "carrier" or the like in order to position elements of the sensor system(s) used. It is to be understood that the various techniques for alarms and sleep monitoring discussed herein may also be implemented using such distributed-area sensor systems in place of the sensor mesh systems and related techniques discussed herein. For example, if two distributed area sensors are used (one on each side of a bed), then these may be used in place of, or in addition to, the sensor meshes discussed herein. In some implementations, the data from two such distributed-area sensors may be viewed as "global" sensor data, and data from each such distributed area sensor may be used to correct artifacts in the data from the other—for example, if one distributed sensor system indicates that a sleeper is restless, the motion data indicating this restless state may be used to adjust the data for the other sleeper in order to correct for any sympathetic movement in the second sleeper that is a reaction to the first sleeper's restlessness.

In some implementations, a pneumatic sensor system may be used to collect sleep data for a sleeper. In such implementations, the carrier may include one or more relatively thin, inflatable bladders that extend over one or more regions of the mattress. Such bladders may be constructed so as to be able to be pressurized to some degree with a fluid, such as air (or, if desired, an incompressible fluid such as water). The bladders may be connected with one or more pressure sensors, e.g., directly (e.g., when the pressure sensor is mounted within the inflatable volume of the bladder) or indirectly (e.g., when a bladder has a tube or other fluidic flow passage that connects a pressure port in the bladder with a pressure sensor located at some location outside of the bladder), that are configured to provide measurements of the pressure within the bladder. Thus, when an object, like a sleeper, lies on the bladder, the weight of the object may cause the bladder to compress the fluid and cause a pressure change within the bladder that may be measured by the pressure sensor. The amount of pressure change registered by the pressure sensor may, at least in part, be proportional or related to the amount of force that is applied to the bladder.

In such implementations, the amount of pressure or the time-varying amount of pressure change as measured by the pressure sensor may be monitored in order to determine various data points. For example, if there is a large change in the measured pressure (especially after relatively little or no change in pressure over an extended time period), e.g., a 50 mmHg spike in pressure, this may indicate that an object has been placed on the pressure sensor. If the pressure change is commensurate with a pressure change that may be expected when a person is lying on the bed, such a pressure change may be interpreted as indicating that a sleeper is present on the bed.

Other pressure data may also indicate the presence of a sleeper. For example, lower-magnitude pressure changes may also indicate the presence of a sleeper if their timing or other temporal characteristics are consistent with movement patterns of a sleeper. Thus, pneumatic sensor systems may be able to be used as sleeper presence systems that may indicate when a person is sleeping or lying on top of the inflatable bladder.

Figure 4:
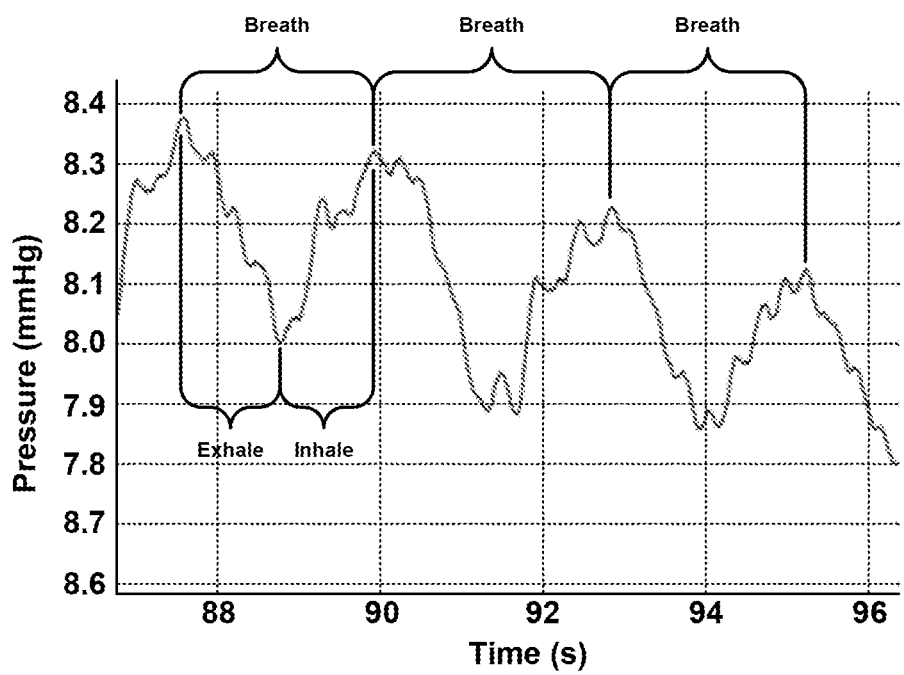
FIGS. 4 and 5 depict segments of pressure data time history for a pneumatic sensor system.
Figure 5:
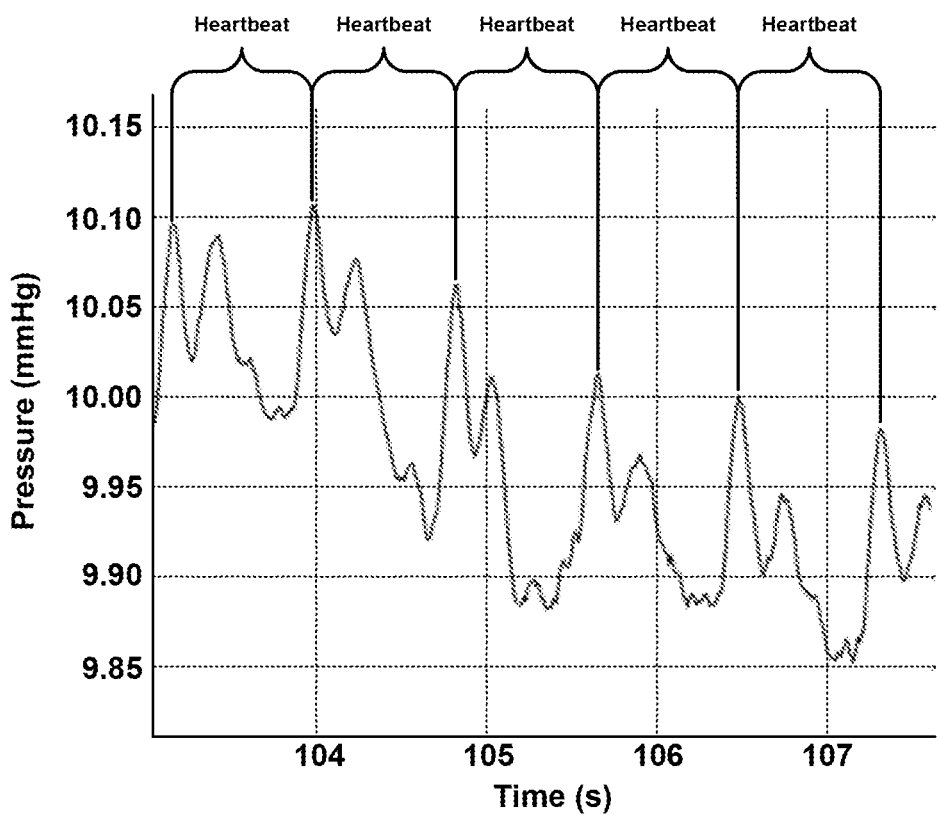

In addition to measuring pressure changes from "gross" movements, e.g., a sleeper getting on the bed, pneumatic sensor systems may also be used to collect much more nuanced physiological data, e.g., respiration rate and heart rate data. Compared to the movements that a person makes when getting into or out of bed, the movements that a person makes when lying still (due to respiration and heartbeat) are quite small, e.g., on the order of 0.2 mmHg to 0.5 mmHg for respiration-related movement and 0.05 mmHg to 0.15 mmHg for heartrate-related movement. Pressure sensors may be selected that may resolve such pressure changes, e.g., pressure sensors with accuracies on the order of ±0.01 mmHg, so that such respiration and heartrate data may be extracted from the pressure data. FIG. 4 depicts a segment of pressure data time history for a pneumatic sensor system; as can be seen, there is a pronounced periodic component to the pressure data that correlates with the respiration rate of the subject on the pneumatic sensor system from which the data was obtained. In this case, the respiration rate is on the order of 0.3 to 0.4 Hz. FIG. 5 also depicts a segment of pressure data time history for the pneumatic sensor system, but with a much narrower vertical axis range—as can be seen, there is also a periodic component to this data as well, which is, in this case, indicative of heart rate. In this example, the heartrate is about 0.7 Hz, which is consistent with an expected normal heartrate.

In some circumstances, data such as respiration rate may be obtained by detrending the data to eliminate, for example, pressure sensor data due to gross movement before performing other analysis, e.g., peak-counting analysis, to determine respiration rate. For example, the pressure sensor data could be subjected to a moving average filter and the resulting averaged signal may be subtracted from the raw signal, thereby leaving a signal that is dominated by the smaller-amplitude variations that were averaged out in the moving average processing. The amplitudes of these smaller-amplitude signals may be primarily driven by respiratory rate and a peak-counting algorithm may be used to identify each time a respiratory peak (breath) occurs. For heartrate related data, however, the ability to perform peak counting may be compromised since the magnitudes of the pressure signal that are attributable to heartrate-related movement may be relatively close to the noise amplitude of the pressure sensor. In such cases, or even more generally (for both respiratory and heartrate-related metrics), other analysis techniques may be used.

For example, the time-varying pressure signal may be analyzed using frequency-domain techniques, e.g., fast Fourier transforms or the like, in order to identify the dominant underlying frequencies in the pressure signal. The resulting dominant frequencies may then be analyzed to identify a dominant frequency or frequencies that have frequency and/or amplitude characteristics consistent with an expected range of respiration rates and/or pressure sensor amplitudes for a person. If multiple such frequency components are identified, then the frequency component that has the highest correlation with an expected respiration rate may be used, or, in some implementations, an average or other representative respiration rate may be determined based on such multiple frequency components. A similar process may be used to determine heartrate-related data, e.g., heartrate, heartrate variability, etc., although by identifying frequency components from the pressure sensor signal that correlate with expected heartrate-related parameters.

The pressure sensor signal quality for presence, motion, respiration, and heartrate-related data collection may be correlated with the absolute gauge pressure of the fluid within the bladder, i.e., the higher the absolute gauge pressure, the higher the signal quality. However, the more such a bladder is pressurized, the firmer it will be. Many sleepers may find such firmness uncomfortable, so in some implementations, the pressure that is maintained in such a bladder may be maintained within a predefined band of acceptable absolute gauge pressures, e.g., a band with a lowest absolute gauge pressure that produces a desired lower limit of signal quality level and a highest absolute gauge pressure that is set at a level that has been deemed to provide an acceptable level of comfort to the sleeper. In some implementations, one or both of these bounds may adjustable, e.g., automatically or via user-input. For example, if the sleep monitoring sensor apparatus, or a controller communicatively coupled thereto, determines that absolute gage pressures in the bladder that are higher than a particular value correlate with an increased level of user movement or restlessness, this may indicate that such firmer pressure settings are too uncomfortable and the controller may thus adjust the upper end of such an absolute gage pressure setting to a lower value. Similarly, if data quality at the lowest pressure setting is within acceptable bounds, the controller may adjust the lower bound of allowable absolute pressure in the bladder downwards. In some implementations, the user may be allowed to set the maximum allowable absolute pressure, e.g., the user may lie on the bladder while adjustments to the absolute gauge pressure are made and then indicate to the controller, e.g., by pushing a button or sending an input via a smartphone app or the like, when the bladder is at the limit of preferred firmness for that user; the absolute gauge pressure that correlates with that indicated firmness level may then be used as the upper limit.

In some implementations, the bladder may include a mechanism for allowing the absolute gage pressure to be lower than atmospheric pressure in the surrounding environment, thereby allowing the bladder to be very soft and comfortable to the user. For example, in some implementations the bladder may be filled with a compressible, porous material, such as elastomeric or other springy foam, that may be compressed and then spring back into its original shape. This material may be compressed by the weight a sleeper but may resist compression (or only permit a very small amount of compression, e.g., an order of magnitude or more less than the compression provided by a sleeper) due to atmospheric pressure on the bladder. Thus, even if the pressure in the bladder is reduced below atmospheric pressure, the bladder may still generally retain the overall shape that is provided by the porous material located inside the bladder.

Figure 6:
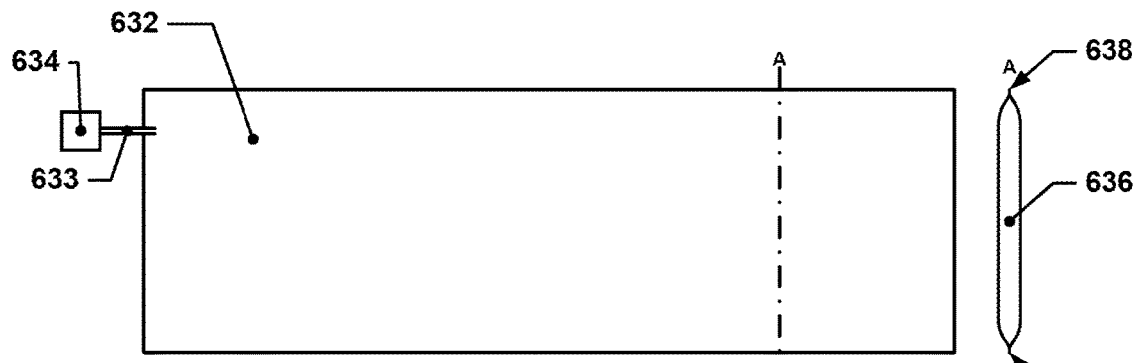
FIGS. 6, 7, 8, and 9 depict examples of pneumatic sensor systems that include a bladder.

The bladder element of the pneumatic pressure sensor system may be made from an airtight material, e.g., rubber-coated textiles or an elastomeric membrane, and may take a variety of forms. In some implementations, the bladder may have a single compartment, e.g., be sealed along its edges somewhat like a pillow case, with a pressure sensor mounted within the bladder's internal compartment or connected with it via a tube or other fluidic connection. For example, two layers of rubberized or polymer-backed fabric may be glued or otherwise bonded together along their common edges in order to form the bladder. FIG. 6 depicts an example of such a pneumatic sensor system, which may include a bladder 632, a pressure sensor 634, and a fluidic passage 633 that allows the pressure sensor 634 to obtain pressure measurements from the bladder 632. As can be seen from the cross-section supplied to the right of FIG. 6, the edges 638 of the two layers 635 that form the bladder 632 may be bonded together to form a free volume 636 within the bladder 632 that may be filled with fluid.

Figure 7:
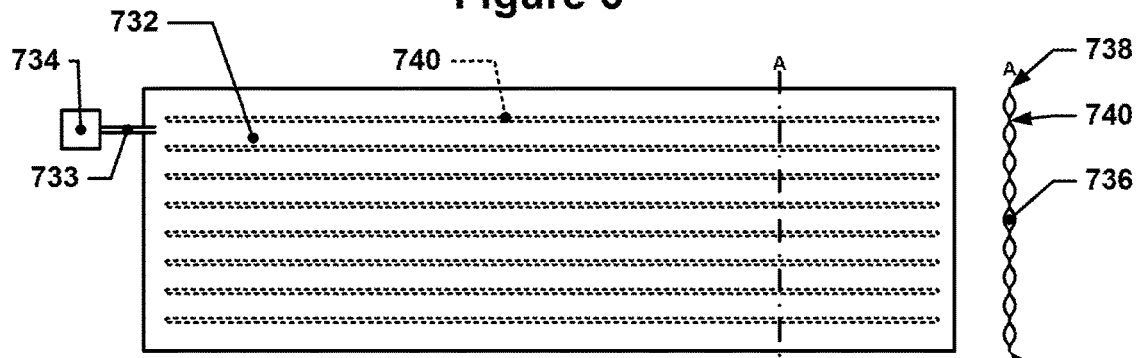

In some other implementations, the bladder may be formed by bonding or otherwise connecting two layers of rubberized fabric along their common edges and then also bonding, e.g., by heat welding or gluing, portions of the layers to each other along parallel linear paths, thereby forming a series of inflatable linear channels that are arrayed next to one another in a direction perpendicular to the channels' long axis. FIG. 7 depicts an example of a pneumatic sensor system that includes a bladder 732, a pressure sensor 734, and a fluidic passage 733, similar to equivalent such structures in FIG. 6. Also depicted in FIG. 7 are bonded segments 740, i.e., portions of the layers of the bladder 732 that are bonded together within the volume 736 of the bladder 732 that is formed by bonding the edges 738 of the bladder 732 together. In this case, the segments are linear segments that only slightly shorter than the overall length of the bladder 732, which results in the volume 740 of the bladder 732 being divided into a number of linear internal subvolumes, giving the bladder 7321 a corrugated appearance.

Figure 8:
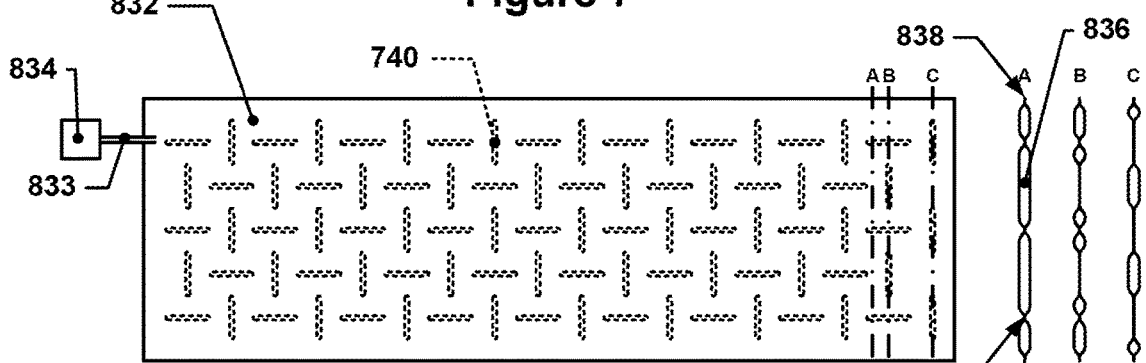

In yet another implementation, two layers of rubberized fabric may be bonded together along their common edges and then short linear segments of each layer in alternating orientations, separated by gaps along directions parallel to each segment, may be bonded together to form a series of contiguous, serpentine channels. FIG. 8 depicts an example of a pneumatic sensor system that includes a bladder 832, a pressure sensor 834, and a fluidic passage 833, similar to equivalent such structures in FIG. 6. Also depicted in FIG. 8 are bonded segments 840, which are bonded together as described above. This results in a more complex subdivision of the internal volume 840, as evidenced by the three different cross-sectional profiles shown.

Figure 9:
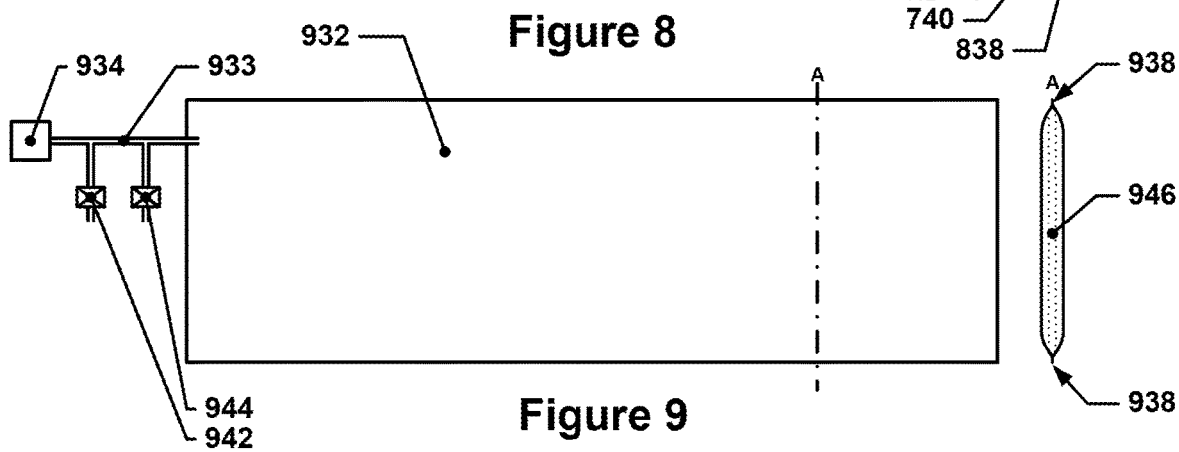

Such arrangements in which the bladder has internally bonded segments may serve to prevent the bladder from expanding in the z-axis (perpendicular to the average plane of the bladder) by more than a preset amount, e.g., 0.5 inches or between 0.5 inches to 3 inches. In the case of a bladder with an internal porous structure, e.g., a foam core, the internal porous structure may restrict the bladder from contracting too much in a direction parallel to the average plane of the bladder, which may, in turn, prevent the bladder from also expanding too much in the z-axis. In some implementations, the internal porous structure may be bonded to the bladder membrane layers to further prevent undesired expansion in the z-axis. FIG. 9 depicts an example of a pneumatic sensor system that has a bladder 932 with a compressible foam core 946 that is interposed between the layers that form the bladder 932 and that fills the volume within the bladder 932 that is formed by bonding together the edges 938.

In some implementations, a pneumatic sensor system may include one or more mechanisms for controlling the pressure within the bladder so that it remains within preset boundaries, e.g., such as between the maximum and minimum absolute gauge pressures discussed earlier. For example, in some implementations, the pneumatic sensor system may include an inlet check valve and an exhaust check valve, both of which may be fluidically connected with the internal volume of the bladder. FIG. 9 depicts one such arrangement (it is to be understood that any of the example bladder configurations discussed above with respect to FIGS. 6 through 8, as well as that depicted with respect to FIG. 9, may be used in any of the pressure control implementations discussed below. In FIG. 9, an inlet check valve 942 and an exhaust check valve 944 may be fluidically connected with the bladder 932. The exhaust check valve 944 may be configured to have a crack pressure (a check valve may typically only allow flow in a single direction, and may be configured to only permit flow in that direction when the pressure on the upstream side of the check valve reaches the "crack pressure" and causes the check valve to open and allow flow in the downstream direction) that is set to allow the exhaust check valve to open when the upstream pressure reaches the maximum desirable pressure in the bladder, and may be configured such that the upstream side of the exhaust check valve 944 is in fluidic communication with the bladder's interior volume and the downstream side of the exhaust check valve 944 is in fluidic communication with the ambient environment. Thus, if a sleeper lies on the bladder 932 and causes the pressure to increase beyond the maximum desirable pressure, the exhaust check valve 944 may crack open and allow the excess pressure to vent (once the pressure drops below the crack pressure, the check valve may re-seal and prevent further depressurization of the bladder). Conversely, the inlet check valve 942 may be oriented with the upstream side in fluidic communication with the ambient environment and the downstream side in fluidic communication with the interior of the bladder, and may have a crack pressure that is slightly lower than atmospheric pressure, e.g., 1 to 5 mmHg less than atmospheric pressure. This allows the bladder 932 to re-inflate once the sleeper gets up, ensuring that there will be adequate fluid volume in the bladder to allow compression of the bladder 932 to be detected.

In another implementation, the bladder may be fluidically connected with an external reservoir that is not in contact with the sleeper, e.g., the external reservoir may allow excess pressure from the bladder to be bled off into the reservoir, thereby potentially avoiding overpressurization scenarios. In some implementations, the reservoir may be made from an elastic material or may have an expandable internal volume that may pressurize the fluid that is forced into the reservoir to a pressure that is lower than the maximum desirable pressure so that the fluid that is moved into the reservoir will be moved back into the bladder once the pressure on the bladder that overpressurized the bladder is removed.

Figure 10:
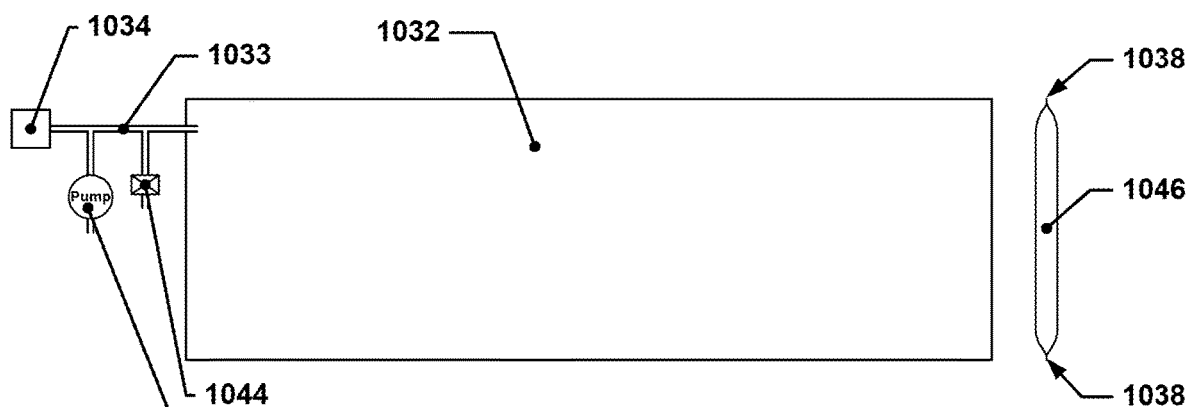
FIGS. 10 and 11 depict examples of pneumatic sensor systems that include a bladder and an active pressure control system.
Figure 11:
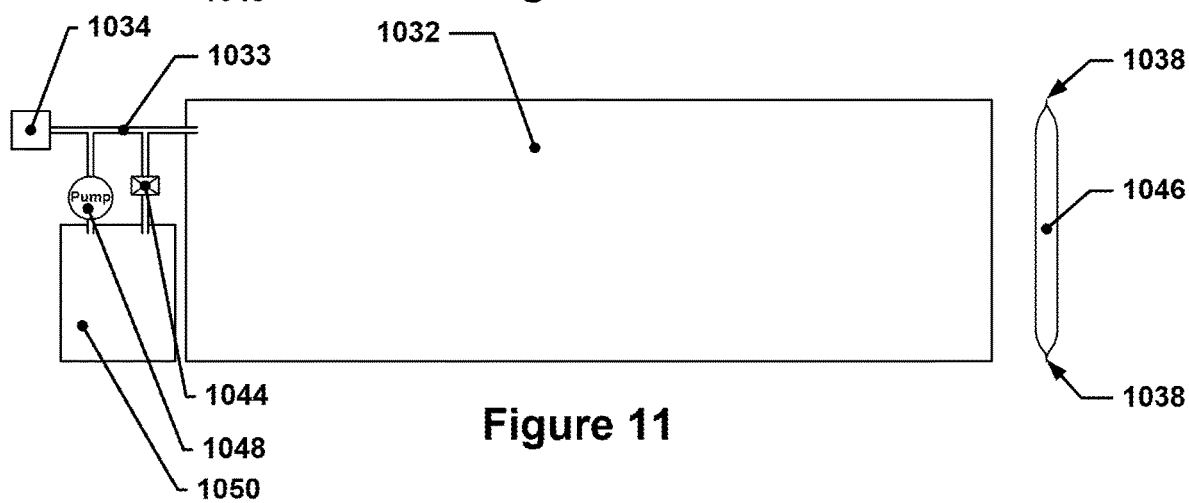

In other implementations, the pneumatic sensor system may include a pump and an exhaust valve that may be controlled by a controller. FIG. 10 depicts a pneumatic sensor system with a controllable pump and exhaust valve arrangement. In such implementations, the pump 1048 and the exhaust valve 1044 may be actively controlled by the controller (not shown) so as to maintain an average pressure in the bladder 1032 that is within predefined maximum and minimum absolute gauge pressures. Thus, if the average pressure in the bladder exceeds the desired maximum pressure in the bladder, the exhaust valve 1044 may be opened by the controller to bleed off the excess pressure. Similarly, when the average pressure in the bladder 1032 falls below the desired minimum pressure in the bladder 1032, the exhaust valve 1044, if not already closed, may be closed and the pump may be activated to re-pressurize the bladder 1032. In some implementations, the pump 1048 and the exhaust valve 1044 may communicate with the ambient environment, whereas in other implementations, such as is shown in FIG. 11, the pump 1048 and the exhaust valve 1044 may be connected with a reservoir 1050 instead of the ambient environment.

In such implementations, the maximum/minimum pressures limits used may vary depending on what use state the system is in. For example, if the system has determined that no person is on the mattress and is in a state where it may monitor continuously for the presence of a sleeper, i.e., an event in which a person lies down on the bed, the absolute gauge pressure may be set to be within 0.5 mmHg and 10 mmHg. After a sleeper presence has been detected, the absolute gauge pressure may be re-set to another range, e.g., 0.0 mmHg to 25 mmHg (for respiration rate detection) or 1 mmHg to 80 mmHg (for heartrate detection).

Figure 12:
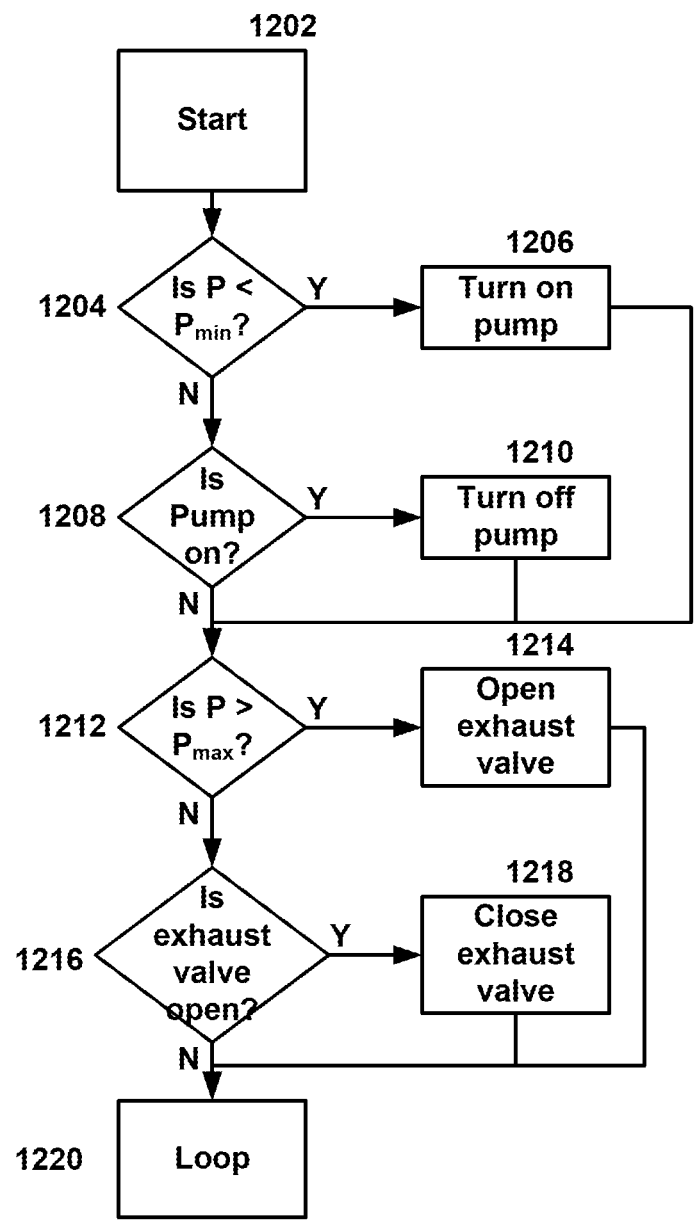
FIG. 12 depicts a flow diagram for an example active pressure control technique.

In implementations with a pump and valve arrangement, the controller may be configured to continuously or periodically monitor the pressure in the bladder and to take corrective actions as needed. FIG. 12 depicts a flow diagram for an example such technique. The technique may begin in block 1202 and proceed to block 1204, in which a determination may be made as to whether the bladder pressure is less than (or less than or equal to) a preset desirable minimum pressure. If the pressure is below the preset minimum pressure, then the technique may proceed to block 1206 in which the pump may be activated. If the pressure is not below the preset minimum pressure, then the technique may proceed to block 1208, in which a determination may be made as to whether the pump is on—if so, then the technique may proceed to block 1210, in which the pump may be turned off. Regardless of whether the pump is on or off, the technique may then proceed to block 1212, in which another determination may be made as to whether the pressure in the bladder is greater than (or greater than or equal to) the maximum desired pressure. If the pressure in the bladder is greater than the maximum desired pressure, then the technique may proceed to block 1214, in which the exhaust valve may be opened to bleed off the excess pressure before the technique proceeds to block 1220. If the pressure in the bladder is not greater than the maximum desired pressure, then the technique may proceed to block 1216, in which a determination may be made as to whether the exhaust valve is open—if so, then the technique may proceed to block 1218, in which the exhaust valve may be closed before proceeding to block 1220. If the exhaust valve is not open, then the technique may proceed to block 1220. From block 1220, the technique may return to block 1202, and so forth.

Figure 13:
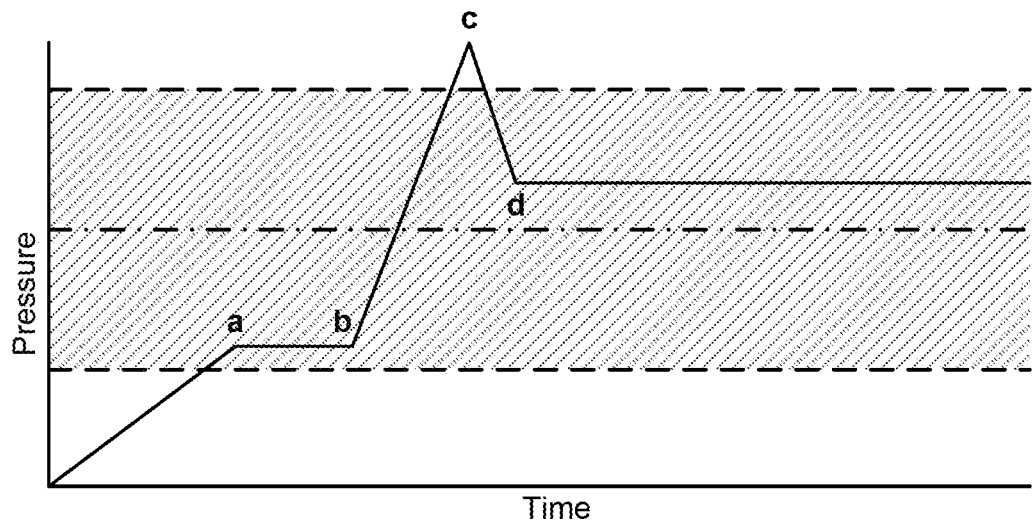
FIGS. 13 and 14 depict pressure/time diagrams for an example pneumatic sensor system during transitions between various states.

FIG. 13 depicts a pressure/time diagram for an example pneumatic sensor system during transitions between various states. For example, at t=0, the pump may be activated to start pressurizing the bladder, e.g., when the unit is initially powered up. At t=a, the pump may be turned off since the pressure may be within the preset desired pressure limits. At t=b, a person may start to lie down on the bed, causing the pressure in the bladder to rise, ultimately rising above the present maximum pressure at t=c, at which point the exhaust valve may be opened to allow the overpressure to vent. After the pressure has decreased below the present maximum pressure, the exhaust valve may be closed again at time t=d. In some implementations, the exhaust valve closure may be timed to coincide with the point where the pressure within the bladder is near the mid-point between the preset minimum and maximum pressures.

Figure 14:
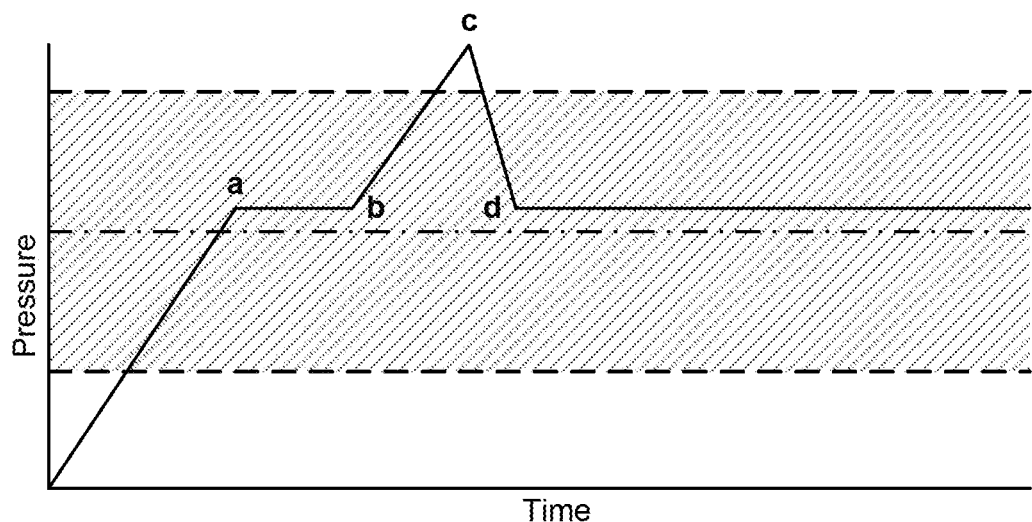

FIG. 14 depicts another pressure/time diagram for the example pneumatic sensor system during other transitions between various states. For example, at time t=0, the pump may be activated to start pressurizing the bladder, e.g., when the unit is initially powered up. At t=a, the pump may be turned off since the pressure may be approximately midway between the preset minimum and maximum desired pressure limits. At t=b, a person may start to lie down on the bed, causing the pressure in the bladder to rise, ultimately rising above the present maximum pressure at t=c, at which point the exhaust valve may be opened to allow the overpressure to vent. After the pressure has decreased below the present maximum pressure, the exhaust valve may be closed again at time t=d, e.g., when the pressure within the bladder is near the mid-point between the preset minimum and maximum pressures.

In pneumatic sensor systems in which the pressure within the bladder may be actively controlled, such as in such systems having a pump and valve arrangement as discussed above, the controller for such pneumatic sensor systems may also be configured to control the bladder pressure so that various other functionalities may be provided. For example, through actively controlling the bladder pressure, such controllers may cause the bladder pressure to be varied over time so as to either wake a sleeper up or, in some alternative or additional implementations, encourage the sleeper to fall asleep.

Figure 15:
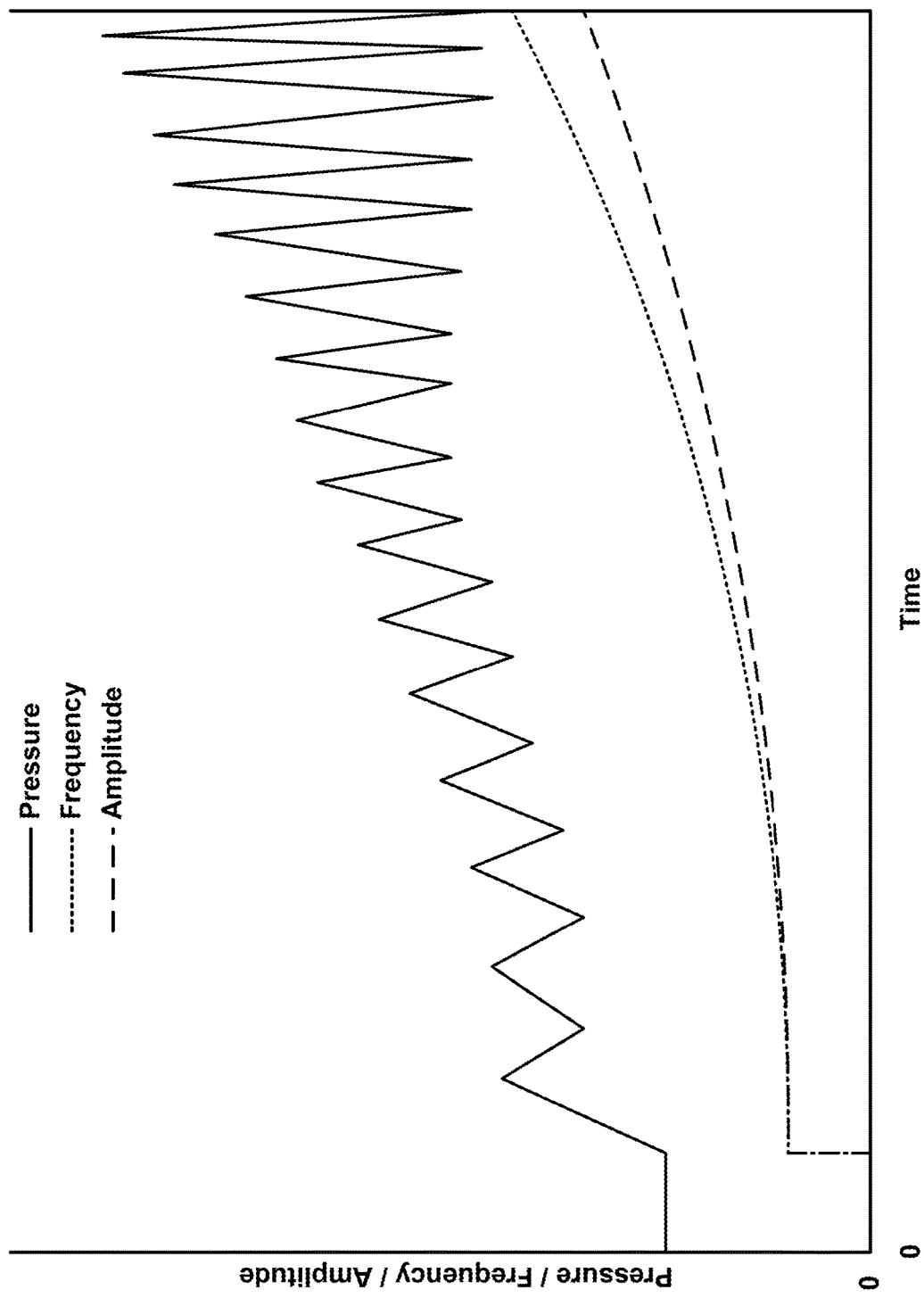
FIG. 15 depicts pressure, frequency, and amplitude parameters for an example pneumatic wake-up alarm system.

For example, if it is desired to wake a sleeper, such as is discussed later in this disclosure, the bladder may be pressurized and depressurized repeatedly using the pump and valve, in some cases while slowly increasing the average pressure of the bladder, such as is shown in FIG. 15. In FIG. 15, the pressure in the bladder (solid line) may be increased/decreased according to one or both of a rising pressurization/depressurization cycle frequency (dotted line) and amplitude (dashed line) (where the amplitude indicates the pressure difference between successive maximum/minimum peaks in the bladder pressure). In some implementations, only one of the frequency and amplitude may be varied for such an alarm.

Figure 16:
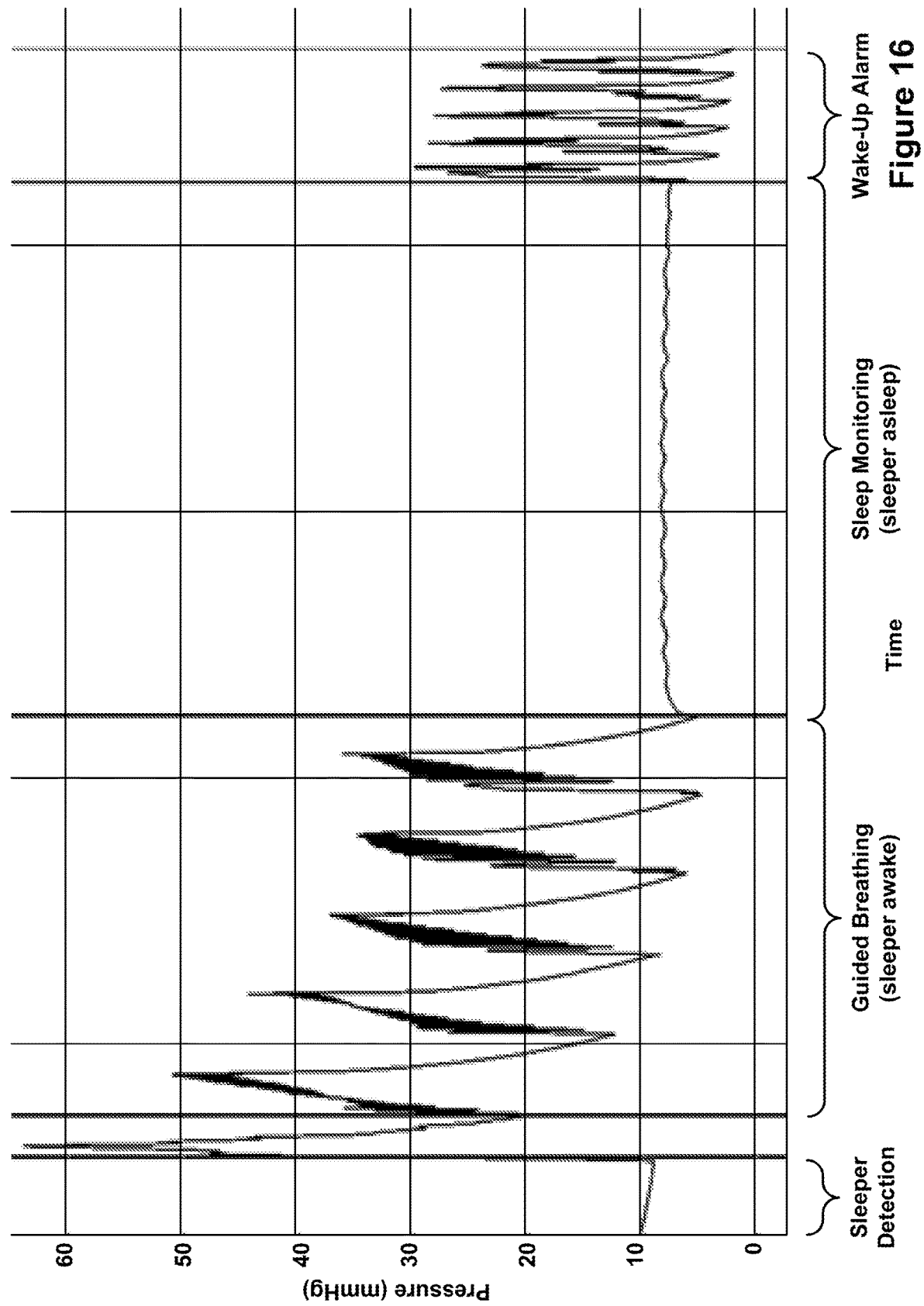
FIG. 16 depicts an example pressure history indicating an example guided breathing technique.

For implementations in which the pneumatic sensor system is configured to encourage sleep, the controller may monitor the pneumatic sensor system to identify when a sleeper lies down on the mattress, at which point the controller may monitor the pressure data from the pneumatic sensor system for the sleeper for a period of time, e.g., 15 seconds, 30 seconds, or one or several minutes, in order to established the sleeper's respiratory rate. After establishing the sleeper's respiratory rate, the controller may start to pressurize and depressurize the bladder in synchronicity with the sleeper's inhalations and exhalations, e.g., when the person is inhaling, the controller may cause the bladder pressure to increase; when the person is exhaling, the controller may cause the bladder pressure to decrease. In some such implementations, if the person pauses between inhalations and exhalations, the bladder pressure may be kept constant by the controller. After a period of time during which the pressurization/depressurization of the bladder is synchronized with the sleeper's breathing cycles, the controller may slowly adjust the periodicity of the pressurization/depressurization cycles so that each such cycle takes a longer and longer period of time (or so that the cycle duration for sets of pressurization/depressurization cycles slowly increases, e.g., 5 cycles at duration X, followed by 5 cycles of duration X+Y, and so on). This adjustment may occur over a span of 2 to 30 minutes of time and at a rate that results, for example, in a cycle frequency of 0.1 Hz, or some other frequency that is representative of a person's typical sleeping respiration rate. A person's body, when exposed to such stimuli, may have a sympathetic response to the pressurization/depressurization behavior of the bladder, and the sleeper may subconsciously or consciously start to synchronize their breathing with the pressurization/depressurization of the bladder. Thus, slowing the pressurization/depressurization rate of the bladder may cause the sleeper to subconsciously or consciously slow their breathing rate as well, which may encourage the sleeper's transition to a light sleep state. This adjustment of pressurization/depressurization cycles, which may be referred to as "guided breathing," may persist for a fixed period of time, until the sleeper moves significantly or gets up, or until the sleeper appears to have fallen asleep, e.g., as indicated by a lack of movement, a respiratory rate associated with sleep, or other indicators. FIG. 16 depicts an example pressure history indicating such a technique (although FIG. 16 is not at all to scale in the time axis). In FIG. 16, a first interval may include a sleeper detection event, e.g., a large pressure spike (in this case, +50 mmHg), after which a period of guided breathing may be provided. During guided breathing, the pressure in the bladder may be cyclically raised/lowered by a significant amount since the purpose of such pressurization/depressurization is to produce a perceptible prompt or cue to the sleeper's body. In this case, only 5 pressurization/depressurization cycles are performed, but in actual practice, far more may be performed, depending on the circumstances. After the sleeper falls asleep, then monitoring of the sleeper's physiological state may occur while keeping the pressure in the bladder at a relatively low and relatively constant level (the slight variations in the pressure that are visible in this sleep monitoring phase are due, for example, to the physiological effects that are being monitored, e.g., pressure fluctuations due to respiration). At a particular time, an alarm may be provided, as discussed above, in order to wake the sleeper.

Figure 17:
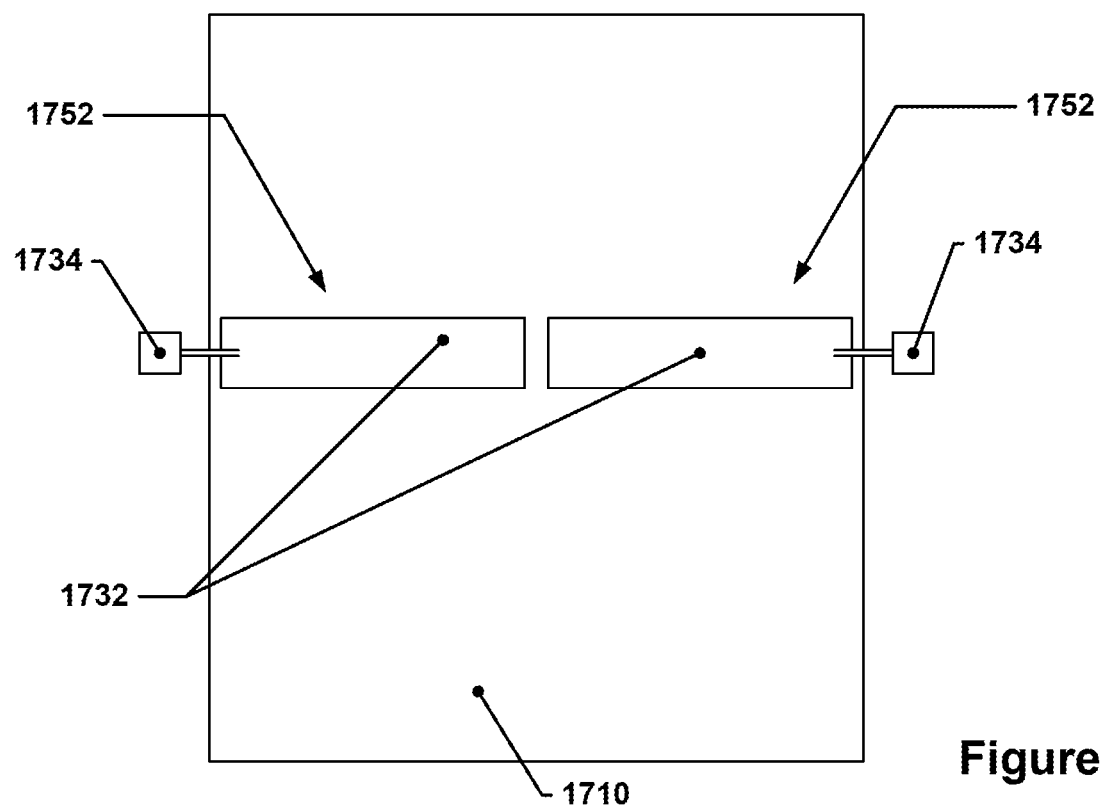
FIG. 17 depicts an example arrangement for a two-sleeper arrangement of pneumatic sensor systems.

Pneumatic sensor systems may, as indicated earlier, be used to monitor multiple sleepers in a bed. In such implementations, a separate bladder/pressure sensor system may be arranged on the carrier so that each is positioned on a different half of the mattress, e.g., one on the left side of the mattress and the other on the right. The pressure sensors for each may be located on opposing sides of the mattress, e.g., near their respective bladders. In some implementations, the pressure sensors may be on the same side of the mattress, and the carrier may have a tube or other pressure-conveying passage that extends from the far bladder, across the carrier, and to one of the pressure sensors. FIG. 17 depicts an example arrangement for a two-sleeper arrangement of pneumatic sensor systems 1752 in which a mattress 1710 has two bladders 1732 positioned on it, each of which is connected via a fluidic passage to a separate pressure sensor 1734.

Another type of distributed-area sensor that may be used is an optical fiber-based sensor system. In a optical fiber-based system, pressure or force applied to an optical fiber, e.g., such as may be caused by the weight of a sleeper or by movements of the sleeper, may cause a measurable change in the optical characteristics of the optical fiber. These changes in the optical characteristics may be quantified in order to obtain data indicative of the timing and magnitude of such movements or force/pressure applications.

In some implementations, light may be transmitted from one end of an optical fiber to the other end of that optical fiber with the optical fiber being routed through an area of interest on a carrier. A large percentage of the light that is introduced into the receiving end of the optical fiber may be received at the receiving end of the optical fiber (also referred to herein simply as a "fiber") due to total internal reflection (TIR). However, if the fiber is bent, e.g., through the application of external forces, this may increase the amount of light that is lost instead of being internally reflected, thereby decreasing or attenuating the amount of light that is received at the receiving end of the optical fiber. The amount of light that is attenuated may be dependent on the number of fiber deflections and the degree of each of those deflections. By measuring the variation in the amount of light that is transmitted through a fiber over time using a photodetector or other light-sensing sensor, a measurement may be obtained that may represent or correlate with the magnitudes of deflections experienced by the optical fiber.

Optical fibers may offer an inexpensive, waterproof, low-noise, and easily-integrated mechanism for measuring movement and force/pressure exerted on a mattress (or other item, e.g., a pillow) by a sleeper.

In some implementations, the optical fibers may be interposed between, or placed adjacent to, microbending structures that are engineered to provide discontinuities that are adjacent to the fibers and may amplify fiber bending when pressure is applied to the fibers. For example, in some implementations, the fiber may be configured to follow a meandering, e.g., serpentine or looping, path that causes the fiber to be distributed across a large area, e.g., an area several feet long and two to three feet wide. The fiber may be sandwiched between two grids or coarse-pitch meshes of fibers. The mesh fibers may, for example, also be optical fibers or may be non-optically-transmissive fibers; in the former case, the mesh optical fibers may, if desired, be disconnected from any light sources since they are being used for their mechanical properties rather than for their optical transmission properties. Generally speaking, the mesh fibers may be of the same or greater stiffness as the optical fibers through which the light is directed for measurement purposes.

Figure 18:
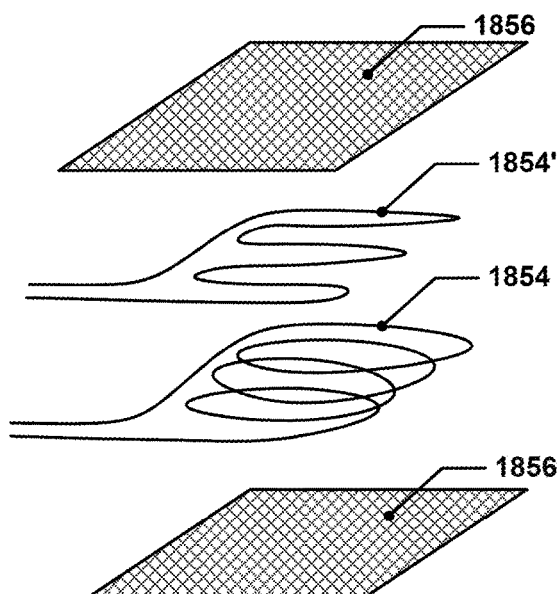
FIG. 18 is an exploded view of one example optical fiber-based sensor system.

FIG. 18 is an exploded view of one example optical fiber-based sensor system in which an optical fiber, e.g., optical fiber 1854 or 1854', is routed over a large area, e.g., a carrier, such as a mattress pad. In the case of the optical fiber 1854, the optical fiber 1854 follows a meandering serpentine path that does not cross over itself. In other implementations, such as those using a configuration like optical fiber 1854', the optical fiber 1854' may cross over itself multiple times, e.g., such as may occur when the optical fiber 1854' forms several loops that overlap each other. In FIG. 18, the optical fiber 1854 or 1854' is sandwiched between two microbending elements or structures, e.g., fiber meshes, 1856. It is to be understood that the ends of such optical fibers may be connected to light emitter/detector units, e.g., devices that may have a light source configured to introduce light of one or more wavelengths into one end of the optical fiber and one or more detectors configured to measure the amount of light that is emitted from the other end of the fiber (these units are not shown, but would be used in any of the implementations discussed herein—for simplicity, the optical fibers are generally shown with two free ends—one of which would be interfaced with a light source and the other of which would be interfaced with a light detector).

Figure 19:
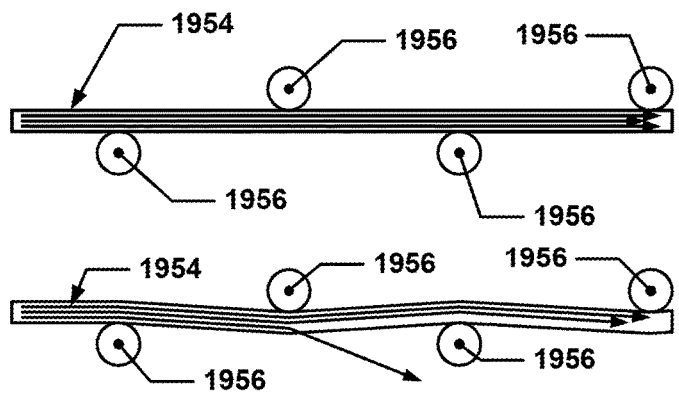
FIG. 19 depicts a cross-sectional view of fiber deflection in an optical fiber-based sensor system.

When a load is placed on the mesh that is interposed between the load and the mesh, the load will press that mesh into the optical fiber, causing small, localized deflections in the optical fiber that may attenuate the light that travels along the fiber. If meshes are used on both sides of the optical fiber, then the optical fiber, in turn, may be pressed into the mesh that is on the opposite side of the optical fiber from the load, resulting in additional deflections of the optical fiber and increased light attenuation. FIG. 19 depicts a cross-sectional view of such deflection—in the upper depicted embodiment, a fiber 1954 passes between two mesh layers 1956 and 1956'; in the lower depiction of that embodiment, the upper mesh layer 1956 has been compressed into the optical fiber 1954 and the lower mesh layer 1956', causing the optical fiber 1954 to flex and bend. This results in the amount of light that travels completely through the optical fiber 1954 (indicated by arrows in FIG. 19) to be attenuated since some of the light will exit the waveguide formed by the optical fiber (such as the arrow indicating light that has exited the optical fiber 1954).

Figure 20:
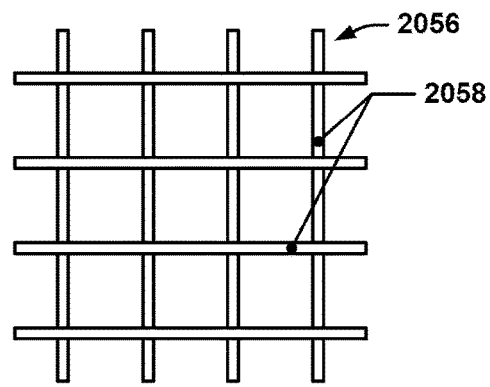
FIGS. 20 and 21 depict example portions of a microbending structure or mesh.
Figure 21:
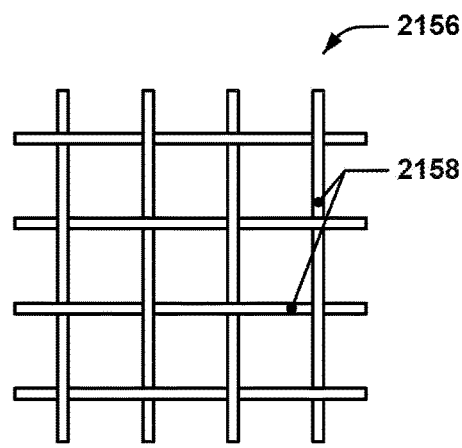

As discussed, the microbending structures may, for example, be a grid or mesh of fibers in some implementations. FIGS. 20 and 21 depict example portions of a microbending structure or mesh. In FIG. 20, the mesh is formed by overlaying two linear arrays of fibers over one another with the fibers of one layer being orthogonal to the fibers of the other layer. It is to be understood that any of a number of different arrangements of such mesh fibers may be used and is not limited to square mesh patterns. In FIG. 21, the mesh is a woven mesh, with each fiber alternating along its length with regard to whether it passes over or under the fibers that it crosses over.

Figure 22:
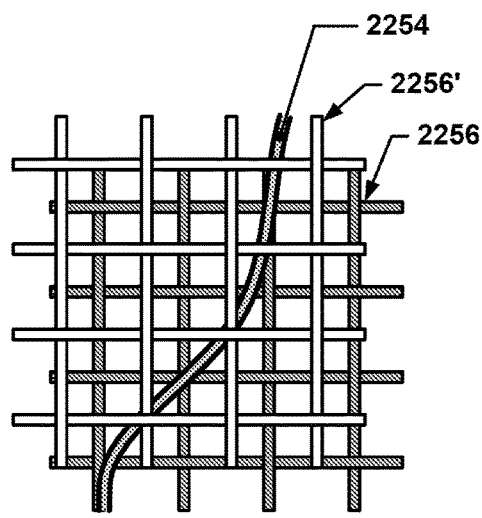
FIG. 22 depicts an example of an offset arrangement for microbending structures.

In some implementations, the grids/meshes on opposing sides of the optical fiber may be offset from one another in the mesh/grid plane so that the fibers in one grid/mesh do not exactly align with the fibers in the other grid/mesh. Such arrangements may promote increased flexing/bending of the optical fiber in response to pressure applied on the mesh/fiber stack, resulting in more attenuation of the light transmitted through the optical fiber and thus an enhanced signal quality. FIG. 22 depicts an example of such an offset arrangement, with microbending structure/mesh 2256 being offset in the X- and Y-directions by approximately 50% of the pitch between fibers in the microbending structure/mesh 2256 from the microbending structure/mesh 2256'. An optical fiber 2254 can be seen interposed between the microbending structures/meshes 2256 and 2256'

Figure 23:
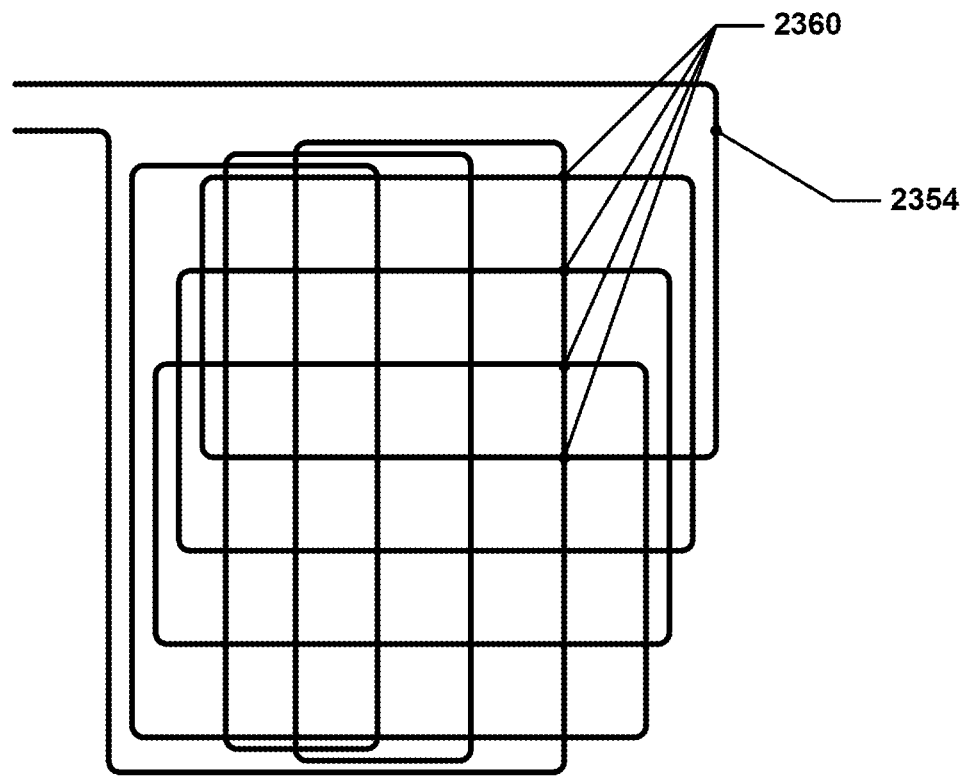
FIG. 23 depicts a schematic of an optical fiber routing that may create its own microbending structures by virtue of it overlapping itself.

In some implementations, the optical fiber itself may be woven into a mesh with the optical fiber crossing over itself in numerous locations. In such implementations, a separate mesh on one or both sides of the optical fiber may be unnecessary, as the optical fiber may press into itself at the cross-over points, thereby providing the localized deflections discussed earlier. FIG. 23 depicts a schematic of an optical fiber routing that may create its own microbending structures by virtue of it overlapping itself. The optical fiber 2354 may follow a looping path that crosses over itself in multiple locations, e.g., crossovers 2360. Each crossover point may provide a localized bending location that may act in a manner similar to the mesh fibers discussed earlier.

Figure 24:
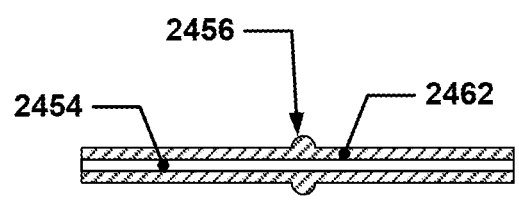
FIG. 24 depicts a cross-sectional view of an optical fiber with an integrated microbending structure.

In some implementations, microbending structures may be integrated into the optical fiber itself. FIG. 24 depicts a cross-sectional view of an optical fiber with an integrated microbending structure. Most optical fibers are clad in a cladding, e.g., glasses, doped glasses, plastics, acrylics, fluoropolymer polycarbonate, etc., that may protect the optical fiber core (which may be glass or plastic such as PMMA, silicone, etc.) from damage and may increase the total internal reflectance characteristics of the optical fiber. In some implementations, the cladding may be modified so as to include microbending structures as part of the cladding. For example, in the example of FIG. 24, the optical fiber 2454 is clad in cladding 2462 that includes a circumferential rib or expanded diameter section that acts as a microbending element 2456.

Figure 25:
FIG. 25 depicts another cross-sectional via of an optical fiber with integrated microbending features.

FIG. 25 depicts another cross-sectional via of an optical fiber with integrated microbending features. In FIG. 25, the cladding 2562 of the optical fiber 2554 is formed of a variable-stiffness material such that the more densely cross-hatched area is stiffer than the less densely cross-hatched area. Thus, then the optical fiber is compressed, the optical fiber will tend to bend at the location where the stiffer material is more prevalent.

In some other implementations, another fiber or filament may be wrapped around the exterior of an optical fiber, e.g., to form a helical winding, in order to form a microbending feature—the wound filament may form a continuous, helical rib—somewhat like the threads on a screw—that travels around the outer circumference of the optical fiber to provide a microbending feature. In implementations where the microbending features are located on the fiber itself, there may, in some cases, also be a flat, somewhat stiff material placed next to the optical fiber to allow the load that is applied to that material to be transferred to the optical fibers.

In some implementations, the optical fiber itself may be modified at various locations along its length, i.e., the optical fiber may not be continuous along its entire length or may not have homogenous material properties along its entire length, in order to provide location-specific sensitivity to movement or pressure.

For example, in some configurations, an optical fiber may be modified so that there are fiber Bragg gratings (referred to herein as "Bragg gratings") positioned at one or more locations along the optical fiber's length. A Bragg grating may be formed by modifying the optical fiber core's refractive index in a periodic fashion along the length of the fiber at each Bragg grating location. A Bragg grating may thus act as an optical filter that reflects a particular wavelength or wavelengths of light back towards the light source; the specific reflectance characteristics are determined by the properties of the Bragg grating. If an optical fiber having a Bragg grating is flexed or otherwise strained, the strain induced in the optical fiber will cause the Bragg grating located therein to also experience a dimensional change that will alter the reflectance properties of the Bragg grating, causing the reflected light to change wavelength. By measuring the wavelength of light that is reflected back through the optical fiber from a given Bragg grating, it is possible to quantify the amount of strain experienced by the optical fiber at the location of the Bragg grating. In some implementations, multiple Bragg gratings may be used in the same optical fiber, with each configured to reflect a different wavelength of light. By monitoring the wavelengths of light that are reflected back, and the degree to which they deviate from the default wavelengths that the multiple Bragg gratings normally reflect, determinations may be made as to how much each Bragg grating has been deformed or flexed. Such systems may allow not only for information on overall distributed movement and pressure to be obtained, but may also allow location-specific measurements to be made. For example, data from Bragg gratings located in a region of the carrier where the sleeper's chest may be may be used to determine heart rate, whereas data from Bragg gratings lower down on the carrier, e.g., where a sleeper's legs may normally be, may be used to determine non-heartrate-related metrics, e.g., gross movement, restlessness, etc.

In some implementations, the optical fiber may actually be severed such that there is a discontinuity in the optical fiber. In such arrangements, the severed ends of the optical fiber may be aligned with one another and supported by a mechanical support, e.g., a semi-flexible sleeve or coupler, that may align the severed ends of two adjacent optical fiber segments so that light traveling down one of the optical fibers may still generally pass into the adjacent and connected optical fiber when the ends of the segments are aligned. However, when an optical fiber segment is subjected to force or displacement, this may cause the end or ends of the adjacent optical fiber segment or segments to displace, e.g., by linear translation in a direction perpendicular to the centerlines of the optical fibers at the fiber ends, by rotation of the ends of the optical fiber segments relative to each other about an axis that is perpendicular to the long axis of the optical fiber segments at the fiber ends, or a combination of such displacements.

Figure 26:
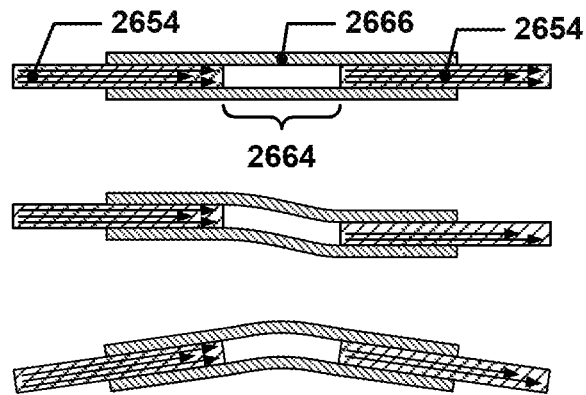
FIG. 26 depicts an example of a discontinuity-based optical sensor.
Figure 27:
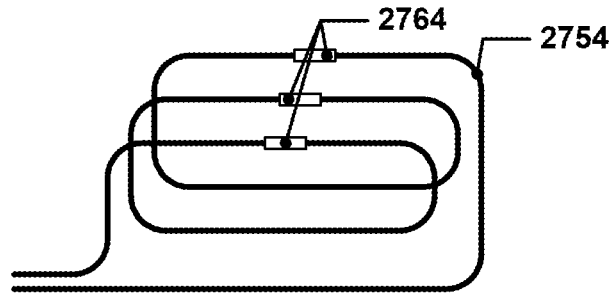
FIG. 27 depicts a diagram of an optical fiber-based sensor system using discontinuity-based sensors.

For example, FIG. 26 depicts an example of such a discontinuity-based optical sensor. In such an implementation, the optical fiber 2654 may be severed (and the severed ends polished/lapped to promote optical transmission through the severed ends) and the two severed ends may be separated by a fiber break or gap 2664. The two severed ends may be supported relative to each other by a fiber support 2666, which, in this case, is a flexible tube that may, when exposed to little or no external force, align the severed ends such that light may be transmitted between them with little or no loss. However, when the severed ends are displaced relative to one another, as is shown in the lower two examples in FIG. 26, the amount of light that passes through the fiber break and re-enters one of severed ends may be decreased, thus attenuating the signal. This signal attenuation may be measured and used in the same way that the signal attenuation in the earlier-discussed optical fiber-based sensor systems is used. Such optical fiber break sensors may be located at one or more locations along a fiber, e.g., such as is shown in FIG. 27.

Figure 28:
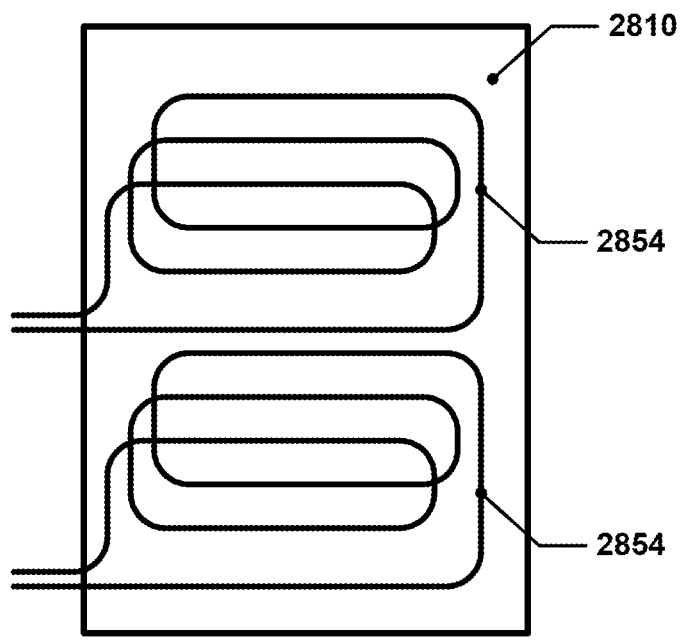
FIG. 28 depicts an optical fiber-based sensor system with multiple optical fibers.

As discussed earlier, multiple optical fiber sensor systems may be used in a common carrier, e.g., to monitor different regions of a mattress to obtain data for different sleepers (in which case they may be located on opposing left/right sides of the mattress) and/or to obtain data on from different areas of a person's body (in which case there may be one optical fiber that is located in a region near where a sleeper's chest might be, and another near where the sleeper's legs may be, and so forth). FIG. 28 depicts one example of such a system (for a single sleeper) in which there are two separate optical fibers 2854 arranged on a mattress 2810.

It is also to be understood that the optical fiber-based systems discussed herein may also be implemented in a carrier that acts as a pillow case (or that is designed and sized so as to be insertable into a pillow case). During tests performed with an optical fiber sensor system, e.g., the optical fiber sensors systems that detect micro- and macro-bending of the optical fiber based on the amount of light attenuation, it was found that placement of such an optical sensor system resulted in the successful collection of both respiratory and heart-rate-related data for test subjects, regardless of whether the optical fiber sensor/carrier was placed on the top side of the pillow or on the bottom side of the pillow (although the data collected from the bottom side of the pillow exhibited slightly greater noise, the peaks identifying individual respirations and heartbeats were still clearly identifiable). In some such implementations, the carrier may be sized to be smaller than a standard pillow size so that it does not extend past the edges of the pillow.

Figure 29:
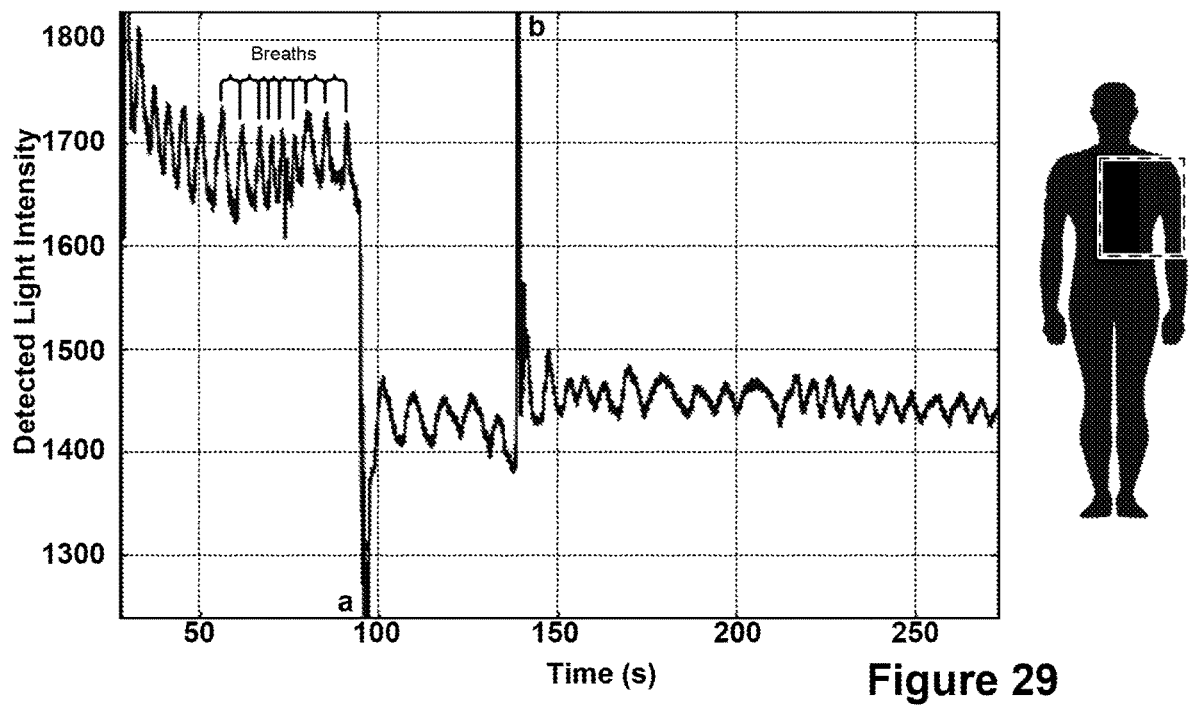
FIGS. 29 and 30 depict example data collected from an optical fiber sensing system.
Figure 30:
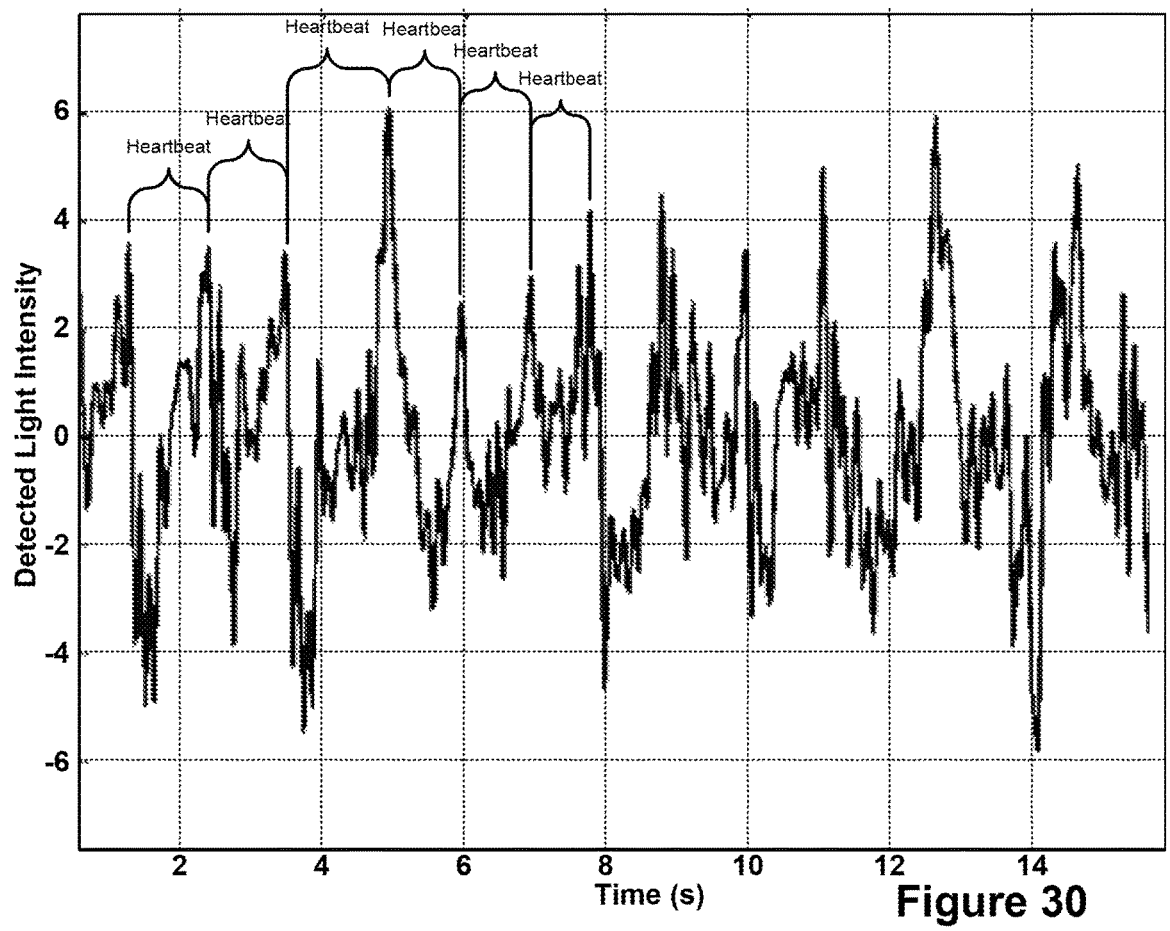

FIG. 29 depicts example data collected from an optical fiber sensing system—as can be seen, the data clearly exhibits a periodic component (the numerous smaller peaks (between about 6 and 10 peaks per 50 second interval) that correlates well with typical respiratory rates. Unlike in pneumatic sensor systems where measured quantity is air pressure (which will tend to equalize throughout the bladder and thus be less sensitive to the exact distribution of pressure or force on the bladder), the measured quantity in an optical fiber sensor system is light and is constrained to the optical fiber path-thus, if the sleeper shifts so that they are pressing on less optical fiber, they will cause a corresponding decrease in attenuation (and vice versa). Points "a" and "b" in FIG. 29 represent points in time at which the sleeper made a large movement—after the movement at "a", the sleeper was in a position that resulted in more light attenuation than before, whereas after the movement at "b", the sleeper was in much the same position as before. The data in FIG. 29 was collected from an optical fiber sensor that was routed through a rectangular region just under the sleeper's chest area, as shown by the dashed rectangle over the silhouette of a person to the right of the graph. FIG. 30 depicts a similar plot, but showing heart rate data (this data has been post-processed to remove lower-frequency components, such as respiratory data, generally leaving the heart rate components as the dominant data)—as can be seen, the heart rate may be clearly identified by the peaks that are evident.

Alarm System

In some implementations, the sleep monitoring sensor apparatus may also include one or more alarms that are also positioned on the carrier, which may be referred to herein as a wake-up alarm system (although such alarms may also be used for other purposes besides waking people up, as will be discussed further herein); the wake-up alarm system may typically be integrated into the sleep monitoring sensor apparatus, and the control of the alarms in the wake-up alarm system may be provided, for example, by the same hardware that provides sleep monitoring system functionality and/or sleeper presence monitoring functionality and/or sleeper identification functionality (see, for example, FIG. 53, discussed later herein). In the case of a sleep monitoring sensor apparatus that is designed to be used with mattresses sized for two people, there may be at least two alarms arranged such that each alarm is localized to one side of the mattress or the other, e.g., such that a person sleeping on one side of the mattress will generally perceive one alarm to a much greater extent than the other alarm, and a person sleeping on the other side of the mattress will perceive the other alarm to a much greater extent than the first alarm. Such alarms may be audible alarms, e.g., piezoelectric or non-piezoelectric speakers, or haptic devices, such as eccentric rotating masses (ERMs) or linear resonant actuators (LRAs) (the Pico Vibe™ ERM or the Precision Haptic™ LRA product lines offered by Precision Microdrives (www-.precisionmicrodrives.com) are some examples of haptic devices that may be used to provide alarm functionality in the sleep monitoring sensor apparatus).

Figure 31:
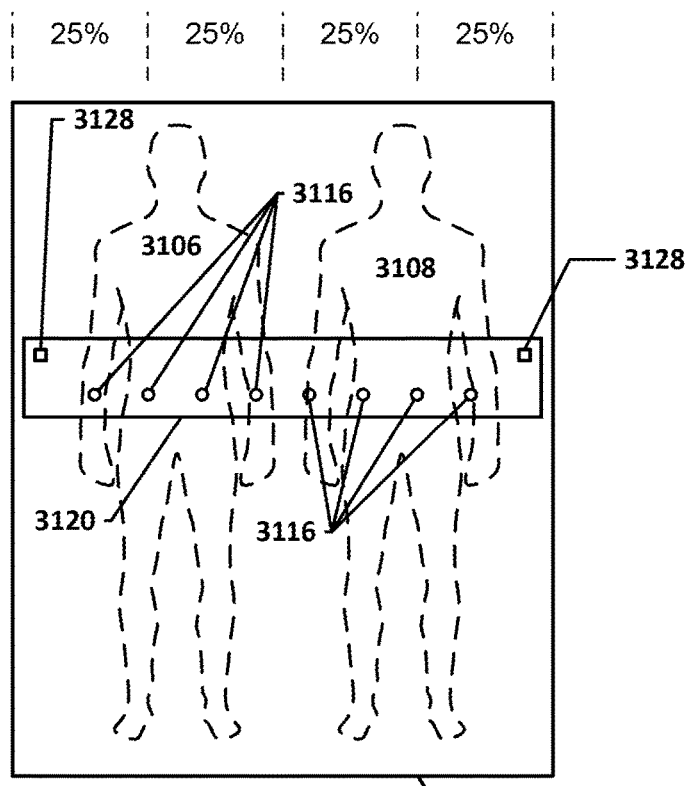
FIG. 31 depicts an example wake-up alarm system.

FIG. 31 depicts an example wake-up alarm system. In FIG. 31, the wake-up alarm system includes a carrier 3120 that includes a plurality of sensors 3116, which may be part of a sleep monitoring system and/or sleeper identification system, as discussed elsewhere herein. These sensors 3116 may be distributed across the carrier 3120, e.g., to form a sensor mesh as discussed earlier in this paper. The carrier 3120 may also include alarms 3128 that are located on the carrier such that noise or vibration from each alarm 3128 originates from a location within a different half of the mattress 3110 (division marks at the top of the mattress 3110 divide the mattress up into quartiles for reference). The carrier 3120 may act to position the alarms 3128 (and the sensors 3116) on the mattress 3110 in desired locations, and may be similar to the carriers discussed earlier with respect to the sleep monitoring sensor apparatuses discussed earlier herein. In the depicted implementation, one alarm 3128 is located along the left side of the mattress 3110 in a position that is to one side of where a first person 3106 may lie on the mattress 3110, and the other alarm 3128 is located along the right side of the mattress 3110 in a position that is on the other side of where a second person 3108 may lie on the mattress 3110 from the first person 3106. Thus, sound or vibrations emitted by the alarms 3128 may be damped out or lessened as they transit through the space occupied by the closer of the two people 3106 and 3108 before they reach the further of the two people 3106 and 3108, thereby allowing for more targeted alarm activation, e.g., waking the first person 3106 with a significantly reduced chance of also waking the second person 3108, or vice versa. This allows for user-specific alarms to be independently set and provided, allowing each person to maintain their own sleep/wake schedule.

In the depicted example, the carrier 3120 is a narrow strip that is approximately as long as the mattress 3110 is wide. The carrier 3120 may take a variety of other shapes and forms as well, as is illustrated in FIGS. 32 through 35. In some implementations, the carrier 3120 may have straps, clips, or other devices attached to it that allow the carrier to be secured to the mattress 3120. In other implementations, as discussed earlier with respect to sleep monitoring sensor apparatuses, the carrier 3120 may take the form of, or be integrated with, a pad, bedsheet, blanket, duvet or comforter cover, fitted sheet, or mattress pad.

Figure 32:
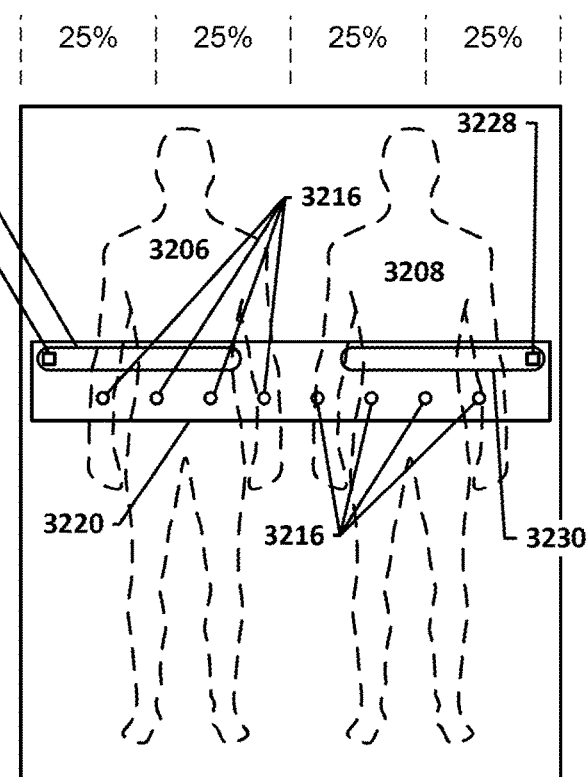
FIG. 32 depicts an implementation that is very similar to that in FIG. 31, except that the carrier includes two resonator strips that are formed from a higher-stiffness material than the carrier.

FIG. 32 depicts an implementation that is very similar to that in FIG. 31, except that the carrier 3210 includes two resonator strips 3230 that are formed from a higher-stiffness material than the carrier 3210 and to which the alarms 3228 are mounted. The resonator strips 3230 may, for example, be a flexible material such as a plastic strip, while the carrier 3210 may be a material such as a woven textile. The resonator strips 3230 may act as a resonant backboard that conducts vibrations produced by a haptic device in an alarm 3228 to a different location, e.g., to a region where a person's head is likely to be positioned, and/or to a larger area, e.g., to a 1 ft by 1 ft patch. While haptic devices such as LRAs or ERMs are quite small, they are, nonetheless, electromechanical devices and may be more noticeable to a person if positioned direction beneath that person. While positioning a haptic device directly beneath a person may make it much more likely to wake the person when the haptic device is activated as compared with positioning the haptic device in a location off to the side of the person, such positioning may be uncomfortable to the person when the haptic device is inactive and may adversely impact their sleep. The use of a resonator strip 3230 may allow the haptic device/alarm 3228 to be positioned off to the side of the person while allowing the vibrations produced by the haptic device to be conducted to locations directly beneath the person. Since the resonator strips 3230 may be relatively flat and made of a flexible material, they may be much more comfortable to lie on directly than the haptic device 3228. A further benefit of using a resonator strip 3230 is that a haptic device is typically a point-source of vibration, i.e., the vibrations are induced within a relatively small housing, and those vibrations then radiate outwards through the carrier 3220 and the mattress 3210. If the carrier 3220 and/or mattress 3210 (or, more specifically, the upper surface of the mattress 3210) are made of a low-stiffness material, e.g., a textile, then the vibrations from the haptic device may be quickly attenuated, limiting the ability of the haptic device to wake a person. However, if a resonator strip 3230 is used, then the resonator strip 3230 may attenuate the vibrations from the haptic device to a much lower extent than the carrier 3220 or mattress 3210, thereby transferring more vibrational energy to the person and increasing the likelihood that the vibrations from the haptic device will wake the person up. It is to be understood that the resonator strips 3230 may be used in any of the wake-up alarm system implementations discussed herein.

The other components in FIG. 32 that have the same last two digits as the components discussed above with respect to FIG. 31 are similar to those corresponding components in FIG. 31, and the discussion above with respect to FIG. 31 may be referred to for descriptions of such components.

Figure 33:
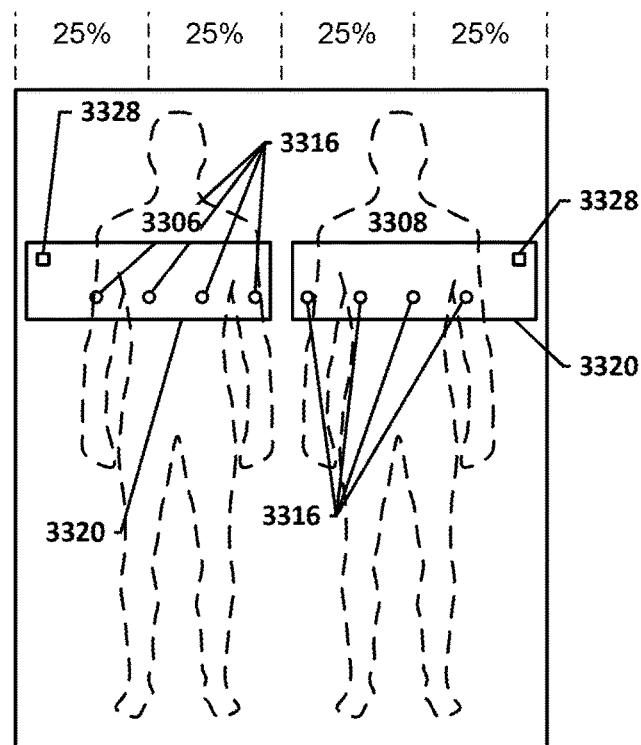
FIG. 33 depicts another wake-up alarm implementation in which each alarm is located on a separate carrier.

FIG. 33 depicts another wake-up alarm implementation in which each alarm is located on a separate carrier. For example, FIG. 33 depicts two carriers 3320, each with an alarm 3328 and a plurality of sensors 3316 (which may form part of a sleep monitoring system). The carriers 3320 may be positioned on a mattress 3310 as shown in order to provide for sleep monitoring functionality as well as individualized wake-up alarm functionality for the sleepers 3306 and 3308. In some instances, the carriers 3320 may be reversible, i.e., they may function correctly regardless of which major surface is uppermost—this allows the same carrier 3320 to be used on either side of the mattress 3310 by simply flipping the carrier 3320 upside down in order to position the alarms 3328 on opposing sides of the mattress 3310.

Figure 34:
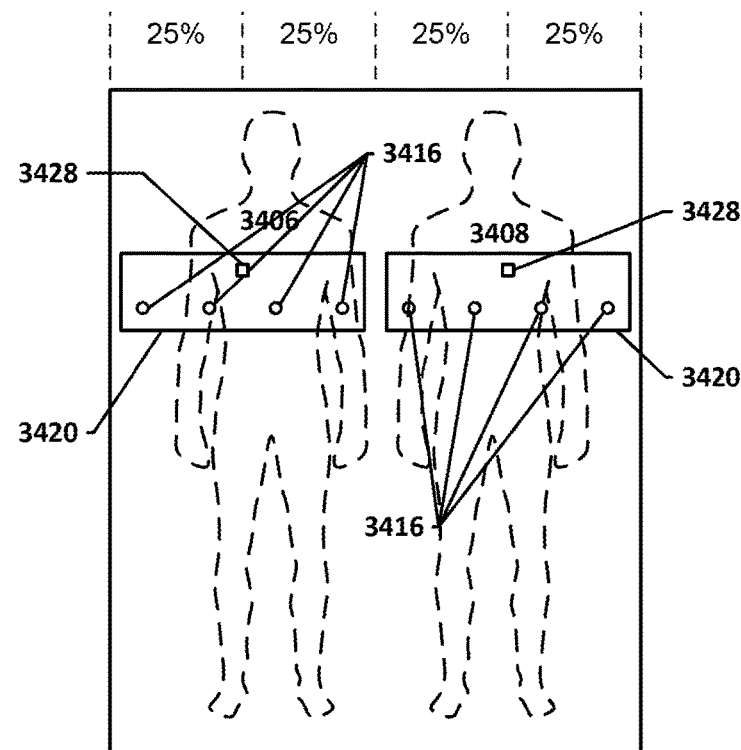
FIG. 34 depicts another wake-up alarm implementation that is similar to that depicted in FIG. 33, except that the carriers are symmetric.

FIG. 34 depicts another wake-up alarm implementation that is similar to that depicted in FIG. 33, except that the carriers 3420 (and associated sensors 3416 and alarm 3428) are symmetric, thereby allowing the same carrier 3420 to be used on either side of the mattress 3410, e.g., in locations underneath sleepers 3406 and 3408.

An advantage of the carriers shown in FIGS. 33 and 34 is that such carriers may be used for both two-person and single-person mattresses.

Generally speaking, the alarms in a wake-up alarm system designed for beds large enough for two sleepers may be spaced apart in the transverse direction of the mattress by at least 40% of the width of the mattress. In some implementations, such spacing may amount to a distance of at least 2 feet, at least 3 feet, or at least 4 feet. In such implementations, the carrier may be wider along the transverse direction of the mattress than the spacing between the alarms. In some implementations, the spacing between the alarms may be such that each alarm is positioned within a region located within the outer 25% of the width of the mattress along the transverse direction (such as in one of the outer quartiles indicated in FIGS. 31 through 35). In some such implementations, the carrier may include resonator strips that each span from a region located within an outer quartile of the mattress along the transverse direction to a similar location in the adjacent quartile.

Figure 35:
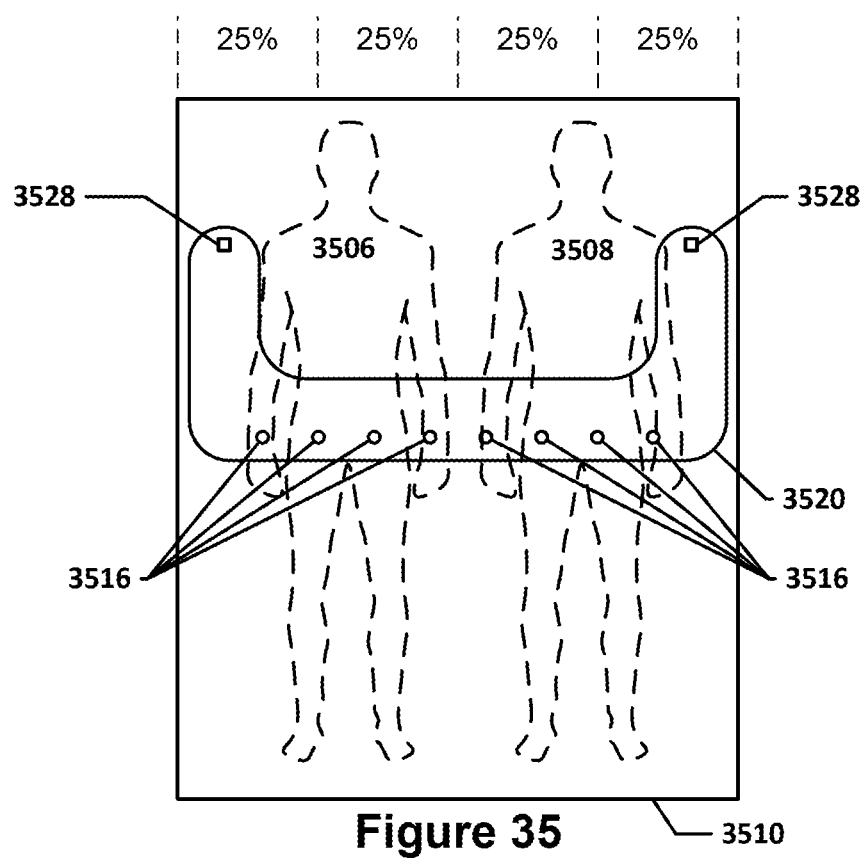
FIG. 35 depicts another wake-up alarm implementation.

FIG. 35 depicts another wake-up alarm implementation. In FIG. 35, the carrier 3520 is U-shaped, with sensors 3516 distributed across the base of the U and with the alarms 3528 located at the upper ends of the vertical arms of the U. Such a configuration allows the sensors 3516, which may be pressure sensors, to be located near the centers of mass for the sleepers 3506 and 3508 on the mattress 3510, while positioning the alarms 3528 near the heads of the sleepers 3506 and 3508, which may increase the likelihood that the alarms 3528 will be able to wake the sleepers 3506 or 3508 while allowing the sensors 3516 to obtain data that is most likely to accurately reflect the relative positioning of sleepers on the bed.

Generally speaking, the alarms used in a wake-up alarm system may be activated through providing signals to the alarms. In some implementations, the signal may simply be a power signal to the alarm (or to a device of a multi-mode alarm; multi-mode alarms are discussed in more detail in the following paragraph) and that causes the alarm to activate for as long as the power signal is provided. In other implementations, the signal may be a data signal or other signal that is interpreted by a processor or circuit associated with the alarm; the processor or circuit associated with the alarm may then activate the alarm in response to receiving such a signal. In such implementations, the alarm may continue to stay active until the processor or circuit associated with the alarm receives a subsequent signal that causes the processor or circuit to deactivate the alarm.

In some implementations, each alarm may include multiple different devices. For example, an alarm may include both a speaker and a haptic device, and, depending on the particular circumstances, one or both of these devices may be activated in order to provide an alert to a person. In some implementations where multiple different devices are included in each alarm (which may be referred to herein as "multi-mode" alarms), the particular device that is activated when it is desired to activate the alarm may be user-selectable. For example, a user may specify that they prefer audible alarms over haptic alarms, and, in such circumstances, when a multi-mode alarm for that user is to be activated, the speaker of the alarm may be caused to emit noise while the haptic device of the alarm may be left inactive. Similarly, if a user specifies that they prefer haptic alarms over audible alarms, then the wake-up alarm system may cause the haptic device to activate while keeping the speaker inactive. In some implementations, two users that are both associated with a particular wake-up alarm system with multi-mode alarms may each specify their preferences, and the wake-up alarm system may be configured to override the preferences for one of those users if an alarm is to be activated to wake that user while the other user is present in the bed. For example, if a first user prefers audible alarms and a second user prefers haptic alarms, the wake-up alarm system may be configured to activate a multi-mode alarm for the first user by activating a speaker component of that alarm if, for example, it is determined that the second user is not in the bed (such as may be determined, for example, through the use of a sleeper identification system). However, if the wake-up alarm system determines that the second user is present in the bed when it is time to activate the alarm for the first user, then the wake-up alarm system may cause a haptic device in the alarm to activate instead of the speaker so as to avoid making noise that might be irritating to the second user. In some such implementations, the wake-up alarm system may be configured to, if it overrides a user's preferred alarm setting due to the presence of another user in the bed, switch the alarm output back to the user's preferred alarm setting after some time interval if the user does not wake up. For example, if the wake-up alarm system activates a haptic device for an audible-alarm-preferring first user due to the presence of a haptic-alarm-preferring second user and the first user, based on analysis provided by a sleeper presence monitoring system (SPMS) (for example, if the sleeper presence monitoring system indicates that the first user is still present in the bed) or a sleep monitoring system (for example, if the sleep monitoring system indicates that the first user is still in an "asleep" state), does not appear to be waking up after the alarm is activated for a certain period of time, e.g., 30 seconds or a minute, then the wake-up alarm system may cause the alarm to switch to the first user's preferred output mode, e.g., to audible output, in order to cause the first user to wake up. Thus, in such implementations, the wake-up alarm system may be able to wake one user up in a manner that is least likely to wake the other user up if both are present in the bed together when only of the users is to be woken.

Alarm Functionality

Figure 36:
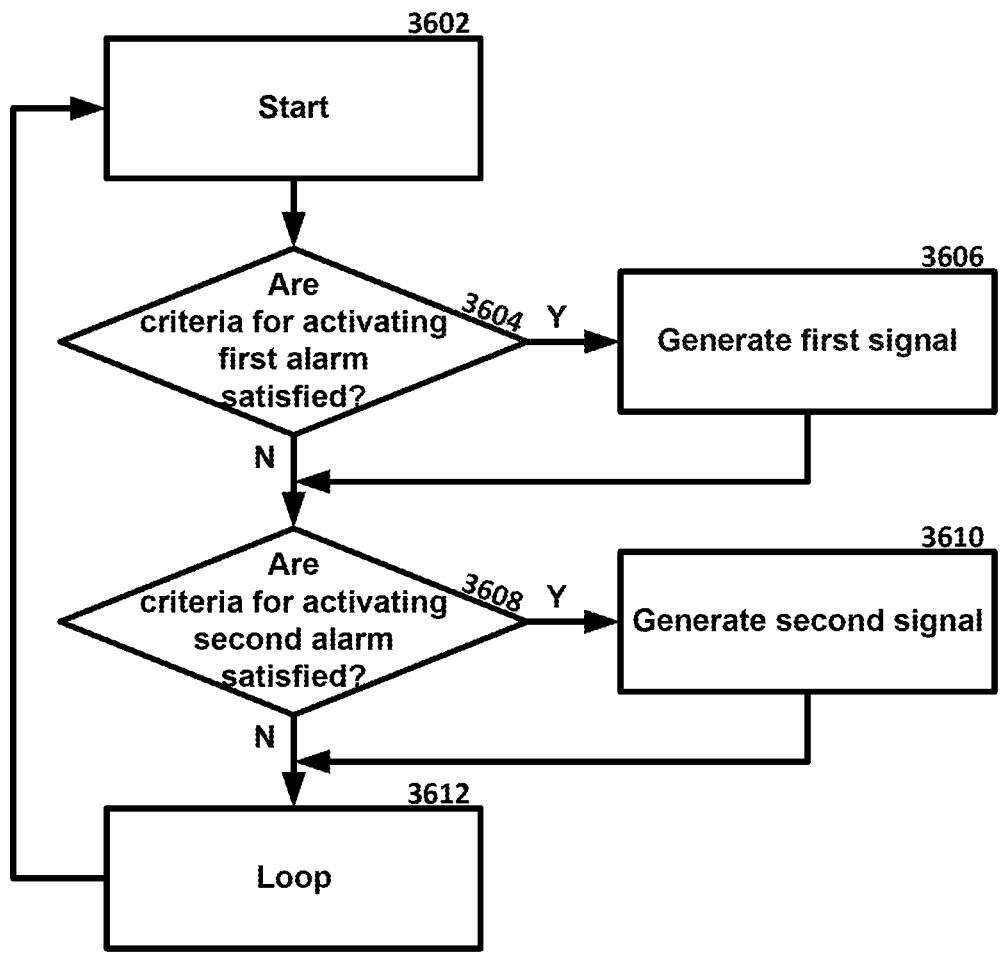
FIG. 36 is a flow diagram of a high-level process for how a wake-up alarm system may operate.

Generally speaking, the wake-up alarm system may provide for wake-up alarms that are tailored, in some manner, to the behavior of a user or to the user's identity. FIG. 36 is a flow diagram of a high-level process for how a wake-up alarm system may operate. In FIG. 36, the process may begin in block 3602. In block 3604, a determination may be made as to whether certain criteria associated with a first alarm are met. If so, then a first signal may be generated in block 3606 before proceeding to block 3608. If not, then the process may proceed to block 3608 directly. In block 3608, another determination may be made as to whether certain criteria associated with a second alarm are met. If so, then a second signal may be generated in block 3610 before proceeding to block 3612. If not, then the process may proceed to block 3612 directly. The first and second signals may, respectively, cause a first alarm or a second alarm to activate. After reaching block 3612, the process may then return to block 3602 for another cycle of monitoring alarm conditions. It is to be understood that while the processor shown indicates that the determining whether the criteria are met for each alarm occurs serially, various implementations may perform such checks in parallel or independently of one another. This applies as well to other implementations discussed later in which two alarms are managed. It is also to be understood that the techniques and systems discussed herein in the context of a two-user system, e.g., a wake-up alarm system with two alarms, may also be implemented as single-user systems by omitting the components and functionality associated with the second person.

The criteria that are used to trigger each alarm will generally include determining whether a wake time associated with that alarm has been met, and may potentially include further criteria, such as whether a person is located on the bed or mattress in a location associated with that alarm when the wake time is reached, what the sleep state is of a person located on the bed or mattress in a location associated with that alarm when the wake time is reached, and so forth. Several of these more detailed techniques for triggering alarms in wake-up alarm systems are discussed below in more detail. The alarms may also be triggered in response to certain conditions that do not involve meeting a wake-up time, as is discussed with respect to some implementations later in this disclosure.

In some implementations, for example, a wake-up alarm system may be configured to store wake times associated with alarms positioned on opposing sides of a mattress via a carrier. Each wake time, for example, may be set according to the desired wake time of an individual that normally sleeps on that side of the bed. The wake-up alarm system may then activate each alarm when its respective wake time occurs if an associated sleeper presence monitoring system indicates that there is a person on the side of the mattress associated with that alarm.

Figure 37:
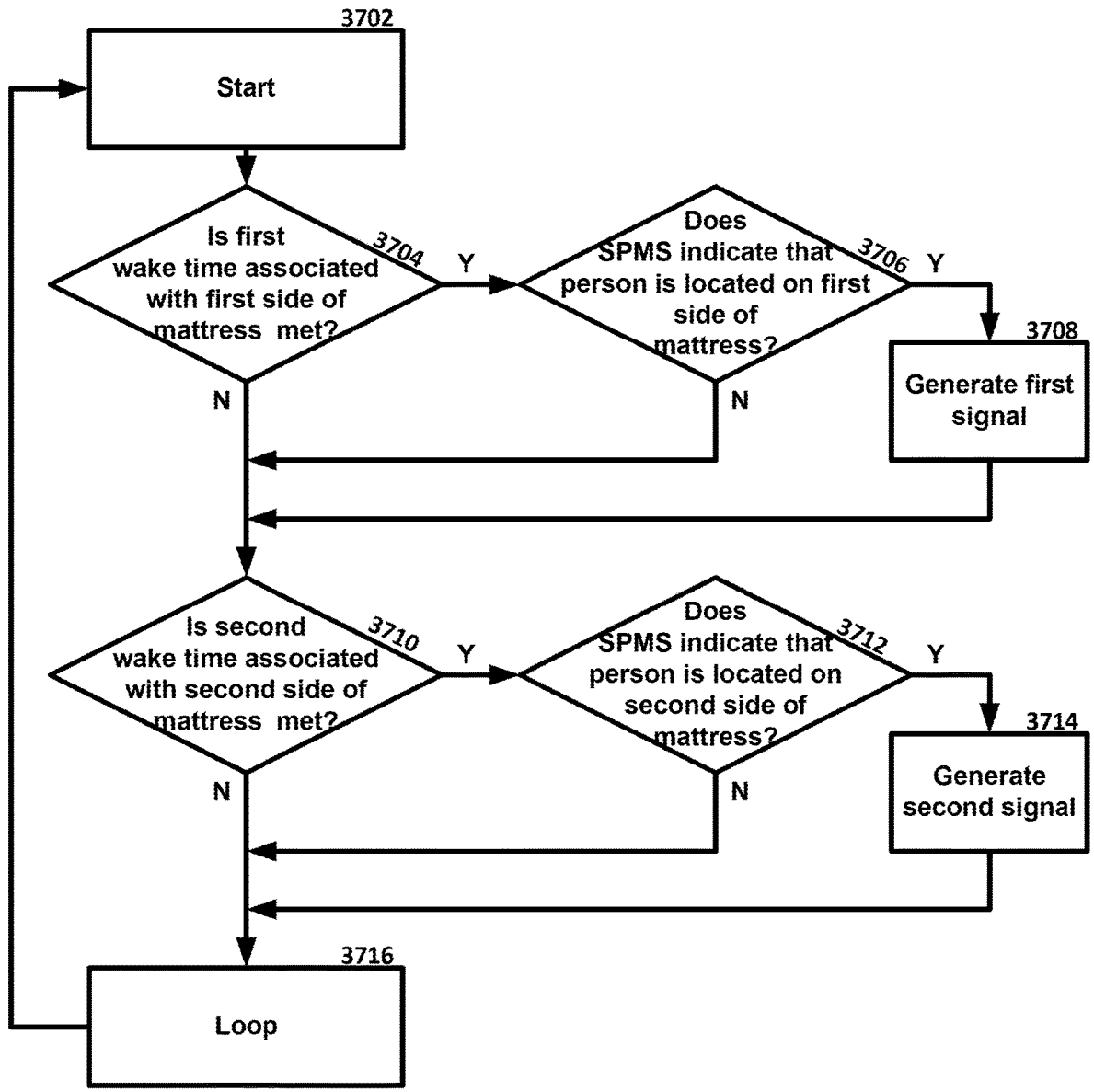
FIG. 37 depicts a high-level flow diagram for a technique for activating an alarm responsive to reaching a specified wake time while a person is on a mattress in a location associated with the alarm.

FIG. 37 depicts a high-level flow diagram for a technique for activating an alarm responsive to reaching a specified wake time while a person is on a mattress in a location associated with the alarm. The technique may begin in block 3702 and may proceed to block 3704, in which a determination may be made as to whether a first wake time associated with a first alarm location on the first side of a mattress is met. If the first wake time has been met in block 3702, then the technique may proceed to block 3706, in which a further determination may be made, based on data from a sleeper presence monitoring system (SPMS, as discussed later herein), as to whether there is actually a person present on the first side of the mattress. For example, the sleeper presence monitoring system may analyze sensor data from pressure sensors located on a carrier on top of the mattress, and may determine from such pressure sensors that an object that produces a pressure distribution similar to that produced by a person is present on the first side of the mattress, and may thus indicate that a person is present on the first side of the mattress. If it is determined in block 3706 that a person is present on the first side of the mattress, the technique may proceed to block 3708, in which a first signal may be generated so as to cause the first alarm associated with the first side of the mattress to activate. If it is determined in block 3704 that the first wake time has not been met or in block 3706 that there is no person located on the first side of the mattress, then the technique may proceed to block 3710.

In block 3710, a determination may be made as to whether a second wake time associated with a second alarm location on the second side of the mattress is met. If the second wake time has been met in block 3710, then the technique may proceed to block 3712, in which a further determination may be made, based on data from the sleeper presence monitoring system, as to whether there is actually a person present on the second side of the mattress. If it is determined in block 3712 that the person is present on the second side of the mattress, the technique may proceed to block 3708, in which a second signal may be generated so as to cause the second alarm associated with the second side of the mattress to activate. If it is determined in block 3710 that the second wake time has not been met or in block 3712 that there is no person located on the second side of the mattress, then the technique may proceed to block 3716, after which it may return to block 3702.

Such a technique may be used in implementations having a sleeper identification system, as well as in implementations that have a more limited feature set, such as systems that do not have a sleeper identification system but nonetheless have a sleeper presence monitoring system. In systems with a sleeper identification system, the sleeper identification system may act as the sleeper presence monitoring system.

Figure 38A:
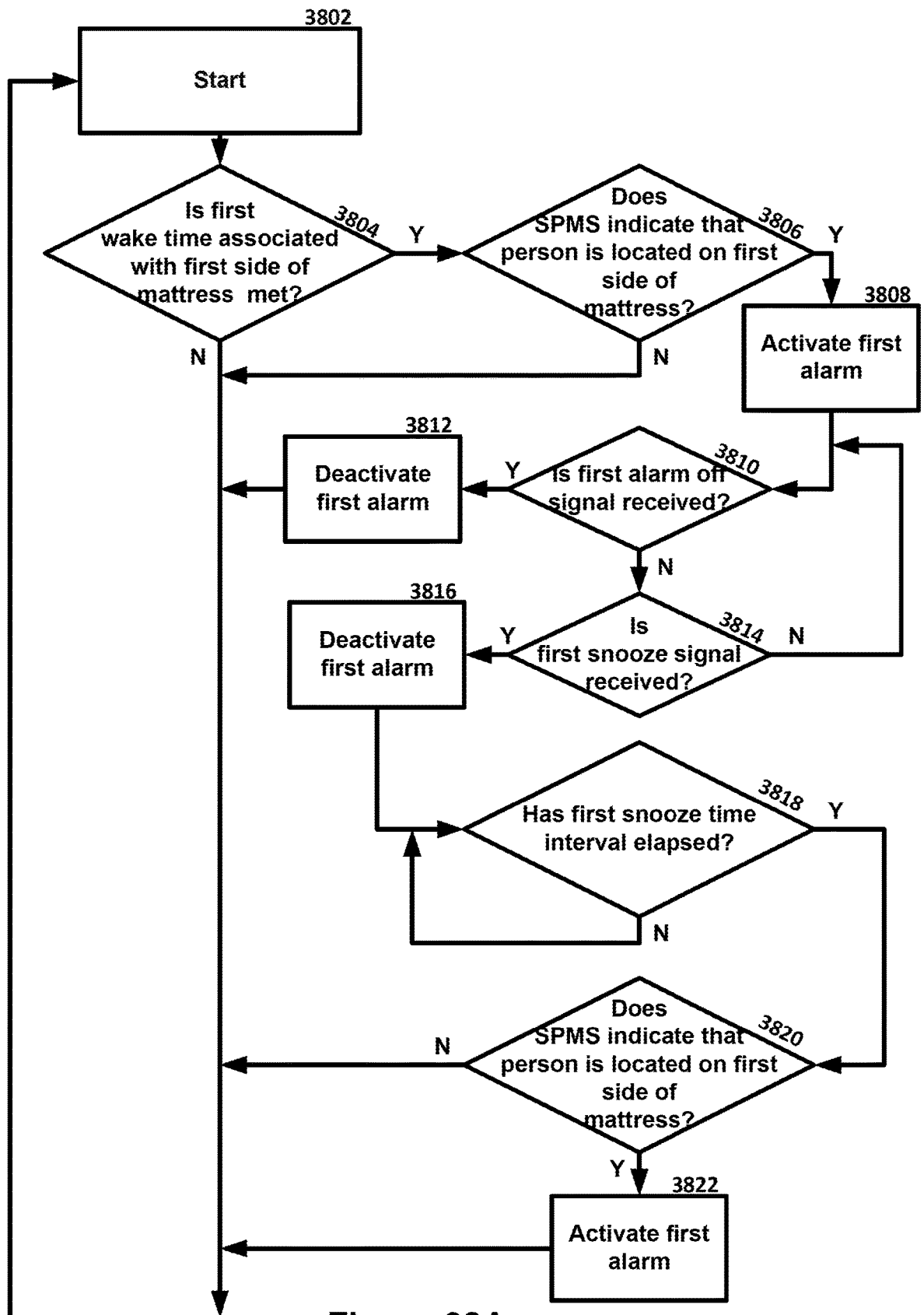
FIGS. 38A and 38B depict a flow diagram for a more involved technique that may be used with a wake-up alarm system.
Figure 38B:
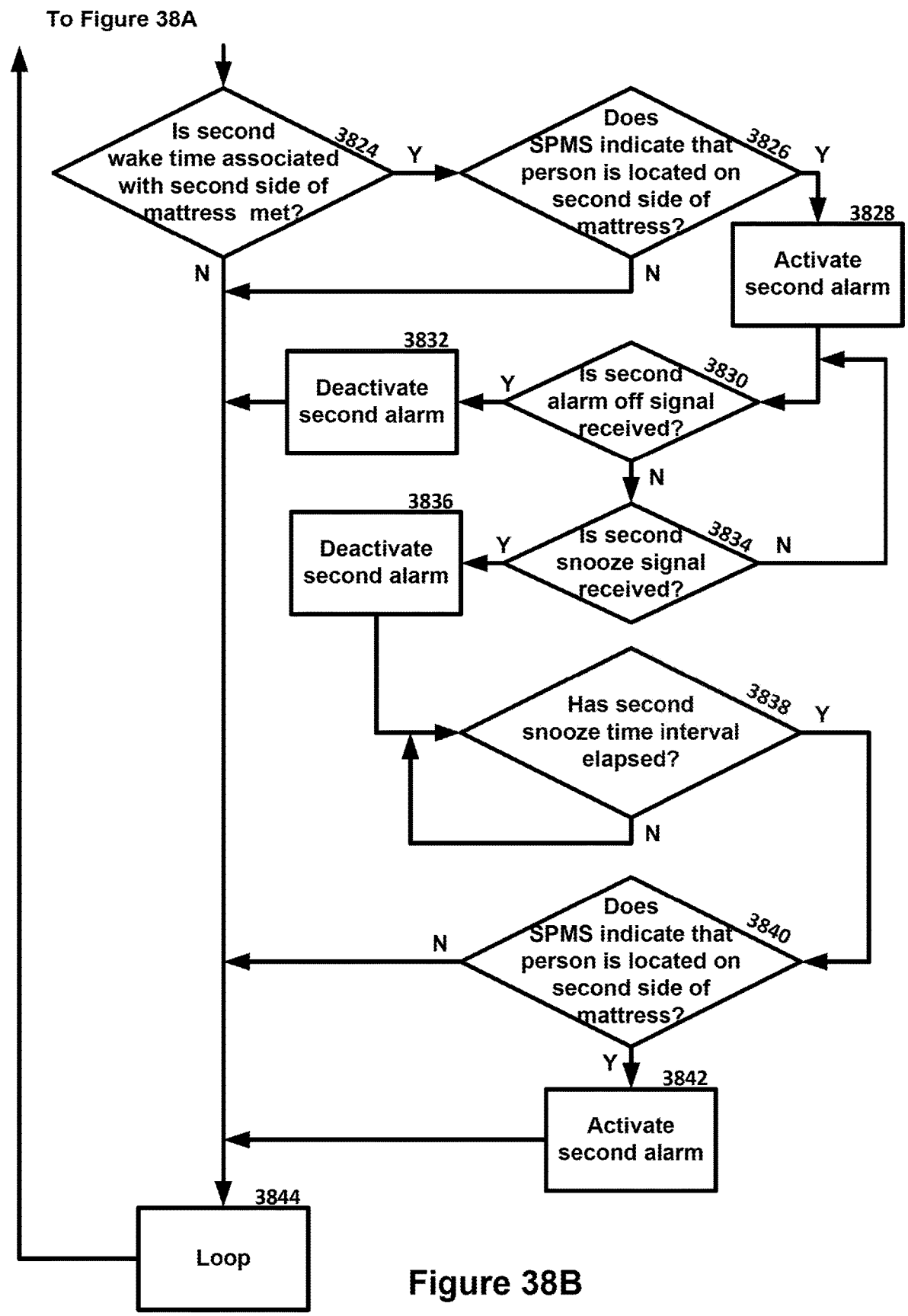

FIGS. 38A and 38B depict a flow diagram for a more involved technique that may be used with a wake-up alarm system. The technique may begin in block 3802, and may then proceed to block 3804, in which a determination may be made as to whether a first wake time associated with a first alarm on a first side of a mattress has been met. If the first wake time has been met, then the technique may proceed to block 3806, where a further determination may be made whether data from a sleeper presence monitoring system indicates that a person is located on the first side of the mattress. If it is determined in block 3806 that a person is located on the first side of the mattress, then the technique may proceed to block 3808, in which a first signal may be generated in order to cause the alarm associated with the first side of the mattress to activate. From block 3808, the technique may proceed to block 3810, in which a determination may be made as to whether or not a first alarm off signal has been received by the wake-up alarm system. Such a first alarm off signal may be provided, for example, by way of an input button, control, or other input device that is integrated into the wake-up alarm system, or may be provided through input via a smartphone, tablet, or other device that is communicatively connected with the wake-up alarm system. If the first alarm off signal has been received, then the technique may proceed to block 3812, in which the first alarm may be deactivated, and then to block 3824, which is discussed in more detail later.

If it is determined in block 3810 that the first alarm off signal has not been received, then the technique may proceed to block 3814, in which a determination may be made as to whether a first snooze signal has been received by the wake-up alarm system. The first snooze signal may, for example, be obtained from an input similar to those discussed above with respect to the first alarm off signal. The first alarm off signal and/or the first snooze signal may also or alternatively be provided by interactions with sensors that may be part of the sleeper presence monitoring system. For example, the wake-up alarm system may be configured to identify sensor inputs that are indicative of certain actions, e.g., accelerations that are indicative of the user slapping the mattress twice, or some other distinctive input, which may be interpreted as either the first alarm off signal or the first snooze signal.

If it is determined in block 3814 that the first snooze signal has not been received, the technique may return to block 3810. However, if it is determined in block 3814 that the first snooze signal has been received, the technique may proceed to block 3816, in which the first alarm may be deactivated, and then to block 3818, in which a determination may be made as to whether a first snooze time interval has elapsed from the receipt of the first snooze signal (or from when the first alarm has been deactivated). If it is determined in block 3818 that the first snooze time interval has not yet elapsed, then the technique may return to block 3818. If it is determined in block 3818, however, that the first snooze time interval has elapsed, then the technique may proceed to block 3820, in which a determination may be made as to whether the sleeper presence monitoring system indicates that a person is located on the first side of the mattress.

It is to be understood that for the techniques discussed herein where there is a determination as to whether a person is present on a particular side of a mattress in association with an alarm-related activity, e.g., when a wake time is met or when an alarm is to be activated, the determination as to whether a person is present on that side of the mattress may be made at the same time as the associated alarm-related activity, or may be made within a time interval that is close in time to the associated alarm-related activity (for example, during a time window several seconds in advance of the associated alarm-related activity, or during a time window that includes the associated alarm-related activity). This is applicable to all of the techniques discussed herein.

If it is determined in block 3820 that the sleeper presence monitoring system indicates that a person is not present on the first side of the mattress, then the technique may proceed to block 3824 without triggering the first alarm. However, if it is determined in block 3820 that the sleeper presence monitoring system indicates that a person is present on the first side of the mattress, then the technique may proceed to block 3822, in which the first alarm may be reactivated. From block 3822, the technique may then proceed to block 3824 (although there may be intermediate steps in which the first alarm may be deactivated in response to further user input or after a certain time interval has elapsed) or, alternatively, the technique may return to block 3810, in which case there may be further snooze periods.

In block 3824, a determination may be made as to whether a second wake time associated with a second alarm on a second side of a mattress has been met. If the second wake time has been met, then the technique may proceed to block 3826, where a further determination may be made whether data from a sleeper presence monitoring system indicates that a person is located on the second side of the mattress. If it is determined in block 3826 that a person is located on the second side of the mattress, then the technique may proceed to block 3828, in which a second signal may be generated in order to cause the alarm associated with the second side of the mattress to activate. From block 3828, the technique may proceed to block 3830, in which a determination may be made as to whether or not a second alarm off signal has been received by the wake-up alarm system. Such a second alarm off signal may be provided, for example, by way of an input button, control, or other input device that is integrated into the wake-up alarm system, or may be provided through input via a smartphone, tablet, or other device that is communicatively connected with the wake-up alarm system. If the second alarm off signal has been received, then the technique may proceed to block 3832, in which the second alarm may be deactivated, and then to block 3844, which is discussed in more detail later.

If it is determined in block 3830 that the second alarm off signal has not been received, then the technique may proceed to block 3834, in which a determination may be made as to whether a second snooze signal has been received by the wake-up alarm system. The second snooze signal may, for example, be obtained from an input similar to those discussed above with respect to the second alarm off signal or the first alarm off signal or the first snooze signal.

If it is determined in block 3834 that the second snooze signal has not been received, the technique may return to block 3830. However, if it is determined in block 3834 that the second snooze signal has been received, the technique may proceed to block 3836, in which the second alarm may be deactivated, and then to block 3838, in which a determination may be made as to whether a second snooze time interval has elapsed from the receipt of the second snooze signal (or from when the second alarm has been deactivated). If it is determined in block 3838 that the second snooze time interval has not yet elapsed, then the technique may return to block 3838. If it is determined in block 3838, however, that the second snooze time interval has elapsed, then the technique may proceed to block 3840, in which a determination may be made as to whether the sleeper presence monitoring system indicates that a person is located on the second side of the mattress.

If it is determined in block 3840 that the sleeper presence monitoring system indicates that a person is not present on the second side of the mattress, then the technique may proceed to block 3844 without triggering the second alarm. However, if it is determined in block 3840 that the sleeper presence monitoring system indicates that a person is present on the second side of the mattress, then the technique may proceed to block 3842, in which the second alarm may be reactivated. From block 3842, the technique may then proceed to block 3844 (although there may be intermediate steps in which the second alarm may be deactivated in response to further user input or after a certain time interval has elapsed) or, alternatively, the technique may return to block 3830, in which case there may be further snooze periods.

When the technique reaches block 3844, then it may return to block 3802 for further monitoring.

While the techniques discussed above are described with respect to a sleeper presence monitoring system implementation, these same techniques may be used with sleeper identification systems.

It is also to be understood that while the techniques discussed herein involving scenarios with multiple sleepers are depicted with operations shown in a serial manner, e.g., first actions taken with respect to a first sleeper are performed, and then actions with respect to a second sleeper, in actual practice, the actions taken with respect to each sleeper may be executed in parallel. Thus, for example, wake-up alarm times for two sleepers may be tracked concurrently, and alarms for each sleeper may be activated independently and deactivated independently. By way of further example, blocks 3804-3822 may be executed in parallel with blocks 3824-3842 so that, for example, the activation of the second alarm after the first alarm is not contingent on the first alarm's snooze time interval elapsing if the first alarm is in a snooze state. This applies to other implementations discussed herein that are similarly depicted.

Figure 39:
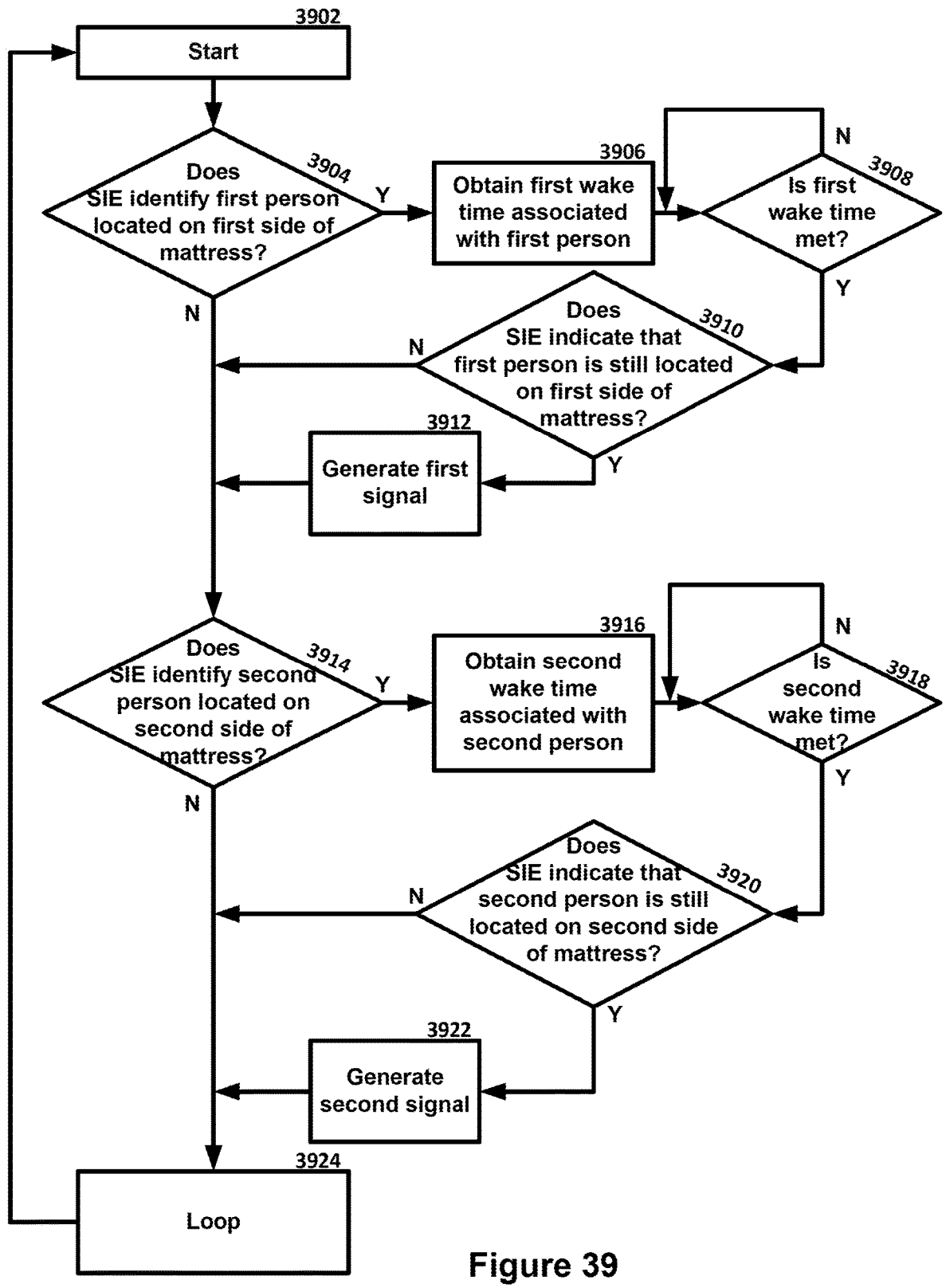
FIG. 39 depicts a flow diagram for a technique uses a sleeper identification system in order to select between different wake times.

FIG. 39 depicts a flow diagram for a technique uses a sleeper identification system in order to select between different wake times. In FIG. 39, the technique may begin in block 3902 and then proceed to block 3904, in which a determination may be made as to whether a sleeper identification engine or system has identified a first person on a first side of a mattress. If it is determined in block 3904 that the first person is on the first side of the mattress, then the technique may proceed to block 3906, in which a first wake time associated with the first person may be retrieved by the wake-up alarm system, e.g, by querying a database or data store that contains a stored first wake time that is associated with the first person. It is to be understood that if another person, e.g., a second person, is identified as being located on the first side of the mattress by the sleeper identification system, then a different stored wake time associated with that other person may be retrieved instead and used in place of the first wake time.

Once the first wake time (or other wake time associated with whatever person is identified as being on the first side of the mattress) is obtained, the technique may proceed to block 3908, in which a determination may be made as to whether the first wake time has been met. If not, then the technique may return to block 3908. If so, then the technique may proceed to block 3910, in which a determination may be made as to whether the sleeper identification system indicates that the first person is still located on the first side of the mattress. In some implementations, such a determination may simply be whether a person (without checking to see if that person is the first person) is located on the first side of the mattress. If it is determined in block 3910 that the first person (or a person) is still located on the first side of the mattress, then the technique may proceed to block 3912, in which a first signal to activate the first alarm may be generated before the technique proceeds to block 3914 (there may be other steps as well, such as steps for turning off the first alarm or snoozing the first alarm, such as are described with respect to the implementation of FIGS. 38A and 38B).

In block 3914, a determination may be made as to whether a sleeper identification engine or system has identified a second person on a second side of the mattress. If it is determined in block 3914 that the second person is on the second side of the mattress, then the technique may proceed to block 3916, in which a second wake time associated with the second person may be retrieved by the wake-up alarm system, e.g, by querying the database or data store that contains a stored second wake time that is associated with the second person. It is to be understood that if another person, e.g., the first person, is identified as being located on the second side of the mattress by the sleeper identification system, then a different stored wake time associated with that other person may be retrieved instead and used in place of the second wake time.

Once the second wake time (or other wake time associated with whatever person is identified as being on the second side of the mattress) is obtained, the technique may proceed to block 3918, in which a determination may be made as to whether the second wake time has been met. If not, then the technique may return to block 3918. If so, then the technique may proceed to block 3920, in which a determination may be made as to whether the sleeper identification system indicates that the second person is still located on the first side of the mattress. In some implementations, such a determination may simply be whether a person (without checking to see if that person is the second person) is located on the second side of the mattress. If it is determined in block 3920 that the first person (or a person) is still located on the second side of the mattress, then the technique may proceed to block 3922, in which a second signal to activate the second alarm may be generated before the technique proceeds to block 3924 (there may be other steps as well, such as steps for turning off the second alarm or snoozing the second alarm, such as are described with respect to the implementation of FIGS. 38A and 38B).

Thus, the wake time for a particular alarm may be selected from a database based on the identify of whatever person is sleeping on the side of the bed associated with that alarm.

Wake-up alarm systems may also include additional functionality besides providing wake-up alarms for people. Such systems may also, in some implementations, include the ability to utilize the alarms for other purposes, such as to help prevent pets from sleeping on a user's bed.

Figure 40:
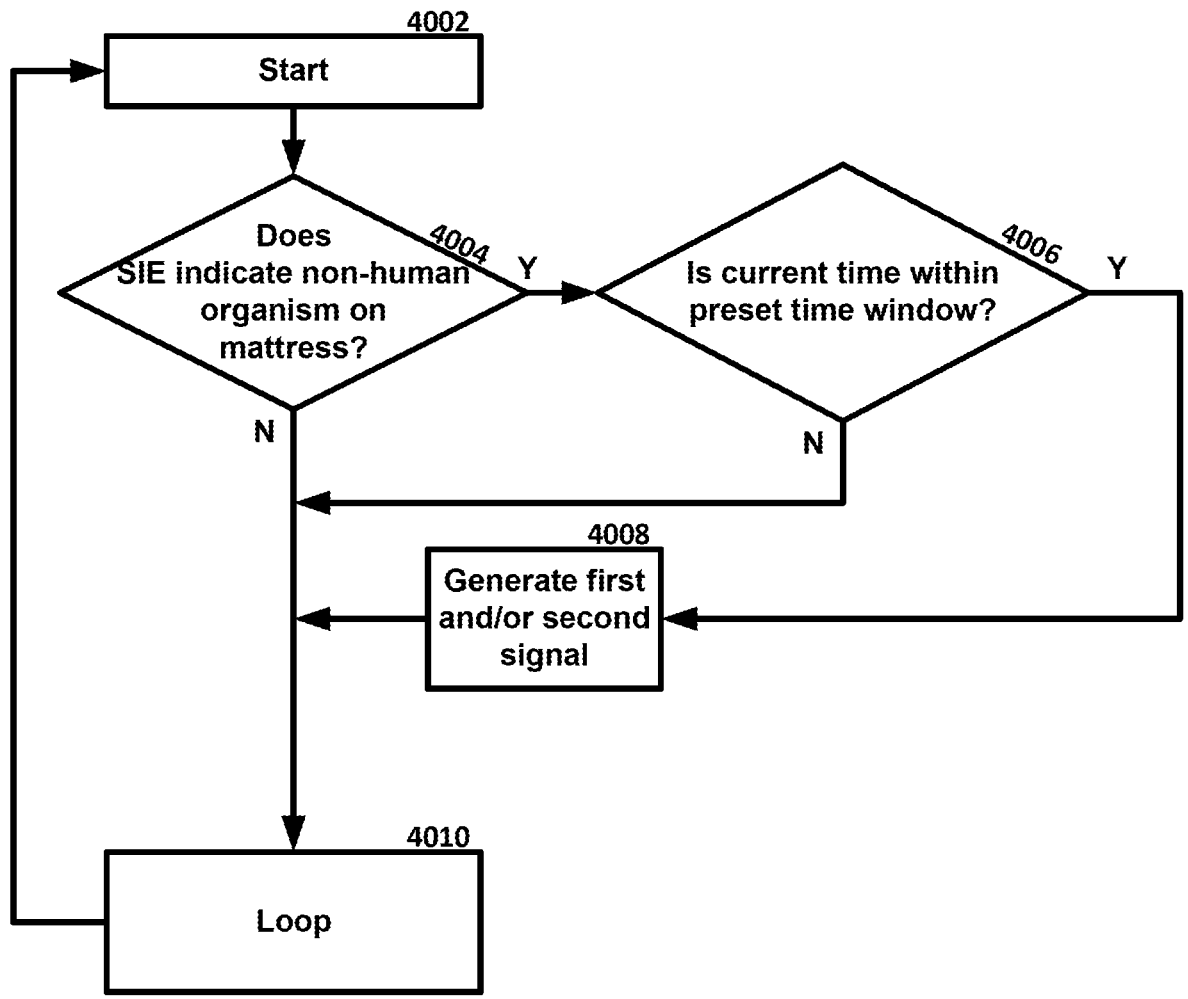
FIG. 40 depicts a high-level flow diagram for a technique that may be used with a wake-up alarm system to prevent pets from sleeping on a bed.

FIG. 40 depicts a high-level flow diagram for a technique that may be used with a wake-up alarm system to prevent pets from sleeping on a bed. In FIG. 40, the technique may begin in block 4002 before proceeding to block 4004, in which a determination may be made as to whether a sleeper identification system indicates that a non-human organism is present on the mattress. For example, the sleeper identification system may register that pressure sensors that are mounted on the carrier are producing sensor output that indicates movement patterns consistent with a living organism being on the mattress, but with pressures that are lower than those typically produced by a human (due to the fact that most pets are considerably lighter than adult humans). If it is determined in block 4004 that no non-human organism is on the mattress, then the technique may proceed to block 4010. However, if is determined in block 4004 that a non-human organism, e.g., a pet, such as a dog or cat, is located on the mattress, then the technique may proceed to block 4006, in which a determination may be made as to whether the current time is within a specified time window. If it is determined in block 4006 that the current time is not within the specified time window, then the technique may proceed to block 4010. However, if it is determined in block 4006 that the current time is within the specified time window, the technique may proceed to block 4008, in which a first and/or second signal may be generated in order to activate one or more of the alarms used in the wake-up alarm system, after which the technique may proceed to block 4010 before returning to block 4002. It is to be understood that the alarm(s), in such an implementation, may be deactivated after being activated in block 4008 after a specified period of time, or, alternatively, after the sleeper identification system indicates that the non-human organism has vacated the mattress. Block 4006 may be used to allow pets to be on the mattress only during certain time intervals and is thus optional if such scheduling functionality is not desired.

Figure 41:
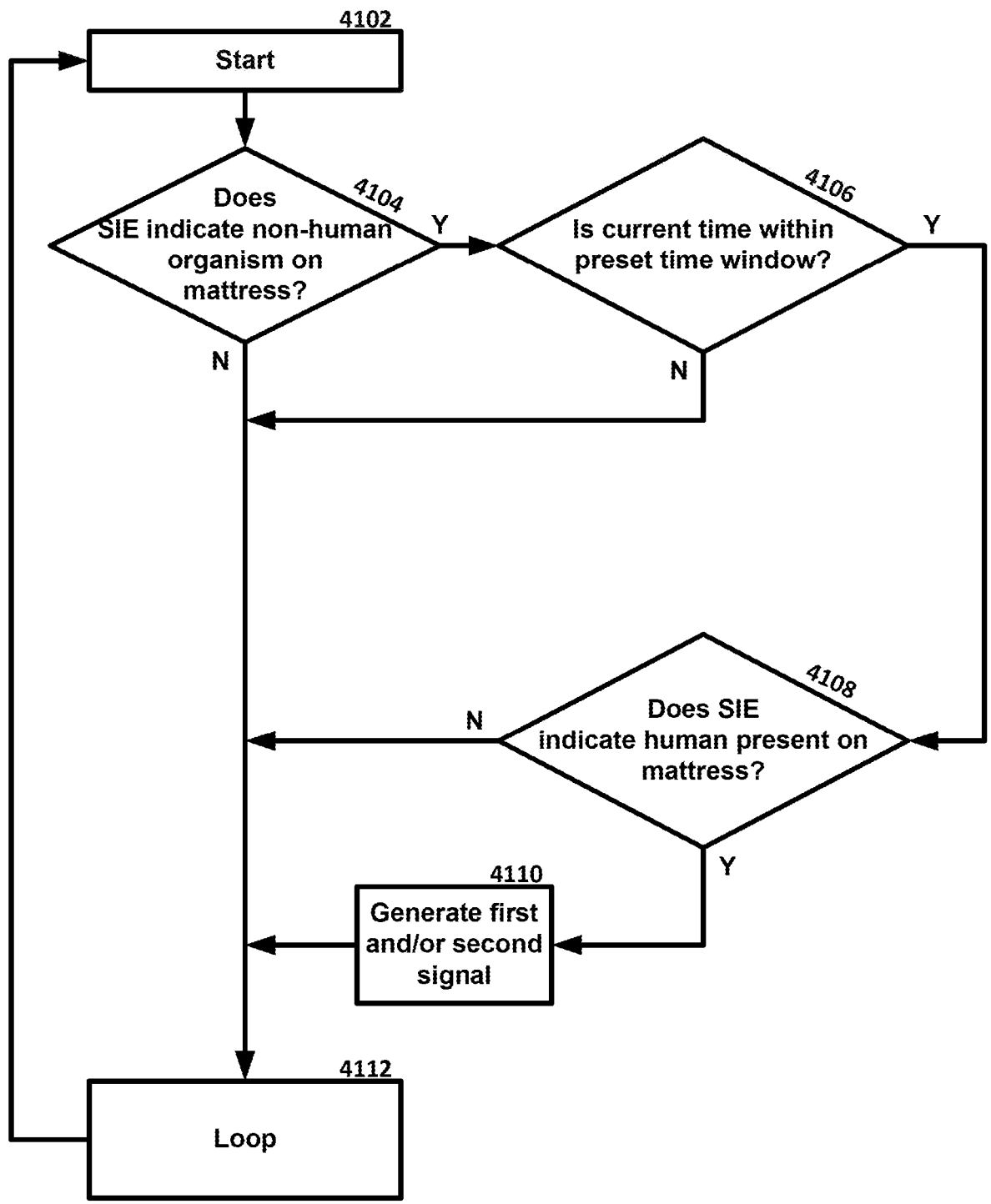
FIG. 41 depicts a high-level flow diagram for another technique that may be used with a wake-up alarm system to prevent pets from sleeping on a bed.

FIG. 41 depicts a high-level flow diagram for another technique that may be used with a wake-up alarm system to prevent pets from sleeping on a bed. In FIG. 41, the technique may begin in block 4102 before proceeding to block 4104, in which a determination may be made as to whether a sleeper identification system indicates that a non-human organism is present on the mattress, such as is discussed with respect to FIG. 40. If it is determined in block 4104 that no non-human organism is on the mattress, then the technique may proceed to block 4112. However, if is determined in block 4104 that a non-human organism, e.g., a pet, such as a dog or cat, is located on the mattress, then the technique may proceed to block 4106, in which a determination may be made as to whether the current time is within a specified time window. If it is determined in block 4106 that the current time is not within the specified time window, then the technique may proceed to block 4112. However, if it is determined in block 4106 that the current time is within the specified time window, the technique may proceed to block 4108, in which a further determination may be made as to whether the sleeper identification system also indicates that a person is located on the mattress. If it is determined in block 4108 that a person is also on the mattress, then the technique may proceed to block 4112 without activating the alarm(s) in order to avoid waking the person. If it is determined in block 4108 that a person is on the mattress, then the technique may proceed to block 4110, in which a first and/or second signal may be generated in order to activate one or more of the alarms used in the wake-up alarm system, after which the technique may proceed to block 4112 before returning to block 4102. It is to be understood that the alarm(s), in such an implementation, may be deactivated after being activated in block 4110 after a specified period of time, or, alternatively, after the sleeper identification system indicates that the non-human organism has vacated the mattress. Block 4106 may be used to allow pets to be on the mattress only during certain time intervals and is thus optional if such scheduling functionality is not desired, similar to block 4006 in FIG. 40.

Figure 42:
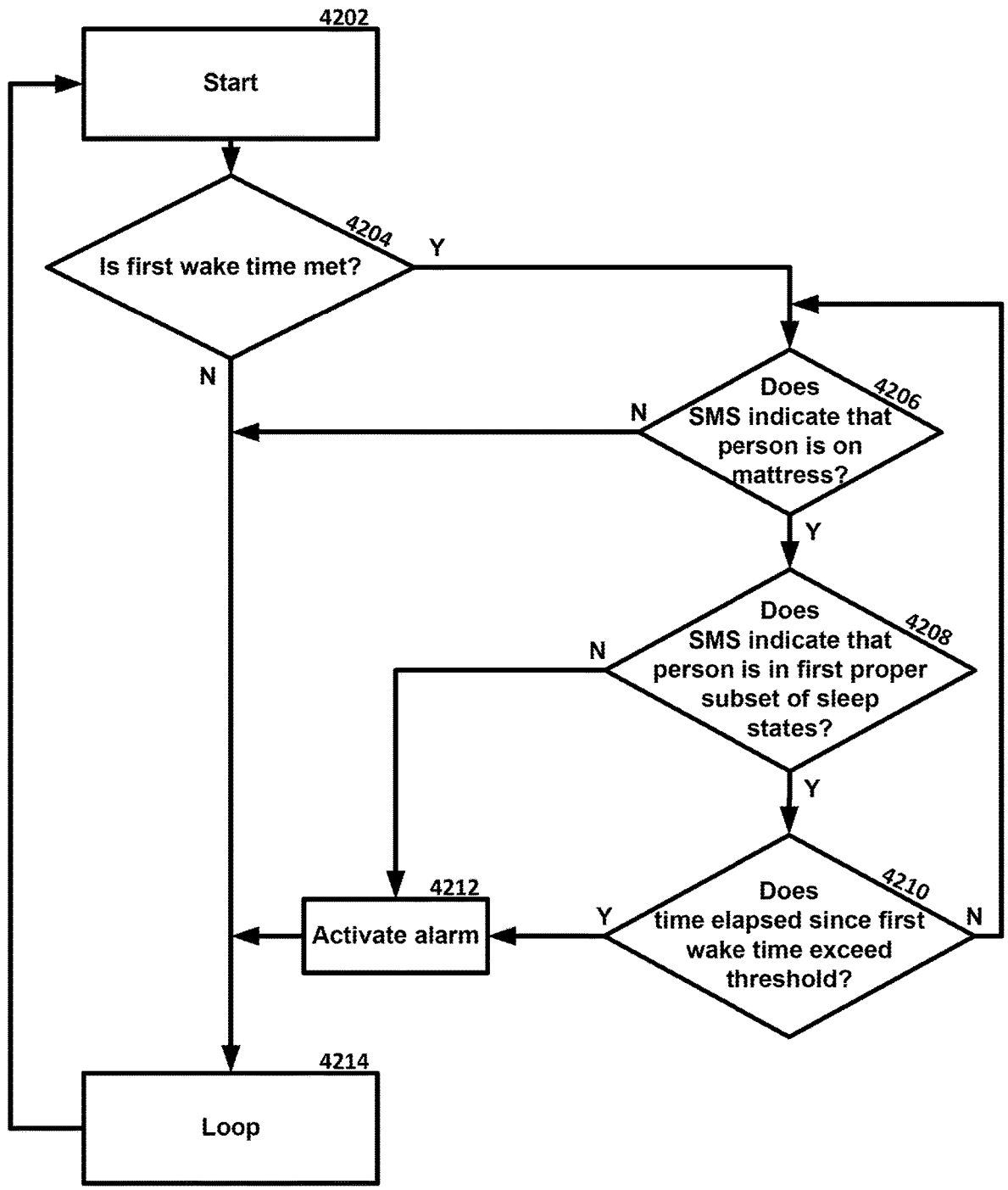
FIG. 42 depicts a high-level flow diagram of a technique that may be used with a wake-up alarm system and a sleep monitoring system to provide enhanced alarm functionality.

A wake-up alarm system may also leverage functionality that is provided by a sleep monitoring system to provide additional features. FIG. 42 depicts a high-level flow diagram of a technique that may be used with a wake-up alarm system and a sleep monitoring system to provide enhanced alarm functionality.

FIG. 42 depicts a technique that may begin in block 4202 and then proceed to block 4204, in which a determination may be made as to whether a first wake time has been met. If the implementation in question includes a sleeper identification system, then such a wake time may, for example, be a user-specific wake time that is selected based on the a sleeper's identity, as discussed earlier with respect to FIG. 39. If it is determined in block 4204 that the wake time is not met, then the technique may proceed to block 4214. If it is determined in block 4204, however, that the wake time is met, then the technique may proceed to block 4206, in which a further determination may be made as to whether a person is present on the mattress, e.g., by referencing output from a sleeper presence monitoring system. If it is determined in block 4206 that a person is not present on the mattress, then the technique may proceed to block 4214. If it is determined in block 4206 that a person is present on the mattress, then the technique may proceed to block 4208, in which a determination may be made as to whether a sleep monitoring system indicates that the person is in one of the sleep states in a proper subset of possible sleep states that are determinable by the sleep monitoring system. If it is determined in block 4208 that the person is not in the proper subset of sleep states (or is in a different proper subset of sleep states), then the technique may proceed to block 4212, where an alarm of the wake-up alarm system, such as an alarm that is located on the same side of the bed as the person, may be activated to cause the person to wake up. However, if it is determined in block 4208 that the person is in the proper subset of sleep states, then the technique may proceed to block 4210, which may delay the activation of the alarm.

For example, the sleep monitoring system may monitor a person's sleep and, based on various sensor data, determine that the person is in light, deep, or REM sleep, or is in an awake state (all of which may be considered "sleep states"—even the "awake" state). It may be undesirable to wake a person when they are in one of a proper subset of those sleep states, such as a deep or REM sleep state—in such a case, the proper subset of sleep states that causes the alarm to be activated may include, for example, only the light sleep state (to avoid waking the person during the other proper subset of REM or deep sleep states, and to avoid having the alarm go off when the person is in another proper subset of sleep states including only the awake sleep state—there would be little point to triggering the alarm if the person is already awake). However, it may nonetheless be desirable to avoid allowing the person to oversleep beyond a certain amount. Thus, in block 4210, a further determination may be made as to whether the time elapsed since the wake time was met has exceeded a specified threshold, e.g., 15 minutes or 30 minutes. If it is determined in block 4210 that the threshold has been exceeded, then the technique may proceed to block 4212, in which the alarm associated with the side of the mattress that the person is on may be activated, and then to block 4214 before returning to block 4202. If it is determined in block 4210 that the threshold has not been exceeded, then the technique may return to block 4206. Thus, the system may refrain from waking someone who is in a particular sleep state until the person is either in a sleep state that is deemed an acceptable sleep state from which to wake someone, e.g., light sleep, or the amount of time that has passed since the person was supposed to be awoken reaches a certain threshold amount.

In some implementations, the sleep state of a person may be used to adjust how the alarm of a wake-up alarm system is activated.

For example, in some implementations, the intensity of an alarm may be adjusted based on the sleep state that the person to be woken by the alarm is in at the time the alarm is to be activated.

Figure 43:
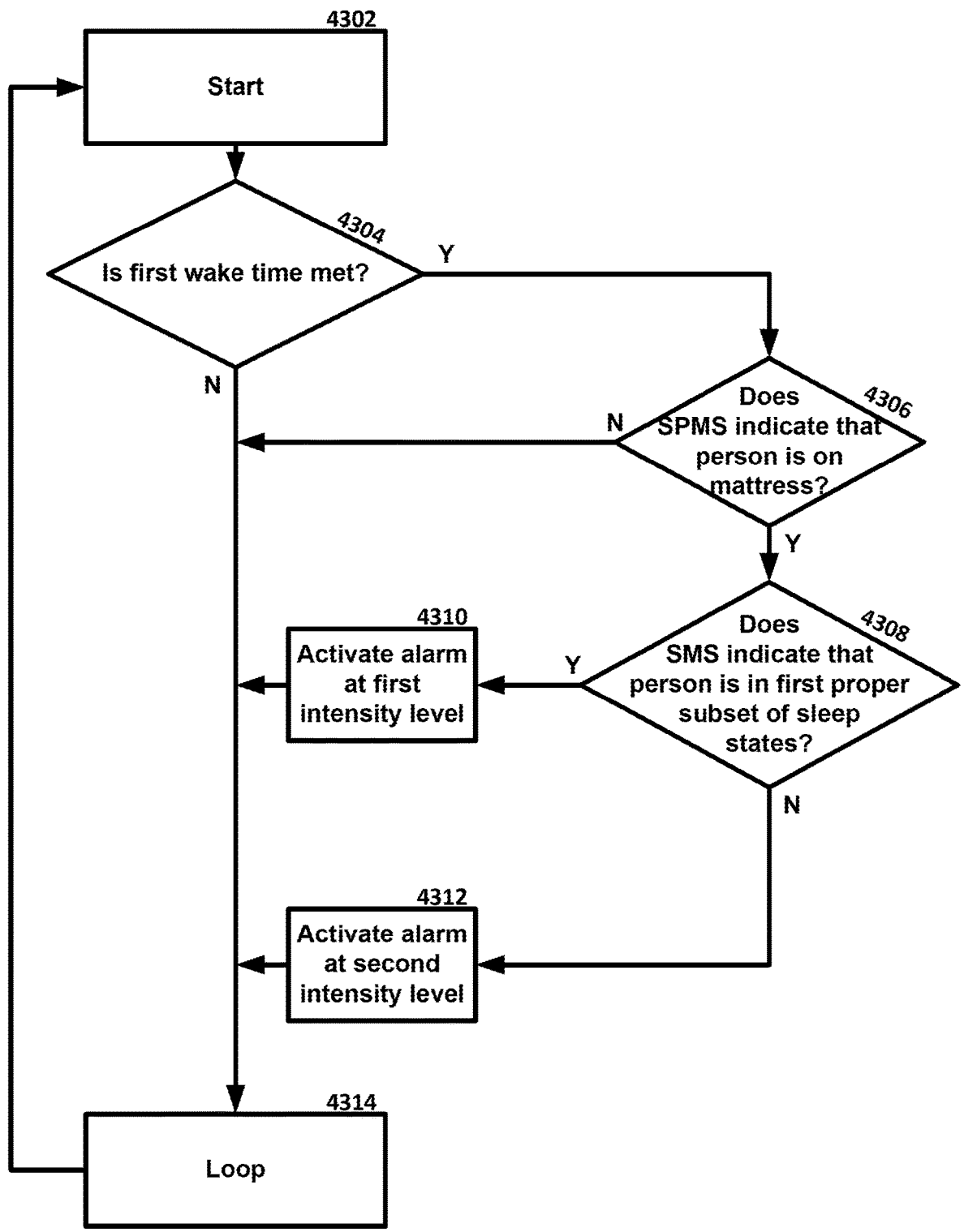
FIG. 43 depicts a flow diagram for a technique for adjusting alarm intensity based on sleep state.

FIG. 43 depicts a flow diagram for a technique for adjusting alarm intensity based on sleep state. In FIG. 43, the technique begins in block 4302 and proceeds to block 4304, where a determination as to whether a wake time, e.g., a wake time that is associated with an identified user or that is associated with a particular side of a mattress, has been met may be made. If it is determined that the wake time has not been met, then the technique may proceed to block 4314 and then back to block 4302. If it is determined in block 4304 that the wake time has been met, then the technique may proceed to block 4306, in which a further determination may be made as to whether a sleeper presence monitoring system indicates that a person is on a side of the mattress associated with an alarm that is to be activated due to the wake time being met. If it is determined in block 4306 that a person is not located on that side of the mattress, then the technique may proceed to block 4314 and then back to block 4302. If it is determined in block 4306 that a person is located on that side of the mattress, then the technique may proceed to block 4308, in which a determination may be made as to whether a sleep monitoring system indicates that the person is in a sleep state in a proper subset of sleep states determinable by the sleep monitoring system. For example, the sleep monitoring system may be able to determine whether the person is in an awake state, a light sleep state, a deep sleep state, or a random eye movement (REM) sleep state, and the proper subset of sleep states may include just the light sleep state. If it is determined in block 4308 that the person is in a sleep state in the proper subset of sleep states, then the technique may proceed to block 4310, in which the wake-up alarm system may activate an alarm associated with the side of the mattress on which the person is located at first intensity level, e.g., a low intensity level. Conversely, if it is determined in block 4308 that the person is in a sleep state that is not in the proper subset of sleep states (or that is in a different, non-overlapping proper subset of sleep states), such as, in this example, a deep sleep state or a REM sleep state, then the technique may proceed to block 4312, in which the alarm may be activated with a second intensity level, e.g., a higher intensity level that the first intensity level. In some such implementations, the first intensity level and the second intensity level may correspond to different alarm devices, e.g., the first intensity level may involve activating a haptic feedback device for a vibrational alarm, whereas the second intensity level may involve activating a speaker for an audible alarm or potentially activating both the speaker and the haptic device.

In some implementations, a wake-up alarm system may be configured to perform "interventions" that may potentially allow co-sleepers to sleep more peacefully together. For example, the wake-up alarm system may be briefly activated to attempt to provoke a sleeper to shift positions, which may cause that sleeper to, for example, stop snoring or perhaps stop tossing and turning, which may improve the sleep of another sleeper in the bed.

Figure 44:
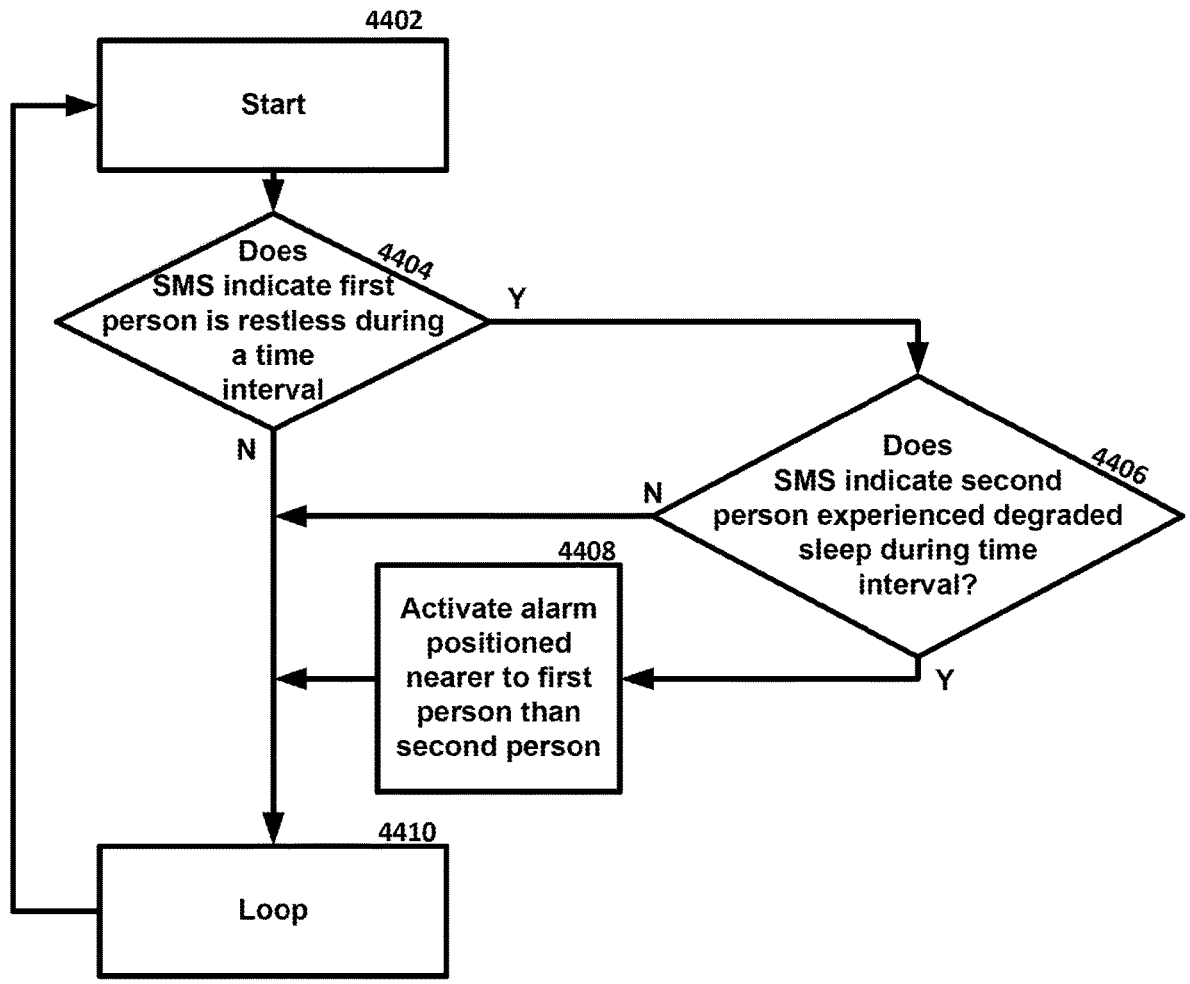
FIG. 44 depicts a flow diagram for a technique for using a wake-up alarm system to improve sleep quality for people sleeping in a bed equipped with the wake-up alarm system.

FIG. 44 depicts a flow diagram for a technique for using a wake-up alarm system to improve sleep quality for people sleeping in a bed equipped with the wake-up alarm system. The technique may begin in block 4402 and then proceed to block 4404, in which a determination may be made as to whether data from a sleep monitoring system indicates that a first person in the bed is restless, e.g., moving frequently, tossing and turning (as may be evidenced by pressure data from pressure sensors indicating peak pressures that shift back and forth between pressure sensors on one side of the bed), etc. If the determination in block 4404 is that the first person is not restless, then the technique may proceed to block 4410 before returning to block 4402. If the determination in block 4404 is that the first person is restless, however, then the technique may proceed to block 4406, where a different determination may be made as to whether a second person in the bed is experiencing degraded sleep quality during the same interval in which the first person is identified as being restless. For example, if the second person is identified as also being restless, this may be treated as being indicative of poor sleep quality. In such cases, it may be difficult to discern which of the two sleepers is causing the other to be restless—in such cases, the sleep history of each sleeper, as determined by the sleep monitoring system, may be reviewed by the wake-up alarm system to determine which of the two sleepers started experiencing restless sleep first and treat that person as the sleeper that is causing the other sleeper to be restless. In some other or additional implementations, the sleep history of each sleeper may be analyzed to determine if there is a temporal correlation of one sleeper's movements with respect to the other sleeper's movements. For example, if the sleep data for one sleeper indicates movements that are similar in time to the other sleeper's movements but that are also frequently lagging behind that other sleeper's movements, this may be viewed as indicative that the other sleeper's movements are causing that sleeper's movements and therefore causing that sleeper to be restless. Another factor that may be analyzed by a sleep monitoring system/ wake-up alarm system is the amount of movement of each sleeper within a given time period—for example, if one sleeper is much more active than the other, the less active sleeper's restlessness (if any) may likely be attributable to the more active sleeper's movements, and steps may be taken to try and cause the more active sleeper to shift positions.

If it is determined in block 4406 that the second person is not experiencing degraded sleep quality, then the technique may proceed to block 4410 before returning to block 4402. If it is determined in block 4406 that the second person is experiencing degraded sleep quality, then the technique may proceed to block 4408, where an alarm positioned nearer to the first person than the second person, e.g., on the side of the mattress on which the first person is located, may be activated in an effort to provoke some change in the first person's behavior. For example, the alarm may have a haptic device that is pulsed rapidly for several short intervals or, in some implementations, the alarm may include a speaker and the wake-up alarm system may cause spoken instructions to be provided to the restless sleeper, e.g., "move over," "stop tossing," etc., as people are sometimes subconsciously responsive to spoken instructions even when sleeping. The technique may then proceed to block 4410 before returning to block 4402. It is to be understood that a similar process may be practiced in parallel for the other sleeper in the bed, e.g., when the second sleeper is restless and impacting the sleep quality of the first sleeper, the same steps may be taken with the roles reversed.

Figure 45:
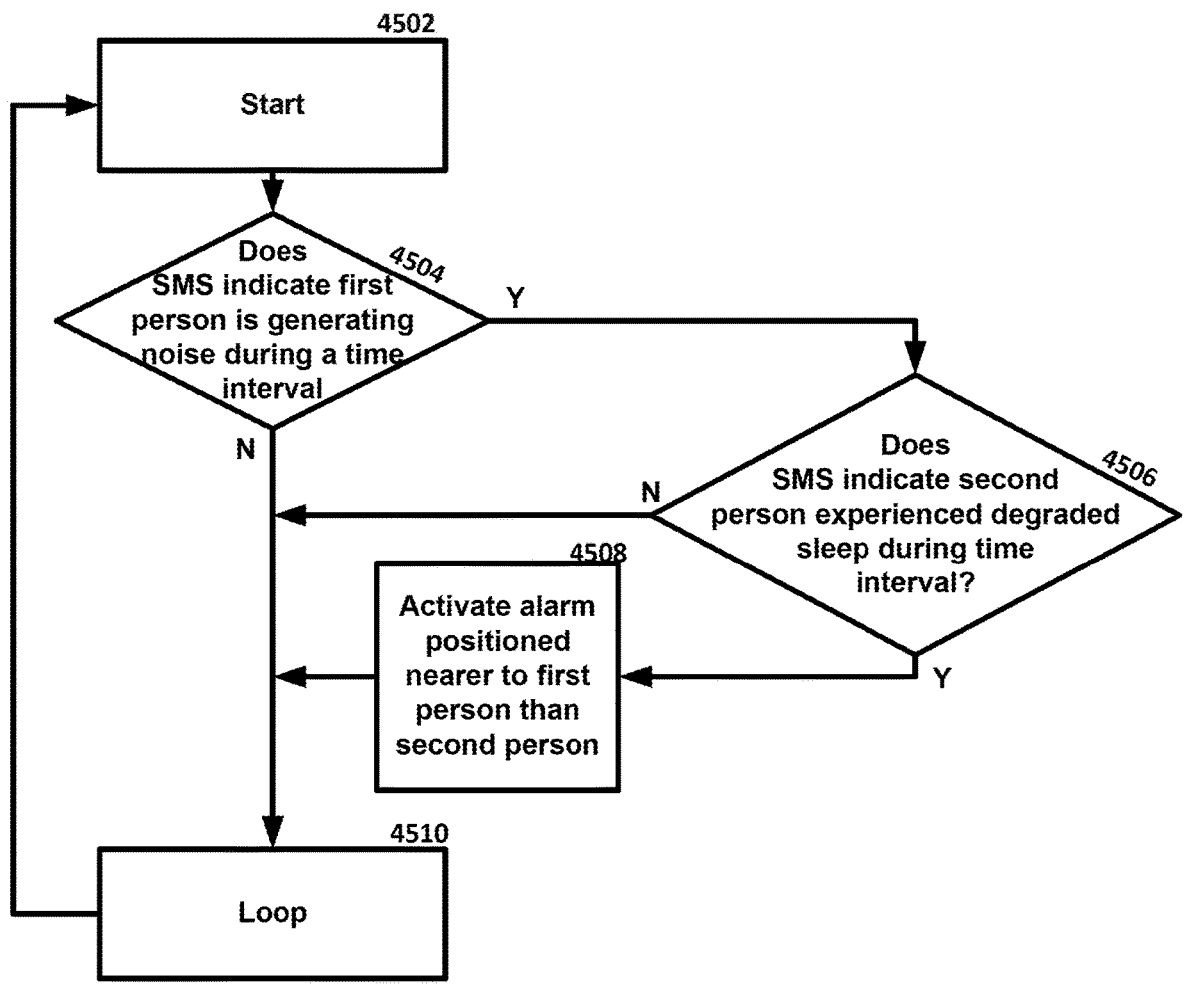
FIG. 45 depicts a flow diagram of a technique similar to the technique of FIG. 44, except that the technique is adapted for dealing with sleep disturbances caused by snoring.

FIG. 45 depicts a flow diagram of a technique similar to the technique of FIG. 44, except that the technique is adapted for dealing with sleep disturbances caused by snoring. The technique may begin in block 4502, and then proceed to block 4504, where a determination may be made as to whether a first person in the bed is snoring. For example, a sleep monitoring system may include microphones that are able to measure the sound levels near each sleeper—if the microphones near one sleeper detect levels of noise corresponding to the level of noise that may be expected when someone is snoring, then the sleep monitoring system may indicate that such a sleeper is snoring.

If it is determined in block 4504 that the first person is not snoring, then the technique may proceed to block 4510 before returning to block 4502. However, if it is determined in block 4504 that the first person is snoring, then the technique may proceed to block 4506, where a different determination may be made as to whether a second person in the bed is experiencing degraded sleep quality during the same interval in which the first person is identified as snoring. If it is determined in block 4506 that the second person is not experiencing degraded sleep quality, then the technique may proceed to block 4510 before returning to block 4502. If it is determined in block 4506 that the second person is experiencing degraded sleep quality, then the technique may proceed to block 4508, where an alarm positioned nearer to the first person than the second person, e.g., on the side of the mattress on which the first person is located, may be activated in an effort to provoke some change in the first person's behavior, e.g., to goad the first person to shift positions into a position where they are no longer snoring or no longer snoring as loudly. It is to be understood that a similar process may be practiced in parallel for the other sleeper in the bed, e.g., when the second sleeper is snoring and impacting the sleep quality of the first sleeper, the same steps may be taken with the roles reversed.

Wake-up alarm systems may also include functionality that may assist people in falling asleep, in addition to assisting in rousing people from sleep. For example, if a wake-up alarm system includes haptic devices, then the haptic devices may be activated in patterns designed to encourage a person to fall asleep. By way of further example, a haptic device may be provided with a signal that causes the haptic device to slowly oscillate between higher and lower intensity output over time. The frequency of this oscillation may be chosen to be at a value that is based on a typical respiratory rate of a sleeping person, which is typically lower than the person's respiration rate while awake. The human body has a tendency to synchronize its breathing with such stimuli, and the closer a person's respiration rate is to a typical sleeping respiration rate, the more likely it is that the person will fall asleep. Thus, such vibratory devices may be used to lull a person into a more sleep-receptive state. Wake-up alarm systems with speaker-type alarm devices may alternatively, or additionally, cause the speakers of the alarms to emit white noise, such as static, recordings of rain drops, or other similar audio output to further assist sleepers in falling asleep. This may be done in place of or in tandem with the vibrational stimuli discussed herein. Once a person has fallen asleep, as determined by a sleep monitoring system component, during such white noise emission, the white noise may be optionally stopped.

Figure 46:
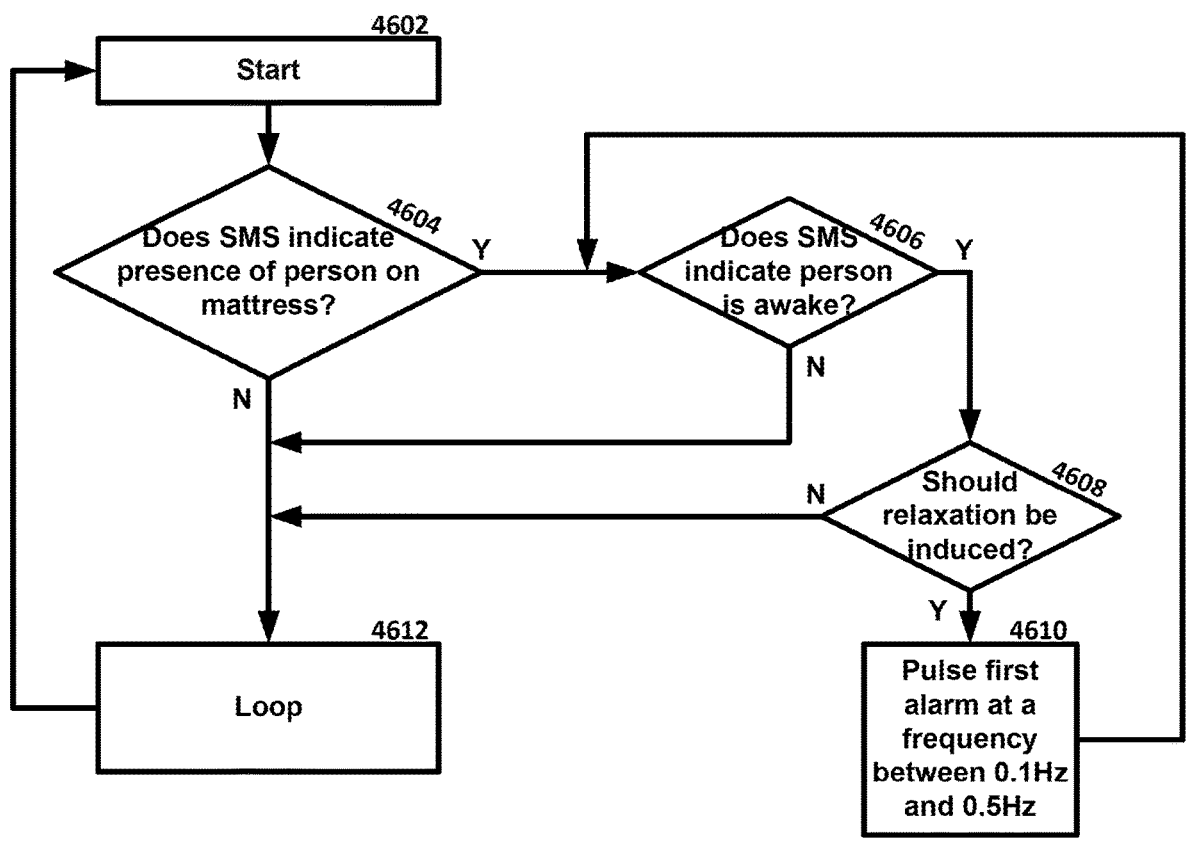
FIG. 46 depicts a flow diagram of a technique for using a wake-up alarm system to encourage a person to fall asleep.

FIG. 46 depicts a flow diagram of a technique for using a wake-up alarm system to encourage a person to fall asleep. The technique may begin in block 4602 and then proceed to block 4604, where a determination may be made as to whether data from a sleeper presence monitoring system indicates that a person is located on a particular side of a bed mattress. If it is determined in block 4604 that no person is present on that side of the mattress, then the technique may proceed to block 4612. If, however, it is determined in block 4604 that a person is present on that side of the mattress, then a further determination may be made in block 4606 as to whether that person is in an awake sleep state. If it is determined in block 4606 that the person is asleep, then the technique may proceed to block 4612 before returning to block 4602. If it is determined in block 4606 that the person is still awake, then the technique may proceed to block 4608, in which a determination may be made as to whether relaxation should be induced, i.e., determine if the wake-up alarm system should be used to try and encourage the person to fall asleep. Such a determination may be based on any of a variety of factors, e.g., based on what time of day it is, based on how long the person has been in bed, based on whether an input is received from the person indicating that they would like to fall asleep, etc.

If it is determined in block 4608 that relaxation should not be induced, then the technique may proceed to block 4612 before returning to block 4602. However, if it is determined in block 4608 that relaxation should be induced, then the technique may proceed to block 4610, in which an alarm that is in close proximity to the person may be activated as discussed above, e.g., activated in an oscillating or pulsating manner. In some such implementations, the frequency of the oscillation or pulsation may be between approximately 0.1 Hz and 0.5 Hz, which may correlate with average human respiratory rates while sleeping. The technique may then return to block 4606; once the person is registered as having fallen asleep, the alarm may be deactivated.

Figure 47:
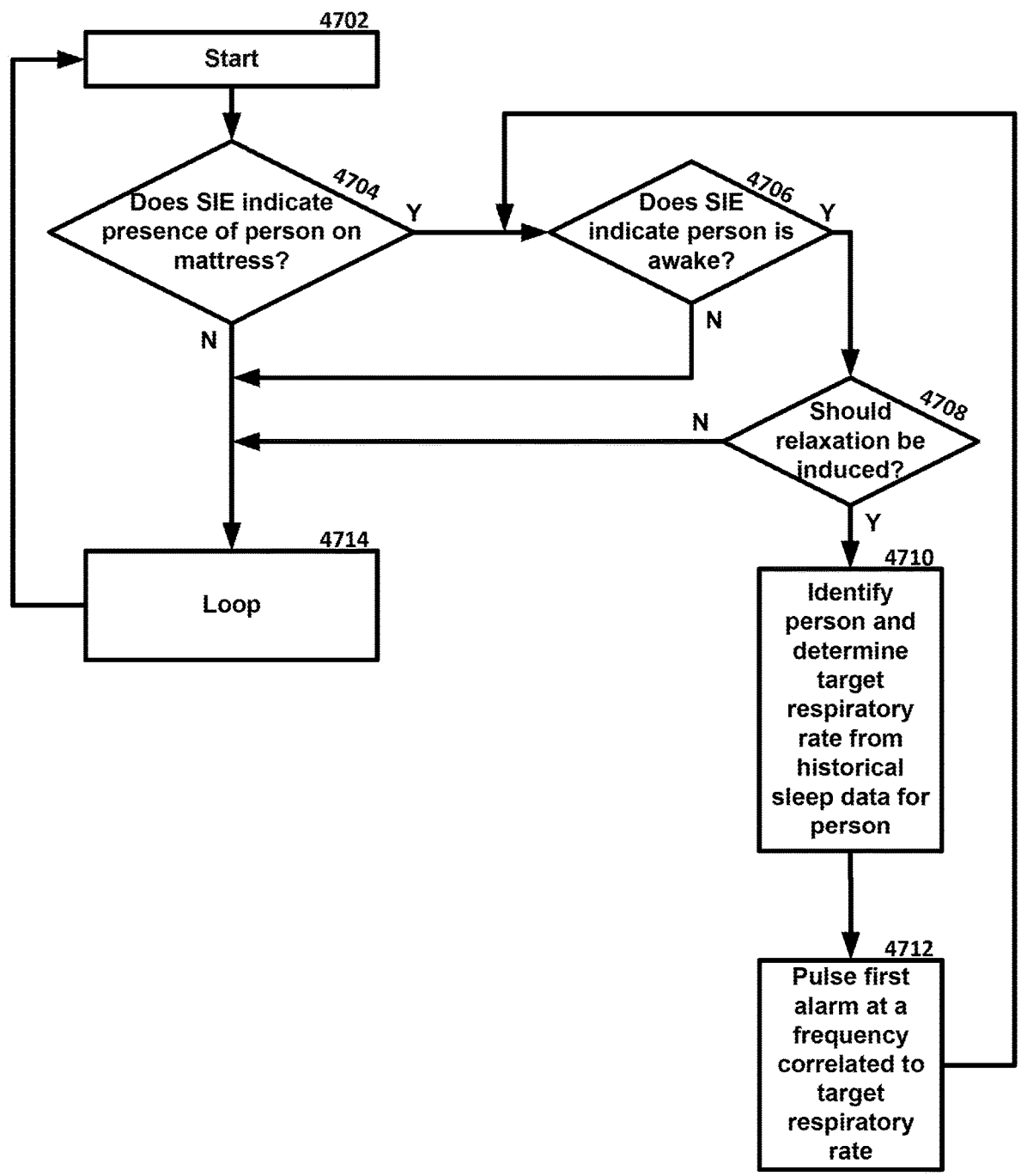
FIG. 47 depicts a flow diagram of another technique for using a wake-up alarm system to encourage a person to fall asleep.

FIG. 47 depicts a flow diagram of another technique for using a wake-up alarm system to encourage a person to fall asleep. The technique may begin in block 4702 and then proceed to block 4704, where a determination may be made as to whether data from a sleeper identification system indicates that a particular person is located on a particular side of a bed mattress. If it is determined in block 4704 that no person is present on that side of the mattress, then the technique may proceed to block 4714. If, however, it is determined in block 4704 that the particular person is present on that side of the mattress, then a further determination may be made in block 4706 as to whether that person is in an awake sleep state. If it is determined in block 4706 that the person is asleep, then the technique may proceed to block 4714 before returning to block 4702. If it is determined in block 4706 that the particular person is still awake, then the technique may proceed to block 4708, in which a determination may be made as to whether relaxation should be induced, i.e., determine if the wake-up alarm system should be used to try and encourage the person to fall asleep. Such a determination may be based on any of a variety of factors, e.g., based on what time of day it is, based on how long the person has been in bed, based on whether an input is received from the person indicating that they would like to fall asleep, etc.

If it is determined in block 4708 that relaxation should not be induced, then the technique may proceed to block 4714 before returning to block 4702. However, if it is determined in block 4708 that relaxation should be induced, then the technique may proceed to block 4710, in which historical sleep data for that particular person may be used to determine a target respiratory rate. For example, if the person's historical sleep data indicates that their sleeping respiration rate is 0.4 Hz, then the target respiratory rate may be set to 0.4 Hz, or some other rate that correlates with the person's respiratory rate as evidenced from the historical sleep data. After the determination of the target respiratory rate, the technique may proceed to block 4712, in which the alarm may be pulsed at the target respiratory rate frequency. The technique may then return to block 4406; the alarm may be deactivated once the person is identified as having fallen asleep.

in which an alarm that is in close proximity to the person may be activated as discussed above, e.g., activated in an oscillating or pulsating manner. In some such implementations, the frequency of the oscillation or pulsation may be between approximately 0.1 Hz and 0.5 Hz, which may correlate with average human respiratory rates while sleeping. The technique may then return to block 4706; once the person is registered as having fallen asleep, the alarm may be deactivated.

Sleep Monitoring System

As noted above, the sleep monitoring sensor apparatus (with or without wake-up alarm components) may be communicatively connected with a sleep monitoring system that may collect global sensor data from the sleep monitoring sensor apparatus and then analyze it to a) determine if the data suggests that there are multiple sleepers and b) extract extracted sensor data that is associated with different sleepers from the global sensor data.

The global sensor data that is received from the sleep monitoring sensor apparatus may be analyzed in any of a number of ways to determine if there are data from multiple sleepers present in the global sensor data and, if so, which data should be associated with each of those sleepers. As discussed earlier, in one technique, independent component analysis (ICA) may be applied to the global sensor data in order to extract extracted sensor data for each of two or more people who may be asleep in a bed that is being monitored by a sensor mesh of a sleep monitoring sensor apparatus. ICA is an analysis technique that may be applied to data sets obtained from multiple sensors that are used to measure physical phenomena attributable to two or more independent sources; ICA allows the signal arising from each independent source to be extracted out from the multiple-sensor data set. The ICA technique generally requires that the data to which it is applied have a non-Gaussian distribution and that the sources, as noted above, be independent of one another. In the context of people sleeping together in the same bed, each person serves as a separate independent input source to the sensors of the sleep monitoring sensor apparatus; the movements of each person are also generally non-Gaussian. This makes the global sensor data from a sleep monitoring sensor apparatus particularly well-suited to analysis using ICA techniques.

For example, consider the sleep monitoring system of FIG. 1, in which the sleep monitoring sensor apparatus 104 includes three sensors 116 and is used to monitor the sleep behavior of two separate sleepers, the first sleeper 106 and the second sleeper 108. If these three sensors 116 are, for example, pressure sensors, then each sensor 116 may register pressure changes caused by movements of both the first sleeper 106 and the second sleeper 108. The left-most sensor 116 may register pressure changes primarily caused by the first sleeper 106, with some minor contributions caused by the second sleeper 108, and the right-most sensor 116 may register pressure changes primarily caused by the second sleeper 108, with some minor contributions caused by the first sleeper 106. The middle sensor 116 may, however, register pressure changes from both the first sleeper 106 and the second sleeper 108 in relatively equal fashion (or at least in a less biased manner than the left/right sensors 116 do).

Figure 48:
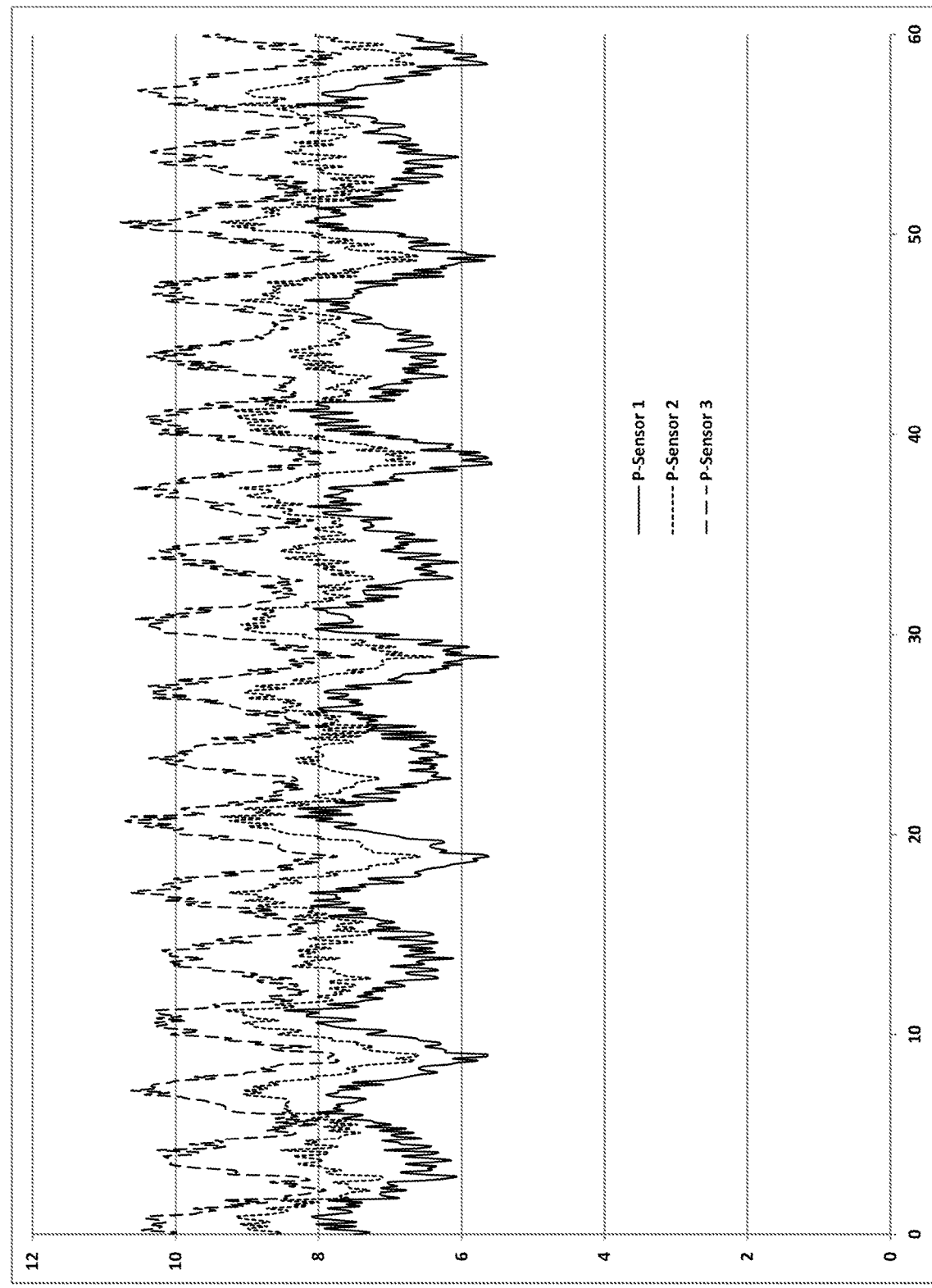
FIG. 48 depicts an example 60-second data segment of global sensor data that may be theoretically be obtained by a sleep monitoring sensor apparatus.

FIG. 48 depicts an example 60-second data segment of global sensor data that may be theoretically be obtained by the sleep monitoring sensor apparatus 104 (it is to be understood that the data in this example and other examples discussed herein, unless otherwise indicated, is simulated data and is not based on actual measured data). Three data traces are shown, each corresponding to measurements from a different one of the three sensors 116. "P-sensor 1" refers to the left-most sensor 116 in FIG. 1, "P-sensor 2" refers to the middle sensor 116 in FIG. 1, and "P-sensor 3" refers to the right-most sensor 116 in FIG. 1. Since the sensors 116 in this example are pressure sensors, they may be used to obtain information that is indicative of breathing rate and, potentially, heart rate of the first sleeper 106 and the second sleeper 108.

By applying ICA to the three sensor data streams in the global sensor data shown in FIG. 48, first extracted sensor data for the first person 106 and second extracted sensor data for the second person 108 may be extracted from the global sensor data. The term "sensor data stream" of a sensor (or sensors) refers to the data or output signal that is produced by that sensor (or sensors) over a period of time. This output may be a raw, unprocessed signal, or may be a processed signal, e.g., one that has been filtered, scaled, and/or converted into a meaningful measurement value. It may include present data and/or past data, e.g., be stored in memory and then accessed later. Thus, the global sensor data may be viewed as including sensor data streams from all of the sensors in the sensor mesh, although subsets of such sensor data streams may be utilized at various times in the techniques discussed herein. The global sensor data may also be viewed as a single sensor data stream in some implementations. Sensor data streams may take the form of data structures stored in memory that organize the sensor data, for example, as an array where the sensor data generated during time t1 is stored in a determinable location compared to the sensor data generated during time t2, and so forth.

Figure 49:
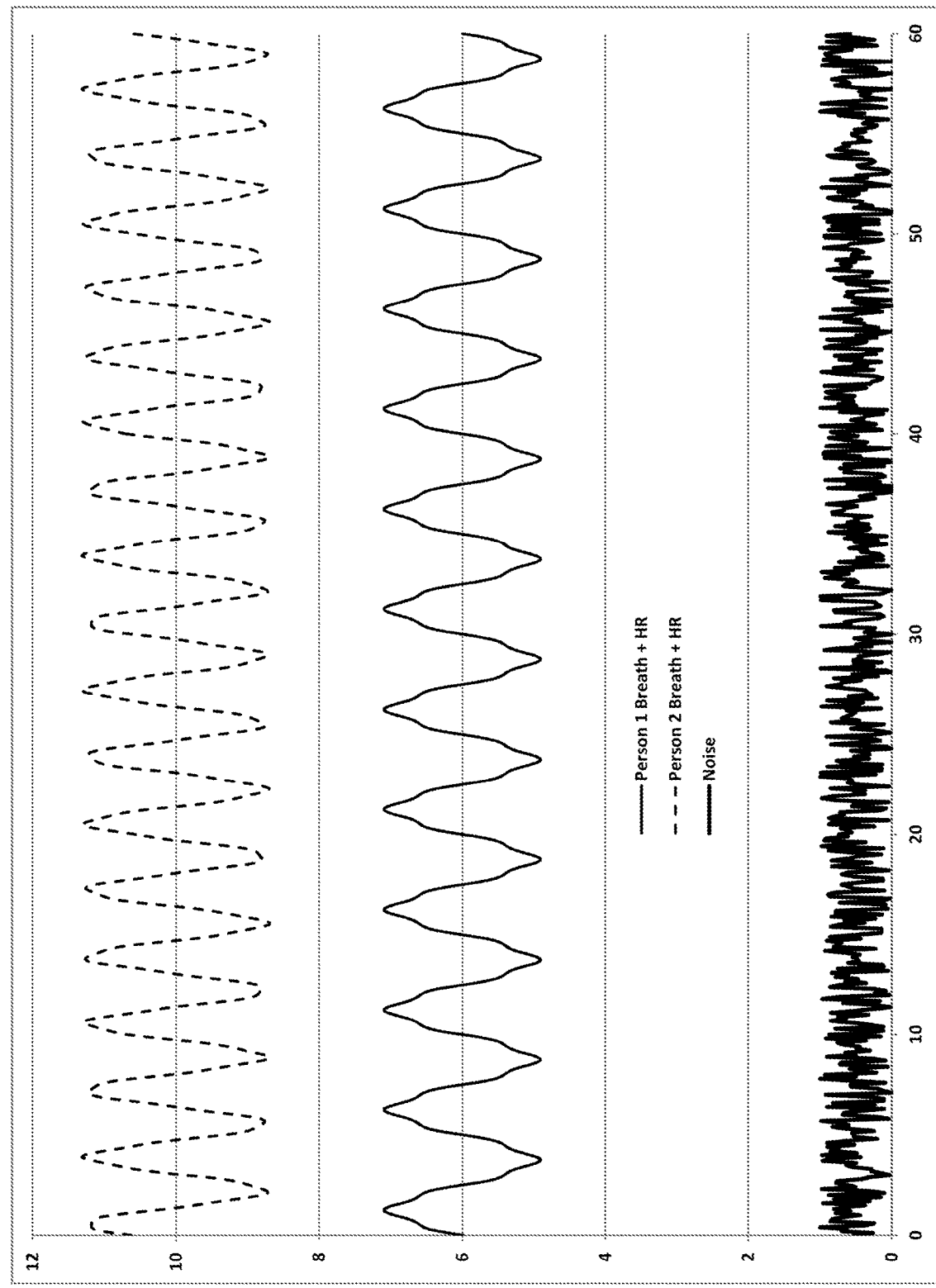
FIG. 49 depicts a notional example of how such extracted signals could potentially look with respect to simulated data such as that represented in FIG. 48.

In ICA, data from a multitude of different sensors may be processed to extract out a corresponding number of different independent source signals. For example, if data from 16 sensors is subjected to ICA, 16 different independent source signals may be extracted—some of these independent source signals may be representative of data that is actually attributable to separate sleepers, but some other independent source signals may be attributable to noise or other sources not of interest. Thus, if a mesh of 16 pressure sensors is used to monitor the breathing rates of two different sleepers in a bed, ICA may yield sixteen independent signals, two of which may have dominant frequencies that are in the "normal" expected range for respiratory rates and that may have some of the largest amplitudes evident in the sixteen independent signals. These two independent signals may thus be viewed as indicative of two independent breathing rate signals. The remaining 14 independent signals may represent other biometric or physiological phenomena, such as heart rate, or may represent different components of random noise. If ICA is used, the "extra" independent signals that are produced, if any, may be discarded or otherwise ignored in some implementations. FIG. 49 depicts a notional example of how such extracted signals could potentially look with respect to simulated data such as that represented in FIG. 48, although it is to be understood that the data shown in FIG. 49 is also simulated and not the result of ICA analysis of the data shown in FIG. 48. FIG. 49, however, does demonstrate that there are three independent source signals, one each for each of the sensors in this example, and that two of the independent source signals have higher amplitudes and very identifiable waveform characteristics that are indicative of the physiological metrics of two sleepers. The third independent waveform, which is identified as "noise," is of a lower magnitude and does not appear to characterize a physiological metric; this third independent source signal may be discarded by the sleep monitoring system or, in some implementations, further analyzed. In some implementations, especially those with larger numbers of sensors, there may be many independent source signals that may be extracted as part of an ICA analysis; some of these signals may be attributable to physiological phenomena, such as breathing or heartbeats. Others, however, may be attributable to other independent sources, such as independent sources in the environment (such as vibrations or sounds in the ambient environment), or noise. In some implementations, the sleep monitoring system may perform ICA even when it is determined that no person is present in the bed, e.g., when the sensor mesh provides data indicating that no person is present, in order to obtain a baseline of "ambient" independent signals. For example, it may be the case that a sleep monitoring system may register vibrations caused by passing vehicles or by the operation of machinery nearby, such as an air conditioner unit or a pool pump. ICA may extract independent source signals that correspond to the signals produced by such equipment, but it may be difficult to differentiate such source signals from legitimate physiologically-sourced independent source signals. Thus, in some implementations, the sleep monitoring system may monitor for such independent source signals during periods when it is determined that there are no people present. The sleep monitoring system may then characterize the independent source signals that are obtained during such periods and classify them as being attributable to environmental effects or simply noise. If independent source signals are later produced using ICA when there is a person actually being monitored, the sleep monitoring system may ignore the independent source signals that sufficiently correspond in frequency and/or magnitude to those independent source signals that were previously classified as environmental effects or noise. The remaining independent source signals may be analyzed, as desired, to determine if any of them exhibit characteristics indicative of a physiological metric.

The independent signals produced through ICA analysis are not inherently tied to any particular sensor in the group of sensors that produced the data analyzed in the ICA analysis, and thus may not provide insight as to the spatial location of the independent source with respect to the sensor mesh. However, the sensor data streams from each of the sensors in the sensor mesh may be compared against the determined independent source signals to determine which of the sensor data streams has the greatest contribution from each of the independent source signals. If an independent source signal is determined to make the greatest contribution to a particular sensor data stream, then the sensor that produced that sensor data stream may be determined to be the sensor that is closest to the actual independent source of that determined independent source signal. For example, if ICA yields two independent source signals that are identified as a first respiratory rate of 12 breaths per minute and a second respiratory rate of 18 breaths per minute, then the sensor that has the sensor data stream that most strongly exhibits a 12 breaths per minute component may be assumed to be positioned closest to the actual source of that 12 breaths per minute signal, i.e., the torso of the person breathing at that rate. Similarly, the sensor that has the sensor data stream that most strongly exhibits an 18 breaths per minute component may be assumed to be positioned closest to the actual source of that 18 breaths per minute signal, i.e., the torso of the other person.

In some implementations, the sleep monitoring system may first make a determination as to whether there is more than one person in a bed before attempting to perform ICA or another multi-person data extraction technique. In some such implementations, if only one person appears to be present in the bed, then the sleep monitoring system may forego attempting to extract sensor data for multiple people. Such determinations as to the presence of multiple sleepers may be made in a number of ways. For example, as discussed in the example below, frequency analysis of global sensor data may indicate that there are two different respiratory rates that appear to be evident in the global sensor data, thereby indicating the presence of two different sleepers. In another example, pressure sensors or temperature sensors, if used, may indicate two different centers of pressure or temperature that are indicative of two different sleepers.

As discussed above, any of a variety of different signal-extraction techniques may be used to obtain the first extracted sensor data, the second extracted sensor data, and so on. ICA is not the only analysis technique that may be used. For example, another technique that may be used is to identify particular sensor data stream(s) in the global sensor data that are strongly correlated a particular sleeper, and then use that sensor data stream or those sensor data streams as the extracted sensor data for that sleeper. As a more specific example, processing can be applied to the sensor data associated with a first sleeper to identify periods of high motion, as such time periods are likely to be when the interference to the second person's data stream is highest.

One means to identify movement in the first person's data stream is to calculate a running mean square energy value of the raw sensor data over a short time period (e.g., 2 seconds). When this energy exceeds a threshold (which can be determined experimentally by asking people to make movements in a bed, and then assess the energy level associated with that period of time), that will designate a "Person 1 movement period". In the analysis of the data stream associated with the second person's activity, that period of time can then be flagged as "likely to be affected by movement", and can be either removed from the analysis, or the second person data stream values can be replaced with interpolated or zero-valued data. In an alternative embodiment, a movement detector can be applied to the data streams of both people to produce estimates of when movement has occurred. If a movement occurs simultaneously on both data streams, that movement will be ascribed to the person whose data stream has the higher energy value for movement, and the other person will be deemed to have "not moved".

For example, frequency analysis, such as fast Fourier transform analysis or other similar analysis, may be performed on the global sensor data in order to identify sensor data that appears to correspond with one or more breathing rates. Children (greater than 6 months of age) and adult humans typically breath at rates of 10 to 30 breaths per minute. Since breathing rates are typically quite regular, movements associated with breathing may exhibit a marked periodicity that is easily identifiable using frequency analysis. For example, frequency analysis of the global sensor data may indicate that there are two frequency components that are dominant in the 0.17 Hz to 0.5 Hz (10 to 30 cycles per minute) range in the global data, e.g., 0.2 Hz (equal to 12 breaths per minute) and 0.3 Hz (equal to 18 breaths per minute). From this, it may be inferred that there are two people whose breathing movements are being detected by the sensor mesh of the sleep monitoring apparatus sensor. If the breathing rates of co-sleepers are, and remain, sufficiently distinct to allow each to be separately monitored, then such frequency analysis may constitute, in some implementations, the limit of data extraction that may need to be performed in order to obtain at least some sleeper-specific information.

However, if the breathing rates of co-sleepers are very similar, or if the breathing rates of co-sleepers at some point harmonize, it may be difficult to keep the breathing rate data for the co-sleepers segregated. For example, breathing rates for sleepers may vary over time, e.g., in response to dreams, fever, or natural sleep patterns. This may cause, for example, a co-sleeper having a breathing rate of 12 breaths per minute to slowly increase their breathing rate to 18 breaths per minute during an interval where the other co-sleeper that they are sleeping next to might keep a relatively steady breathing rate of 15 breaths per minute. At some point, both of these co-sleepers will have approximately the same breathing rate, and it will not be possible to tell from frequency analysis alone if the observed frequencies indicate, as set forth above, a scenario in which one co-sleeper maintains a steady breathing rate of 15 breaths per minute for the period that is analyzed and the other co-sleeper experiences a breathing rate starting at 12 breaths per minute and rising to 18 breaths per minute for that same period, or a scenario where one co-sleeper maintains a steady breathing rate of 15 breaths per minute for a first portion of that period, followed by an increase in breathing rate to 18 breaths per minute in a subsequent, second portion of that period, and the other co-sleeper experiences a breathing rate that rises from 12 breaths per minute to 15 breaths per minute in the first portion of that period, followed by a steady breathing rate of 15 breaths per minute in the second portion of that period. To address such potential cases, some implementations may take further steps to extract sleeper-specific data.

For example, if particular breathing rates are identified in the frequency analysis as being present, each individual data stream from the sensors in the sensor mesh may be analyzed to determine which individual data stream(s) exhibit the highest magnitude signal for each such identified frequency within the same interval. The sensors producing such highest magnitude signals may generally be the sensors that are closest to the signal source, i.e., the sleeper or portion of the sleeper producing the movement that exhibits the periodicity/frequency of interest. Thus, for example, if two frequencies are identified, e.g., 12 breaths per minute and 18 breaths per minute, the data streams may be analyzed and two sensors may be identified—one that has the highest magnitude signal component at 0.2 Hz (12 breaths per minute) during the same time period from which those frequencies were identified, and the other that has the highest magnitude signal component at 0.3 Hz (18 breaths per minute) during that same time period.

In the case where only one breathing rate frequency is identified in the frequency analysis of the global sensor data, then the individual sensor data streams may be analyzed to determine which of the sensors has the highest magnitude component with that frequency within the same time period. It is highly likely that this particular sensor's location is correlated with the location of a particular one of the co-sleepers. In such situations, one or more other sensor data streams may be identified that also exhibit a signal component having a frequency that correlates with the identified frequency (but that is generally lower in magnitude than the highest-magnitude, earlier-identified sensor data stream). Various rules may be applied to then determine which of these other sensor data streams may be viewed as representative of the location(s) of the other co-sleeper(s).

Figure 50:
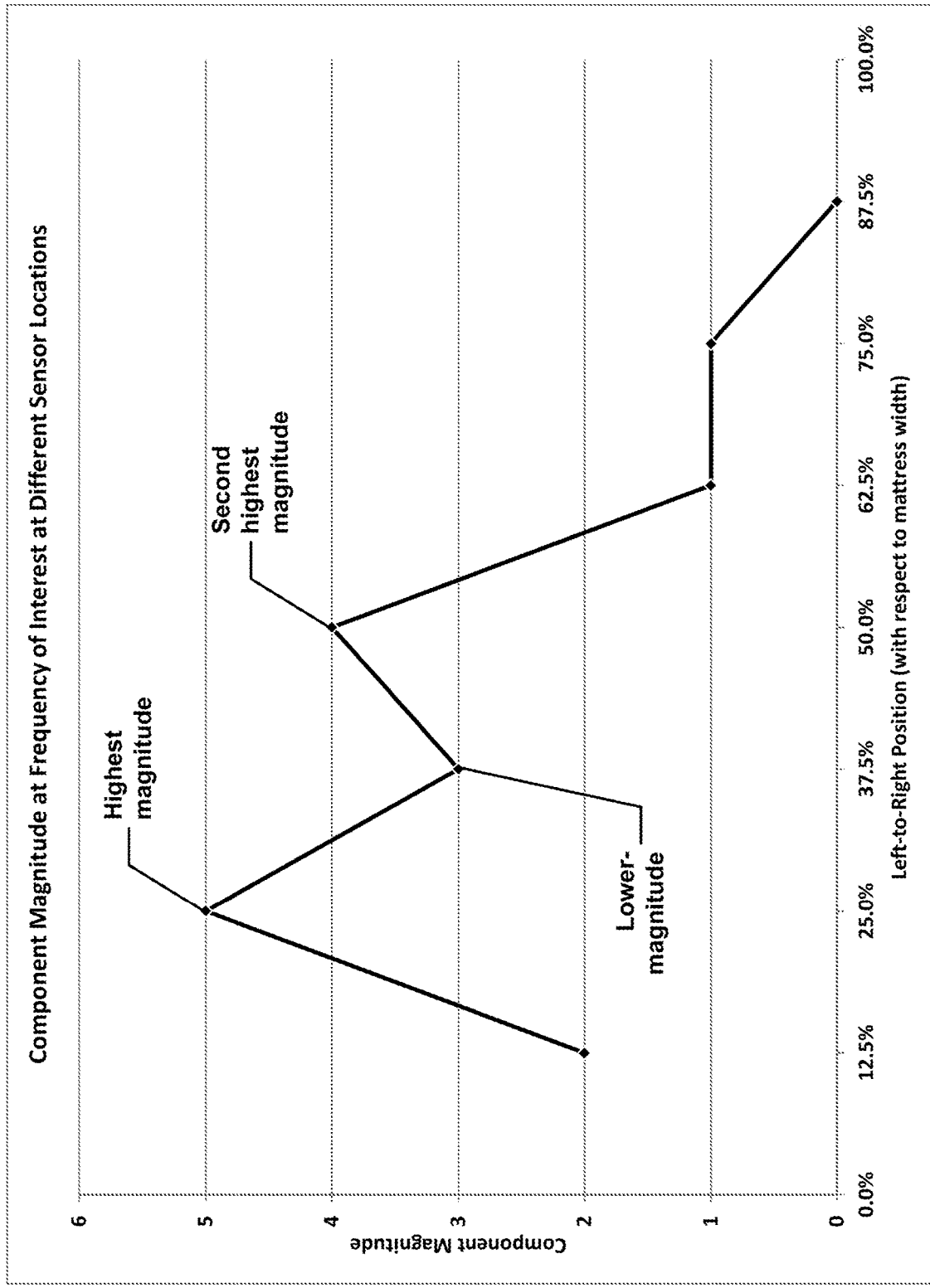
FIGS. 50 and 51 depict hypothetical component magnitudes as a function of left-right sensor positioning on a mattress with respect to a signal component of a particular frequency.

For example, a sensor data stream for that same period of time may be identified that has a second highest-magnitude signal component of that frequency. The location of the sensor that produces the sensor data stream with the second-highest-magnitude signal component of that frequency may, in some implementations, be correlated with the location of a second co-sleeper. Thus, the sensor producing the sensor data stream with the highest-magnitude signal component of that frequency may be associated with one co-sleeper, and another sensor producing the sensor data stream with the second-highest-magnitude signal component of that frequency may be associated with the other co-sleeper. For example, FIG. 50 depicts the relative magnitudes of signal components having the same frequency in a sensor mesh having seven sensors distributed at various transverse locations of a mattress (in this case, the sensors divide the mattress into eighths). As can be seen, the highest magnitude signal component at this frequency occurs at the sensor that is located one quarter of the mattress width in from the left side of the mattress. This sensor location may thus, in some implementations, be viewed as corresponding with the location of the one of the co-sleepers. As can be further seen, the second-highest magnitude signal component at this frequency occurs at the sensor that is located at the middle of the mattress. This second sensor location may thus, in such implementations, be viewed as corresponding with the location of the other co-sleeper.

FIG. 50 depicts hypothetical component magnitudes as a function of left-right sensor positioning on a mattress with respect to a signal component of a particular frequency, e.g., for 0.2 Hz. In the example of FIG. 50, there is at least one sensor with a lower-magnitude signal component at the frequency of interest interposed between the sensors identified as corresponding with the first person and the second person, which may be viewed as indicating that the two identified sensors are actually producing signals measuring two different sources, i.e., sleepers.

Figure 51:
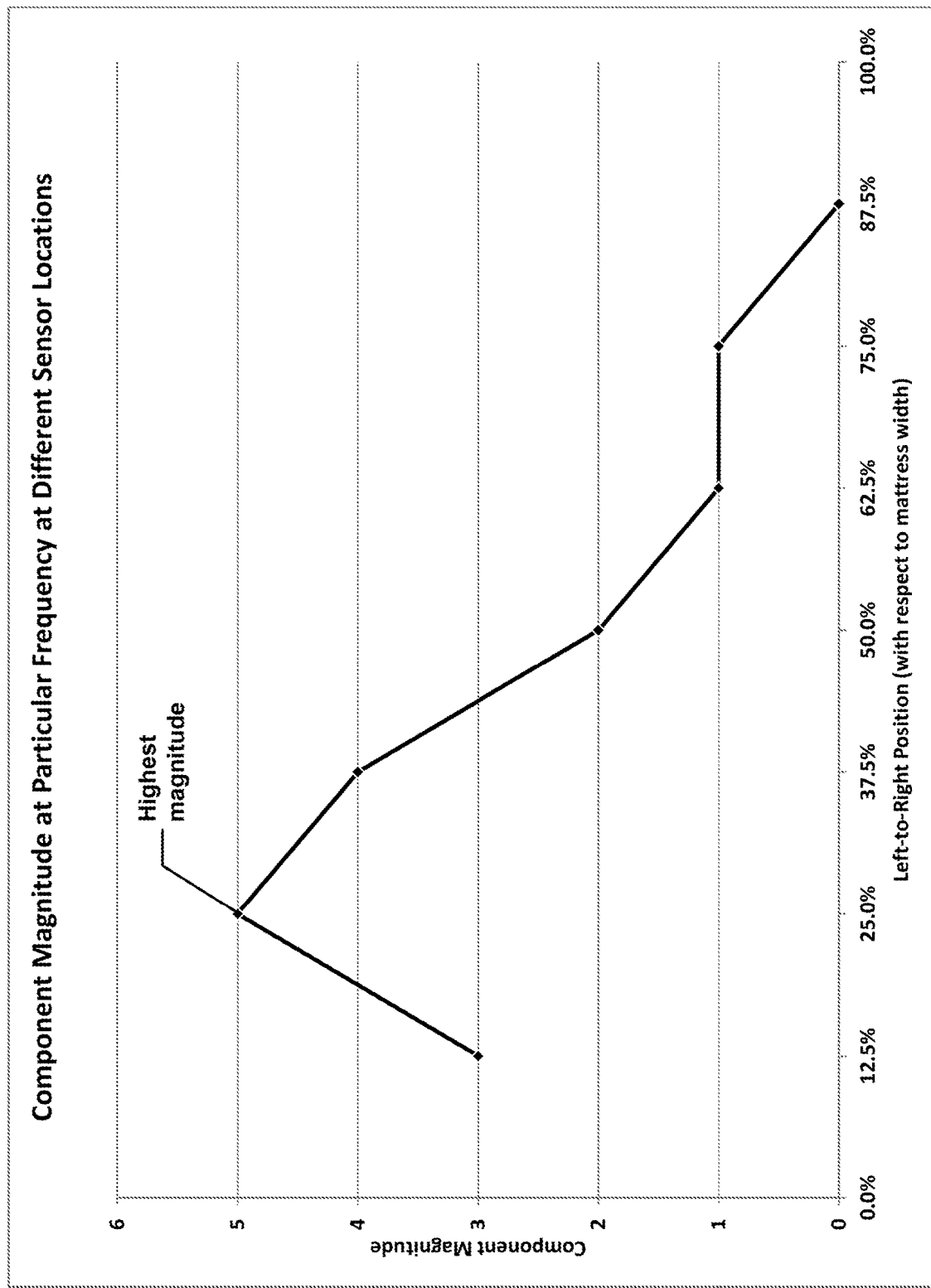

In some cases, two sources/sleepers may be sufficiently close to one another that the highest-magnitude signal component may actually be a poor "representative" signal for either sleeper since inputs from both sleepers may make it difficult to identify data that is particular to either sleeper in such a signal. In such situations, it may be preferable to avoid viewing the data stream from the sensor exhibiting the highest-magnitude signal component at the frequency of interest as representative of either sleeper. Instead, for example, it may be preferable to identify the sensor data streams for sensors on either side of the sensor exhibiting the peak as being representative of each sleeper. For example, in FIG. 51, which is similar to FIG. 50 except that the signal component magnitudes that are depicted are different, there is one clear peak in the indicated magnitudes—at 25% of the mattress width. The sensor at this location, however, may be receiving strong input signals from both sleepers and may thus be a poor candidate sensor to represent either sleeper individually. However, the sensors immediately to the left and right of the highest-magnitude sensor may be better candidates for sensor data streams that represent each sleeper. For example, while both of the neighboring sensors have lower magnitude signal components than the intervening sensor, the signal components of the neighboring sensors may be more biased towards one or the other of the people sleeping in the bed.

Once a particular sensor data stream or sensor data streams have been identified as being associated with a particular sleeper, data from that sensor data stream or streams may be used to generate sleep data for that particular sleeper. It is to be understood that the sleep monitoring system may periodically re-perform an analysis such as the above in order to re-evaluate which sensor data streams are associated with each particular person throughout a sleep session. For example, the sleepers may move about significantly while asleep, e.g., due to discomfort, dreams, or other stimuli, and the sensor data stream(s) that provide the best data quality for each sleeper may change over time in response to such movements, i.e., as the sleepers move from being proximate to one sensor to being proximate to another sensor.

Such periodical re-scanning of sensor data streams to identify the sensor data streams most representative of a particular sleeper may be performed on a regular schedule, e.g., every 5, 10, 15 minutes, or any other regular time interval, or on a data-driven schedule, e.g., if a sensor data stream previously identified as being representative of a particular sleeper starts to exhibit poor data quality (such as no longer providing a signal of sufficient quality to be able to extract a breathing rate and/or heart rate), then the system may re-scan the sensor data streams.

The techniques discussed herein may generally be viewed as techniques that extract sensor data that is associated with different sleepers in a bed. As part of this extraction, artifacts or components that are at least evident or included in the global sensor data and attributable to motions of a first person may be identified and the contribution of such motions to the extracted sensor data for a second person may be reduced. For example, in the case of ICA, the extracted sensor data, e.g., one of the independent source signals that ICA produces, is already generally free of contributions from the other independent source signals produced using ICA. Thus, ICA is a technique that may inherently identify components in the global sensor data that are caused by motion of a first person (a first independent source) and reduce the contribution that those motions or components may make to one or more extracted independent source signals, e.g., second extracted sensor data for a second person. In other implementations, such as when a particular sensor's data stream may be used as the extracted sensor data for a particular person, the identification of components in that extracted sensor data that are attributable to another person, as well as the reduction of the contribution that such components may make to that extracted sensor data, may be done separately from the data extraction process. For example, first extracted sensor data for a first person and second extracted sensor data for a second person may be obtained, e.g., sensor data streams from two different sensors, each positioned proximate to a different one of the two people. Since the sensor data streams are part of the global sensor data, the components in the first sensor data stream/ first extracted sensor data that are attributable to the first person, e.g., a first component, are also present in the global sensor data—for example, a component may be identified in the first extracted sensor data that is much higher in magnitude than related components in other sensor data streams; such a component may be assumed to originate due to movements of the first person. As discussed earlier, a corresponding component, e.g., a second component, may be evident in the second sensor data stream—this second component may be determined to be a sympathetic component that is driven by the first component, e.g., due to having similar timing and/or frequency characteristics and the contribution it makes to the second extracted sensor data may then be reduced, e.g., by averaging or more aggressively averaging the portion of the second extracted sensor data having that sympathetic component, or removing the portion, or performing some other remedial action to reduce the effect that the first person's movements have on the second persons' extracted sensor data.

The above techniques have focused on using the time-varying nature of signals produced by each sleeper as a way of separating out data for each sleeper, either by extracting out the component signals for each person without regard for sensor location or by determining which particular sensor or sensors produce the best signal or signals for each person. In other implementations, non-time-varying signals may also be used to determine which sensor data streams may be associated with each person. In this context, "non-time-varying" is used to refer to signals that do not have a repeating, periodic component. For example, if pressure sensors are used in the sensor mesh of the sleep monitoring sensor apparatus and the sensor mesh is located beneath the sleepers, each sleeper may exert a pressure on the pressure sensors—this pressure may have time-varying aspects, such as may be caused by regular, relatively small-amplitude shifts in pressure due to the person's breathing, as well as non-time-varying aspects, such as the amount of pressure that is exerted by the person's weight regardless of breathing movements. Of course, as the person moves around on the bed during sleep, the non-time-varying aspects may actually vary, but this is not a periodic movement as may be attributed to breathing-related movements, for example. The non-time-varying pressure at a multitude of sensor locations may be used to map out a pressure distribution over the portion of the mattress over which the sensors of the sleep monitoring sensor apparatus are distributed. This pressure distribution may be analyzed to determine localized centers of pressure that are attributable to different sleepers, e.g., each person's body may have its own center of pressure that may be identified in the pressure distribution. For example, if peak pressures are detected at two different transverse sensor locations, then those two locations may be assumed to correlate with the locations of two different sleepers, and sensor data streams from the sensors at those locations, or proximate to those locations, may be associated with the sleeper that is closest, including sensors other than the pressure sensors at those locations.

As discussed above, in some implementations, the extracted sensor data for each sleeper may be processed order to remove artifacts in the extracted sensor data for that sleeper that may be attributable to motions of the other sleeper, i.e., sympathetic movement. Thus, for example, the first extracted sensor data for a first sleeper may include data indicating a period of time during which the first sleeper moved, resulting in the first extracted sensor data exhibiting localized oscillations of a higher frequency than, for example, first extracted sensor data in the same period of time that is driven by breathing-related movements, which may cause oscillations in the extracted sensor data that have a frequency tied to the first sleeper's breathing rate. The movement of the first sleeper may also have caused sympathetic movements in the second sleeper (and/or of the mattress under the second sleeper), which may cause sympathetic localized oscillations in the second extracted sensor data. These sympathetic localized oscillations will be of a lower magnitude than those in the first extracted sensor data due to the natural damping that occurs in a bed mattress, but will occur simultaneously with the driving localized oscillations in the first extracted sensor data, and will potentially have similar frequency characteristics. If such sympathetic components are identified in a given sleeper's extracted data based on driving components produced by another sleeper, they may be corrected in some manner prior to generating sleep data for the given sleeper. For example, in some implementations, such sympathetic components may be replaced by a less noisy signal, e.g., the time segment of the extracted sensor data with the sympathetic component may be replaced with an interpolated, averaged, or splined data segment that effectively removes the sympathetic component or mitigates its effect. In some implementations, the data segment with the sympathetic component may simply be blanked out or removed (thus resulting in a gap in the data).

Figure 52:
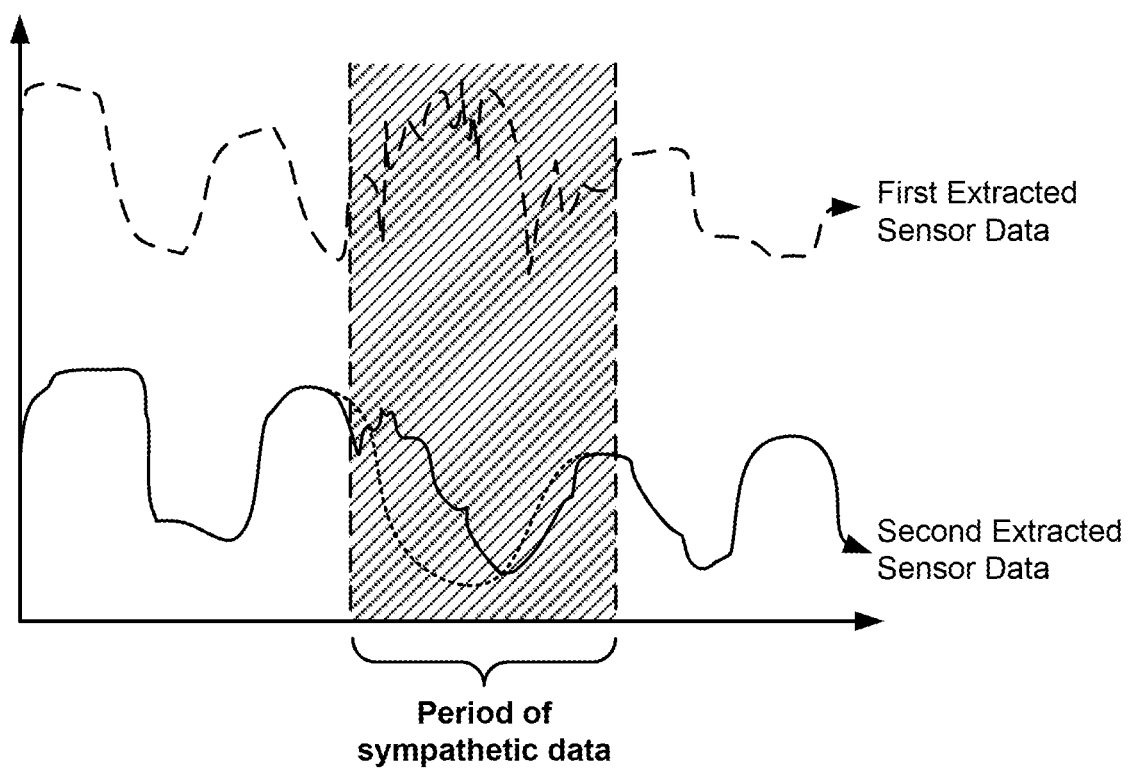
FIG. 52 depicts two example extracted sensor data signals provided herein to illustrate exemplary extracted sensor data signals; these sensor data signals are illustrative and do not represent actual sensor data.

FIG. 52 depicts two example extracted sensor data signals provided herein to illustrate exemplary extracted sensor data signals; these sensor data signals are illustrative and do not represent actual sensor data. As can be seen, in the shaded/ crosshatched period, the first extracted sensor data for a first sleeper experiences a high-frequency component that may, for example, occur in response to the movement of the first sleeper. The second extracted sensor data, which is for a second sleeper, exhibits some sympathetic noise in the same interval that may be attributed to the first sleeper's movement as well. Such noisy data may be blanked out or, as shown in FIG. 52, replaced with interpolated or otherwise smoothed data (dotted lines).

Removing or correcting sympathetic components in a sleeper's extracted sensor data prior to generating the sleep data for that person may be important, as some sleep data, e.g., restlessness/sleep stage/etc. determinations, may be based on the number of instances of gross movement indicated in the extracted sensor data for a person. If such data also includes motion artifacts due to sympathetic movements of that person triggered by motions of another person that they are co-sleeping with, then this may falsely indicate that the person is more restless than they actually are, which may lead to inaccuracies in identifying what sleep stage they are in. By correcting or mitigating such sympathetic components, per the technique discussed above, more accurate sleep data may be generated for each person.

Once the global sensor data has been analyzed and the first, second, etc. extracted sensor data has been extracted from the global sensor data, the first, second, etc. extracted sensor data may be further analyzed to provide sleep data. For example, as noted earlier, pressure data from pressure sensors may be used to provide a measure of a sleeper's breathing rate and potentially heart rate. Pressure data may also be used to measure other motion, such as tossing and turning of the sleeper, gross limb movements, and even getting into/out of bed. If available, extracted sensor data from other sensor types may also be used, e.g., accelerometer, gyroscope, or magnetometer data may be used to monitor for gross limb or body movements, temperature sensors may be used to monitor body temperature, center-of-heat (which may be used in a similar manner to how the center-of-pressure for a person may be used, e.g., to estimate the locations of different sleepers), acoustic sensors may be used to monitor for snoring, and so forth.

The ability to measure temperature, in implementations having temperature sensors, may be leveraged in a number of other ways as well. For example, the sleep monitoring system may determine estimates of proximal and/or core body temperature, which may be used as an additional factor or factors to determine what sleep stage the sleeper may be in at a given time, or which may be used, for example, to track physiological metrics relating to fertility, illness (fever tracking, for example), or circadian rhythm. Such temperature determinations may be approximated based on a distributed temperature map that may be provided by a distributed set of temperature sensors.

Some sleep data may be based on other sleep data. For example, the sleep monitoring system may evaluate what sleep stage a sleeper is in in a given time period or epoch based on, for example, average breathing rate in that time period, variation in breathing rate in that time period, the amount of movement in that time period, the time since the last large or gross movement, the time until the next large or gross movement, and the correlation of breath-to-breath signals within that time period, e.g., how consistent or regular the person's breathing is. As noted earlier, large or gross movements, as used herein, refer to body motions that are not part of normal breathing or heartbeat motions, and also do not include minor movements. Such gross movements are intended to include, however, movements such as limb movements, body repositioning, etc. One non-limiting example of a gross movement is movement of the forearm that results in an acceleration of 0.2 g or greater at the wrist. The time between gross or large movements may be determined in a variety of ways, depending on the particular implementations. In some implementations, such time may be evaluated based on the actual time between a first gross movement and a second gross movement. In other implementations, such time may be more a measure of the number of epochs that occur between such gross movements. Other techniques for quantifying such intervals may be used as well, depending on the particulars of the sleep classifier system that is used. Such parameters may be fed into a classifier stage that combines these parameter values and then determines the most likely sleep stage based on the parameter values, e.g., by multiplying each parameter value by a weighting factor and then adding the products together. A linear discriminant classifier may be used in such a determination, although other classification techniques/systems, such as support vector machines, decision trees, and random forest classifiers may be used in alternative implementations.

The particular sleep stage that a sleeper is in may be determined according to commonly accepted sleep stage paradigms, e.g., a Wake stage (where the sleeper is not asleep at all), as well as an N1 stage, an N2 stage, an N3 stage, and a REM stage. In some cases these stages may be combined and or renamed to make it easier for the operator to understand the sleep data that is collected. For example, N3 may be referred to as a "deep sleep" stage, and N1 and N2 may be combined into a single stage referred to as a "light sleep" stage. Thus, in some implementations, determinations may be made between an awake or wake stage, a light sleep stage, a deep sleep stage, and a REM sleep stage.

Different kinds of sleep data may be determined using different techniques with the extracted sensor data for a given individual. For example, signal components indicating significant movement, e.g., tossing and turning, limb movement, etc., of a sleeper may be identified by tracking signal components exhibiting high-frequency energy, which may differentiate such signal components from signal components caused by low-amplitude movements of the sleeper, such as breathing or cardiovascular movements, or by using an energy operator such as the Teager energy operator. Breathing rate may be determined from extracted sensor data for a person by performing spectral analysis on the extracted sensor data for the time period of interest and looking for a dominant frequency that correlates with a range of expected breathing rates, or by applying an adaptive filter to the extracted sensor data, where the adaptive filter uses parameters that reflect the dominant frequency in the extracted sensor data in the time period of interest.

Since the sleep monitoring system is able to separately track extracted sensor data for each sleeper, the sleep monitoring system can provide and track sleep data that is particular to each sleeper. The sleep monitoring system may also, based on such information, provide personalized recommendations and other feedback to each sleeper. The sleep monitoring system may also be configured to perform other actions in response to certain scenarios. For example, the sleep monitoring system may be communicatively connected with home automation networks or smart appliances and may be configured to send activation signals to different external devices, e.g., lights, powered blinds or window coverings, smart windows, water heaters, powered door locks, hot water recirculation pumps, coffee makers, thermostats, home entertainment systems, etc., to cause such a device or devices to turn on or off or otherwise change state in response to cues in a person's sleep data. For example, if the sleep data includes sleep stage data and it appears that such sleep stage data indicates that the sleeper is about to wake up, the sleep monitoring system may cause the thermostat to change to a higher temperature setting and may cause a coffee maker to start brewing a cup of coffee. Conversely, if the sleep monitoring system detects that a sleeper or sleepers have gone to sleep from an awake state, the sleep monitoring system may send a signal to a thermostat to decrease the thermostat setting to a more energy-efficient mode; the sleep monitoring system may also send a signal to a smart lock to cause the smart lock to transition to a locked state in case the smart lock was inadvertently left unlocked, thereby providing extra security to the sleepers.

The embodiments described herein may also be communicatively coupled with a secondary computing devices (e.g., a bedside unit) which is capable of measuring parameters of the subjects' sleeping environments chosen from ambient temperature, ambient relative humidity, ambient air quality, ambient light level, and ambient sound pressure level. In some cases, the sleep monitoring system may integrate the data relative to the sleeper's sleeping environment with the sleep data. The sleep monitoring data may then provide insights to the sleeper regarding the impact the sleeping environment has on the sleep quality of the sleeper or, additionally or alternately, communicate with the home automation networks or smart appliances described above to actuate changes in the sleeper's sleeping environment.

Sleeper Identification System

The sleep monitoring system may also include, or be in communication with, a sleeper identification system. The sleeper identification system may take the sleep data for a sleeper, determine which user account is associated with that sleeper, and associate the sleeper's sleep data with that particular user account. Such a user account may, for example, be a fitness or health tracking account, and may also receive data from one or more other biometric tracking or monitoring devices, such as a wrist-worn fitness tracker.

The sleeper identification system may implement any of a number of techniques in order to determine which user account is associated with a particular sleeper. In some implementations, the sleep monitoring system may be pre-loaded or pre-set with information that links a user account with either the left side of the bed or the right side of the bed. If the extracted sensor data or sleep data for a given sleeper corresponds with a position on the left side of the bed or, if two sleepers are both on the left side of the bed, the left-most sleeper, then the user account associated with the left side of the bed may be associated with that sleeper's sleep data. Conversely, if the extracted sensor data or sleep data for a given sleeper corresponds with a position on the right side of the bed or, if two sleepers are both on the right side of the bed, the right-most sleeper, then the user account associated with the right side of the bed may be associated with that sleeper's sleep data. The above technique, of course, relies on the sleepers to remain on their customary side of the bed or in the same relative left-right positioning. This may nonetheless provide a reasonably reliable way to associate particular sleepers with particular user accounts. However, it may encounter difficulty when only one sleeper is actually in the bed, as it may be difficult for the system to determine which of the two sleepers that are normally present is actually present in that instant.

Another technique that may be used to associate a sleeper with a particular user account is to use one or more aspects of the sleep data or the extracted sensor data to identify a sleeper. For example, if two co-sleepers having significantly different body masses sleep in a bed monitored by a sleep monitoring sensor apparatus having pressure sensors, then they may potentially be distinguished based on the pressure data that is obtained for each sleeper. For example, if one of two sleepers in a bed produces higher-magnitude pressure data, on average, than the other sleeper, then that sleeper may be identified as the heavier of the two sleepers. If the user accounts are each associated with a particular weight or the weight relationship between the two sleepers is somehow specified for the user accounts, then the user account associated with the heavier weight may be used for the sleeper producing the higher-magnitude pressure data, and the user account associated with the lighter weight may be used for the sleeper producing the lower-magnitude pressure data. Thus, at a high level, the user account may be associated with a particular sleeper based on a correlation between pressure data and a physiological characteristic, e.g., weight, a range of weights, pressures, etc., that is associated with the user account. This approach may also be used to track more than two sleepers using the same bed, e.g., each sleeper (two adults and child, for example), may have a different weight and therefore produce different magnitude pressure data. Such different pressure data may be used to identify a matching user account, thereby allowing the sleep data for each such sleeper to be matched up with a corresponding user account. This technique may also be used in many cases to identify a single sleeper, and is also able to accommodate situations in which sleepers may choose to reverse their left-right relative positioning from their customary positioning. In some such implementations, each sleeper that is to be enrolled or associated with a particular sleep monitoring system may be enrolled by having that sleeper lie on the bed in a number of positions without any other person being on the bed. During such an enrollment process, the sleep monitoring system may collect baseline pressure data that provides insight as to the typical pressure values that may be produced by that sleeper; these typical pressure values or the range of pressure values produced during the enrollment process may then be associated with the sleeper's user account (which the sleeper may have specified as part of the enrollment process) and used as a reference against which future pressure measurements may be compared in order to potentially match a sleeper with a user account. This procedure may be repeated for each sleeper that will use that sleep monitoring system.

In some implementations, the user account may also be associated with a wearable fitness tracking or monitoring device, such as a Fitbit™ wearable fitness monitor. Such fitness monitoring devices may have one or more short-range wireless interfaces that may be detectable by a suitable receiver or sensor that may be included in the sleep monitoring system or, for example, in the sleep monitoring sensor apparatus. The sleep monitoring sensor apparatus, for example, may have a pair of Bluetooth or other wireless receivers located on opposing transverse sides of the carrier. When a fitness monitoring device associated with a user account is within wireless range of such receivers, the receivers may be used to detect the proximity of the fitness monitoring device to each receiver, thereby providing an estimate of whether the fitness monitoring device is located closer to the left or right side of the bed. For example, if a wireless receiver located on the left side of the carrier receives a stronger wireless signal from the wearable fitness monitoring device than a wireless receiver on the right side of the bed, the sleep monitoring system may determine that that wearable fitness monitoring device is located closer to the left side of the bed than the right side, and may infer from such information that sleep monitoring data obtained for a sleeper on the left side of the bed (or the leftmost sleeper) should be associated with the user account associated with the detected wearable fitness monitoring system. Such a system may function even if the wearable fitness monitoring system is not worn by the sleeper—for example, many people who wear wearable fitness monitoring systems may take such devices off before going to sleep, but may place them on a nightstand immediately adjacent to the side of the bed that they sleep on. Thus, the wearable fitness monitor may still be in a position that indicates a particular side of the bed, and may still be a reliable indicator of sleeper position in bed.

In another or further implementation, data from a wearable fitness tracker that is actually worn in bed by one of the sleepers may be correlated with sleep data from a sleep monitoring system in order to identify a particular sleeper and allow the sleep data for that sleeper to be associated with that sleeper's user account. For example, a wearable fitness monitor may track motion events over time, as well as heart rate. By correlating motion events that occur in a given interval in the data from a wearable fitness monitor with corresponding motion events that are observed in the same interval in a sleeper's sleep data, a determination may be made that that sleep data should be associated with the user account, and thus the sleeper, that is associated with the wearable fitness monitoring system. Other data correlations may also serve a similar function, e.g., if a sleep monitoring system and a wearable fitness monitor both monitor sleepers' heart rates, then correlations between those heart rates may be used to link the sleep data for that person to the user account associated with that wearable fitness monitoring system.

Once a particular sleeper's sleep data is associated with a particular user account during a sleep session, the sleep data for that sleeper may continue to be associated with that user account for the remainder of the sleep session, even if there are no further determinations of correlations made between the wearable fitness monitoring system data and the sleep data for that sleeper for the duration of the sleep session.

It is to be understood that term "sleeper presence monitoring system" may be used herein to refer to a sleep monitoring system (or a portion thereof) that may be used to monitor for the presence of a person or persons in a bed without necessarily associating that person or persons with a particular user account or accounts. For example, a sleep monitoring system may act as a sleeper presence monitoring system by taking data from a sleep monitoring sensor apparatus and interpreting it to determine if one or more people are in a bed. For example, if the sleep monitoring sensor apparatus includes a sensor mesh of pressure sensors, and the pressure sensor data indicates the likelihood that a person is resting on the bed, then the sleep monitoring system may determine that a person is present on the bed and may thereby function as a sleeper presence monitoring system. In a related instance, a sleeper identification system or engine may also function as a sleeper presence monitoring system, i.e., in identifying a particular sleeper on a mattress, since the sleeper identification system or engine may also, inherently, determine that there is a person on the mattress.

Overall System

It is to be understood that the sleep monitoring sensor apparatus, the sleep monitoring system, the sleeper presence monitoring system, the sleeper identification system, and/or the wake-up alarm system may be selectively combined, as desired, to arrive at multiple different configurations. For example, some implementations may feature only a sleep monitoring system and a sleep monitoring sensor apparatus (without the ability to link sleep data for each sleeper back to a specific account), whereas other implementations may feature a sleep monitoring system, a sleep monitoring sensor apparatus, and a sleeper identification system. The functionalities of the sleep monitoring system and the sleeper identification system, for example, may be provided by different aspects of software running on a common set of one or more processors.

It is also to be understood that many of the functions and techniques discussed herein may be performed by a controller or logic device that includes one or more processors and at least one memory that stores computer-executable instructions for controlling the one or more processors to perform such techniques or provide such functionality. Such a controller or logic device, which may also be referred to herein simply as "logic," may be included in a single system or device, or may include components that are distributed among multiple different devices or locations. For example, a sleep monitoring sensor apparatus may include one or more processors and a memory with computer-executable instructions for controlling the one or more processors to pre-process the data streams that are obtained from the sensors distributed in the sensor mesh of the sleep monitoring sensor apparatus before sending those data streams to the sleep monitoring system as global sensor data. Similarly, the sleep monitoring system may have one or more local processors and a memory storing computer-executable instructions for controlling those one or more local processors to perform sensor data extraction on the global sensor data. In some implementations, the sleep monitoring system may be integrated into the sleep monitoring sensor apparatus, e.g., the controller or logic for the sleep monitoring system may be provided by circuits disposed on or within the carrier. In some implementations, at least some of the functionality discussed herein may be implemented in a remote server, e.g., by a network server reached via the internet or by a smartphone or tablet computing device that is separate from the sleep monitoring sensor apparatus. In some such instances, the remote server may receive the global data from the sleep monitoring sensor apparatus and perform one or more of the techniques described herein, thereby acting as the sleep monitoring system and/or the sleeper identification system.

Figure 53:
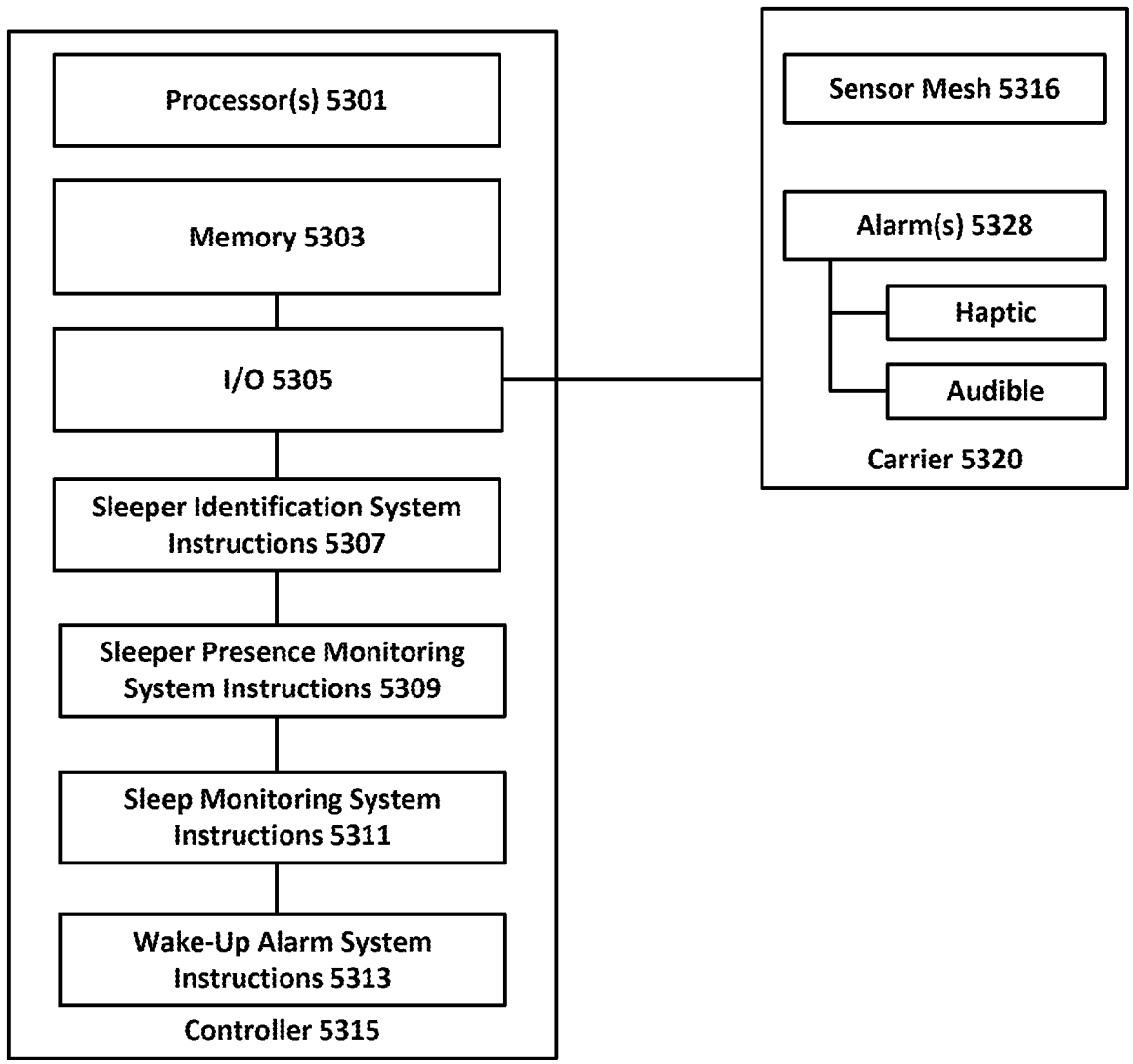
FIG. 53 depicts on example implementation of a sleep monitoring system that has sleep monitoring, sleeper presence monitoring, and sleeper identification functionality, as well as wake-up alarm functionality.

FIG. 53 depicts on example implementation of a sleep monitoring system that has sleep monitoring, sleeper presence monitoring, and sleeper identification functionality, as well as wake-up alarm functionality.

In FIG. 53, a controller 5315 is depicted that includes one or more processors 5301, a memory 5303, and input/output 5305, which may be used to communicate with a sleep monitoring sensor apparatus, such as that provided on carrier 5320. The carrier 5320 may include a sensor mesh 5316, which may include a plurality of sensors that are distributed across the carrier 5320. The carrier 5320, in this example, also includes alarms 5328, which, in this implementation, may include both audible and haptic components.

The controller 5315 may also include sets of stored computer-executable instructions (for example, stored on the memory 5303) that allow the controller 5315 to provide an assortment of functionalities. For example, the memory 5303 may store computer-executable instructions for controlling the one or more processors 5301 to provide sleep monitoring system functionality (5311), sleeper presence monitoring system functionality (5309), sleeper identification system functionality (5307), and/or wake-up alarm functionality (5313).

It is to be appreciated that the techniques described herein may be implemented as computer-executed methods, as computer-readable storage devices that store computer-executable instructions for performing such methods, or as systems or devices configured to perform such methods or provide the functionality discussed herein.

Although several implementations of the concepts disclosed herein have been described in detail herein with reference to the accompanying drawings, it is to be understood that this disclosure is not limited to these precise embodiments, and that various changes and modifications may be effected therein by one skilled in the art without departing from the scope or spirit of the disclosure as defined in the appended claims. Examples of such embodiments are described in the numbered list of embodiments provided below, although it is to be understood that this list is not an exclusive list of embodiments and that the various embodiments listed below may be combined or separated and/or recombined to provide additional embodiments. For example, any of the sleep data collection systems listed below (or described above) may be used with the embodiments directed at alarm functionality and/or sleep data collection.

Embodiment 1

A sleep monitoring system including: one or more carriers configured to be placed above or under a bed mattress and under or over one or more people lying on the bed mattress; one or more first sensors distributed across at least one of the one or more carriers, the one or more first sensors being of a first type of sensor; one or more second sensors distributed across at least one of the one or more carriers, the one or more second sensors being of a second type of sensor different from the first type of sensor; one or more processors; and one or more computer readable storage devices that include computer executable instructions that, when executed by the one or more processors, cause the one or more processors to: obtain global sensor data from the one or more first sensors and the one or more second sensors, and generate sleep data for a sleeper from the global sensor data, the sleep data including data regarding one or more physiological metrics of the sleeper.

Embodiment 2

The sleep monitoring system of embodiment 1, in which the carrier has a dimension of at least 12 inches in a first direction.

Embodiment 3

The sleep monitoring system of embodiment 1, in which the carrier is associated with one or more standard mattress sizes and has a dimension of at least 80% of the width of the mattress size of the one or more standard mattress sizes with the smallest width.

Embodiment 4

The sleep monitoring system of embodiment 1, in which the carrier is a twin-size mattress pad, a full-size mattress pad, a queen-size mattress pad, a king-size mattress pad, a California king-size mattress pad, a twin-size sheet, a full-size sheet, a queen-size sheet, a king-size sheet, a California king-size sheet, a twin-size duvet cover, a full-size duvet cover, a queen-size duvet cover, a king-size duvet cover, a California king-size duvet cover, a twin-sized blanket, a full-size blanket, a queen-size blanket, a king-size blanket, or a California king-size blanket.

Embodiment 5

The sleep monitoring system of embodiment 1, in which the carrier is a mattress pad configured to fit a mattress between 32 and 100 inches in width and 50 to 100 inches in length, a sheet configured to fit a mattress between 32 and 100 inches in width and 50 to 100 inches in length, a blanket configured to fit a mattress between 32 and 100 inches in width and 50 to 100 inches in length, or a duvet cover configured to fit a mattress between 32 and 100 inches in width and 50 to 100 inches in length.

Embodiment 6

The sleep monitoring system of embodiment 1, in which at least one of the one or more first sensors is positioned in a stacked arrangement with at least one of the one or more second sensors such that the at least one of the one or more first sensors overlaps with the at least one of the one or more second sensors when viewed from a direction nominally perpendicular to a major surface of the one or more carriers.

Embodiment 7

The sleep monitoring system of embodiment 6, in which the one or more first sensors are load cells, capacitive force sensors, piezo-electric pressure sensors, or piezo-resistive pressure sensors.

Embodiment 8

The sleep monitoring system of embodiment 1, in which the one or more first sensors are pressure sensors sensitive to absolute pressure or pressure sensors that are only sensitive to changes in pressure.

Embodiment 9

The sleep monitoring system of embodiment 1, in which the one or more first sensors are motion sensors.

Embodiment 10

The sleep monitoring system of embodiment 1, in which the one or more first sensors are temperature sensors.

Embodiment 11

The sleep monitoring system of embodiment 1, in which: the one or more first sensors are spatially separated from one another on the carrier, the one or more second sensors are spatially separated from one another on the carrier, and the one or more first sensors are pressure sensors and the one or more second sensors are accelerometers.

Embodiment 12

The sleep monitoring system of embodiment 1, in which the one or more first sensors includes a plurality of first sensors, the one or more second sensors includes a plurality of second sensors, and the one or more computer readable storage devices further include computer executable instructions that, when executed by the one or more processors, further cause the one or more processors to: analyze data in the global sensor data derived from the one or more first sensors to identify a first location of a first person and a second location of a second person, extract first extracted sensor data from one or more of the second sensors that are proximate to the first location, extract second extracted sensor data from one or more of the second sensors that are proximate to the second location, determine first sleep data for the first person from the first extracted sensor data, and determine second sleep data for the second person from the second extracted sensor data.

Embodiment 13

The sleep monitoring system of embodiment 12, in which the plurality of first sensors are pressure sensors and the one or more computer readable storage devices further include computer executable instructions that, when executed by the one or more processors, further cause the one or more processors to identify the first location of the first person and the second location of a second person by analyzing the data from the first sensors to identify a first center of pressure and a second center of pressure, the first center of pressure associated with the first person and the second center of pressure associated with the second person.

Embodiment 14

A sleep monitoring system including: one or more processors; and a computer readable storage device that includes computer executable instructions that, when executed by the one or more processors, cause the one or more processors to: obtain global sensor data from a plurality of first sensors that are spatially distributed across a bed, analyze the global sensor data and extract first extracted sensor data regarding a first person from the global sensor data and second extracted sensor data regarding a second person from the global sensor data, identify a first component in the global sensor data caused by motions of the first person, and reduce a contribution of the first component to the second extracted sensor data.

Embodiment 15

The sleep monitoring system of embodiment 14, in which the computer readable storage device further includes computer executable instructions that, when executed by the one or more processors, cause the one or more processors to extract the first extracted sensor data regarding the first person and the second extracted sensor data regarding the second person from the global sensor data, identify the first component in the global sensor data caused by motions of the first person, and reduce the contribution of the first component to the second extracted sensor data, at least in part, by performing an independent component analysis (ICA) on the global sensor data.

Embodiment 16

The sleep monitoring system of embodiment 14, in which the computer readable storage device further includes computer executable instructions that, when executed by the one or more processors, cause the one or more processors to determine, from the global sensor data and prior to analyzing the global sensor data and extracting the first extracted sensor data and the second extracted sensors data, that the global sensor data includes motion data attributable to the movements of two or more people.

Embodiment 17

The sleep monitoring system of embodiment 14, in which the computer readable storage device further includes computer executable instructions that, when executed by the one or more processors, further cause the one or more processors to determine sleep data for the second person based, at least in part, on the second extracted sensor data, where the sleep data includes one or more datasets representing sleep-related metrics for a sleep session such as: total sleep time during the sleep session, time in bed, total wake time while in bed, wake events after sleep onset, sleep onset latency, exits from bed during the sleep session, time spent in light sleep during the sleep session, time spent in deep sleep during the sleep session, time spent in REM sleep during the sleep session, degree of restlessness during the sleep session, respiration rate during the sleep session, average heart rate during the sleep session, resting heart rate during the sleep session, heart rate variability during the sleep session, or combinations thereof.

Embodiment 18

The sleep monitoring system of embodiment 14, in which the computer readable storage device further includes computer executable instructions that, when executed by the one or more processors, further cause the one or more processors to: determine first sleep data for the first person using the first extracted sensor data, and determine second sleep data for the second person using the second extracted sensor data.

Embodiment 19

The sleep monitoring system of embodiment 14, in which the first component is included in the first extracted sensor data and the computer readable storage device further includes computer executable instructions that, when executed by the one or more processors, further cause the one or more processors to: determine that a second component of the second extracted sensor data is correlated with, and has a lower amplitude than, the first component of the first extracted sensor data during a first time period; and modify the second component of the second extracted sensor data based on the determination that the first component of the first extracted sensor data is correlated with, and has a lower amplitude than, the second component of the second extracted sensor data during the first time period.

Embodiment 20

The sleep monitoring system of embodiment 19, in which the second extracted sensor data during the first time period is modified by replacing at least some of the second extracted sensor data in the first time period with data that is interpolated from the second extracted sensor data.

Embodiment 21

The sleep monitoring system of embodiment 14, in which the computer readable storage device further stores computer executable instructions that, when executed by the one or more processors, further cause the one or more processors to determine breathing rate data for the second person from the second extracted sensor data.

Embodiment 22

The sleep monitoring system of embodiment 21, in which the first sensors are pressure sensors that are spatially distributed across a carrier and the computer readable storage device further includes computer executable instructions that, when executed by the one or more processors, further cause the one or more processors to: analyze the global sensor data to determine a pressure distribution across the carrier using sensor data streams from the first sensors, analyze the pressure distribution to identify a first center of pressure and a second center of pressure, extract the first extracted sensor data, at least in part, from one or more of the second sensors that are proximate to the first center of pressure, and extract the second extracted sensor data, at least in part, from one or more of the second sensors that are proximate to the second center of pressure.

Embodiment 23

The sleep monitoring system of embodiment 14, in which the computer readable storage device further stores computer executable instructions that, when executed by the one or more processors, further cause the one or more processors to determine heart rate data for the second person from the second extracted sensor data.

Embodiment 24

The sleep monitoring system of embodiment 23, in which the computer readable storage device further includes computer executable instructions that, when executed by the one or more processors, further cause the one or more processors to: determine first gross body movement data for the first person from the first extracted sensor data, and determine second gross body movement data for the second person from the second extracted sensor data.

Embodiment 25

The sleep monitoring system of embodiment 23, in which the computer readable storage device further includes computer executable instructions that, when executed by the one or more processors, further cause the one or more processors to: extract further first extracted sensor data from one or more of the first sensors that are proximate to the first center of pressure, extract further second extracted sensor data from one or more of the first sensors that are proximate to the second center of pressure, determine first breathing rate data for the first person from the first extracted sensor data derived from the one or more first sensors that are proximate to the first center of pressure, and determine second breathing rate data for the second person from the second extracted sensor data derived from the one or more first sensors that are proximate to the second center of pressure.

Embodiment 26

The sleep monitoring system of embodiment 14, in which the computer readable storage device further includes computer readable instructions that, when executed by the one or more processors, further cause the one or more processors to determine, for the second person and for a plurality of first time periods, what sleep stage the second person was in during each time period based on the second extracted sensor data.

Embodiment 27

The sleep monitoring system of embodiment 26, in which the sleep stage that is determined for each first time period for the second person is the predominant sleep stage for that first time period for the second person.

Embodiment 28

The sleep monitoring system of embodiment 26, in which the sleep stage that is determined for each first time period is an awake stage, a light sleep stage, a deep sleep stage, or a random-eye-movement (REM) stage.

Embodiment 29

The sleep monitoring system of embodiment 26, in which the first time periods are each less than 10 minutes in length.

Embodiment 30

The sleep monitoring system of embodiment 26, in which the computer readable storage device further includes instructions that, when executed by the one or more processors, further cause the one or more processors to: determine, from the second extracted sensor data and for each first time period, one or more parameters such as average respiration rate during that first time period, variation of respiration rate during that first time period, movement during that first time period, an indication of time since a most recent previous movement exceeding a first threshold magnitude, an indication of time until a next movement exceeding a second threshold magnitude, or correlation of breath-to-breath signals, and assign, based on at least some of the one or more parameters, a sleep stage to each first time period.

Embodiment 31

A sleeper identification system including: one or more processors and a computer readable storage device that includes computer executable instructions that, when executed by the one or more processors, cause the one or more processors to: obtain first sleep data for a first person from a sleep monitoring system, in which the first sleep data is based, at least in part, on first extracted sensor data collected from a sleep monitoring sensor apparatus, determine that the first person is associated with a first user account based, at least in part, on the first sleep data or the first extracted sensor data, and associate the first sleep data with the first user account.

Embodiment 32

The sleeper identification system of embodiment 31, in which the first sleep data includes data indicating a relative position of the first person relative to a second person in a bed and the computer readable storage device further includes instructions that, when executed by the one or more processors, further cause the one or more processors to determine that the first person is associated with the first user account based on the relative position of the first person relative to the second person in the bed.

Embodiment 33

The sleeper identification system of embodiment 31, in which the first sleep data includes pressure data from one or more pressure sensors and the computer readable storage device further includes instructions that, when executed by the one or more processors, further cause the one or more processors to: obtain information that indicates that one or more user accounts have been previously associated with one or both of the sleep monitoring system and the sleep monitoring apparatus and identify the first user account from the one or more user accounts based on a correlation between the pressure data in the first sleep data and a physiological characteristic associated with the first user account.

Embodiment 34

The sleeper identification system of embodiment 31, in which the first user account is associated with a first wearable fitness tracker and the computer readable storage device further includes instructions that, when executed by the one or more processors, further cause the one or more processors to: analyze first tracker data from the first wearable fitness tracker for a first time period; compare the first tracker data for the first time period against the first sleep data for the first time period; determine that there is a correlation between the first tracker data for the first time period and the first sleep data for the first time period; and associate the first sleep data with the first user account based, at least in part, on the correlation between the first tracker data for the first time period and the first sleep data for the first time period.

Embodiment 35

The sleeper identification system of embodiment 34, in which the computer readable storage device further includes instructions that, when executed by the one or more processors, further cause the one or more processors to associate the first sleep data with the first user account for one or more second time periods different from the first time period based on the correlation between the first tracker data for the first time period and the first sleep data for the first time period and without determining that there is a correlation between first tracker data for the one or more second time periods and the first sleep data for the one or more second time periods.

Embodiment 36

The sleeper identification system of embodiment 34, in which: the first tracker data for the first time period includes motion data; the first sleep data for the first time period includes motion data; and the correlation determination is based on a correlation between the motion data in the first tracker data and the motion data in the first sleep data.

Embodiment 37

The sleeper identification system of any one of embodiments 31 through 36, in which the sleeper identification system is the sleep monitoring system of any one of embodiments 14 through 30.

Embodiment 38

The sleeper identification system of any one of embodiments 31 through 36, in which the sleeper identification system is a device that is separate from the sleep monitoring system.

Embodiment 39

The sleeper identification system of any one of embodiments 31 through 36, in which the sleep monitoring system is included in the sleeper identification system.

Embodiment 40

The sleeper identification system of embodiment 39, in which the one or more computer readable storage devices and the one or more processors of the sleep monitoring system and the one or more computer readable storage devices and the one or more processors of the sleeper identification system are the same.

Embodiment 41

A wake-up alarm system including: one or more carriers configured to be placed above or under a bed mattress having a thickness along a first axis, a width along a second axis, and a length along a third axis, in which the thickness is less than the width and the width is less than the length and the first axis, the second axis, and the third axis are all perpendicular to one another; a first alarm; a second alarm; one or more processors; and a memory, where: the first alarm and the second alarm are located in positions on the one or more carriers that are spaced apart along an axis parallel to the second axis by at least 40% of the width when the one or more carriers are placed above or under the bed mattress in an in-use configuration, the one or more processors is communicatively connected with the memory, the first alarm, and the second alarm, and the memory stores instructions that, when executed by the one or more processors, cause the one or more processors to: activate the first alarm responsive to a first signal, and activate the second alarm responsive to a second signal, where the first signal and the second signal are independent signals.

Embodiment 42

The wake-up alarm system of embodiment 41, in which the first alarm and the second alarm each include one or more devices such as an eccentric rotating mass (ERM), a linear resonant actuator (LRA), a haptic feedback device, a piezoelectric speaker, a speaker, or combinations thereof.

Embodiment 43

The wake-up alarm system of embodiment 41, in which the first alarm and the second alarm each include one or more devices such as an eccentric rotating mass (ERM), a linear resonant actuator (LRA), a haptic feedback device, or combinations thereof.

Embodiment 44

The wake-up alarm system of embodiment 41, in which the one or more carriers includes a first carrier that has a width along the second axis, when placed above or under the bed mattress in an in-use configuration, that is larger than 36 inches, and the first alarm and the second alarm are spaced apart on the first carrier by at least 36 inches along the second axis.

Embodiment 45

The wake-up alarm system of embodiment 44, in which the first carrier, when placed above or under the bed mattress in an in-use configuration, has: a first region located within an outer 25% of the width of the bed mattress and a second region located within an opposing outer 25% of the width of the bed mattress, where the first alarm is located within the first region and the second alarm is located within the second region.

Embodiment 46

The wake-up alarm system of embodiment 45, in which the first carrier has, when placed above or under the bed mattress in an in-use configuration, a third region located within the middle 50% of the width of bed mattress, and the first carrier is stiffer within at least a portion of the third region than in at least some other portions of the first carrier, thereby causing vibrations generated by the first alarm or the second alarm, when activated, to be transmitted from the first alarm or the second alarm, respectively, towards the third region.

Embodiment 47

The wake-up alarm system of embodiment 41, in which the one or more processors are further communicatively coupled with a sleeper presence monitoring system, and the memory further stores instructions for controlling the one or more processors to: determine that a first wake time associated with the first alarm has been met; obtain information from the sleeper presence monitoring system indicating whether or not a first person is located, within a first time period associated with the first wake time, on a first side of the mattress associated with the first alarm; and generate the first signal, at least in part, responsive to determining that the first wake time was met and the information from the sleeper presence monitoring system indicating that the first person was located, within the first time period associated with the first wake time, on the first side of the mattress.

Embodiment 48

The wake-up alarm system of embodiment 47, in which the first wake time is pre-associated with the first side of the mattress.

Embodiment 49

The wake-up alarm system of embodiment 47, in which the first time period is a zero-length time period that is substantially contemporaneous with the first wake time.

Embodiment 50

The wake-up alarm system of embodiment 47, in which the one or more processors are further communicatively coupled with a first input device, and the memory further stores instructions for controlling the one or more processors to: receive a first snooze signal from the first input device after the first signal is generated and before the one or more processors cause the first alarm to deactivate; cause the first alarm to deactivate responsive to receiving the first snooze signal; determine when a first snooze time interval associated with the first snooze signal has elapsed; obtain further information from the sleeper presence monitoring system indicating whether or not the first person is located, within a first snooze time period associated with the first snooze time interval, on the first side of the mattress; and cause the first alarm to reactivate responsive to the determination that the first snooze time interval has elapsed and the further information from the sleeper presence monitoring system indicating that the first person is located, within the first snooze time period associated with the first snooze time interval, on the first side of the mattress.

Embodiment 51

The wake-up alarm system of embodiment 50, in which the first signal is generated until the first alarm is caused to deactivate and the instructions for controlling the one or more processors to cause the first alarm to deactivate cause the first signal to cease being generated.

Embodiment 52

The wake-up alarm system of embodiment 50, in which the instructions for controlling the one or more processors to cause the first alarm to deactivate cause a first alarm stop signal to be generated.

Embodiment 53

The wake-up alarm system of embodiment 50, in which the memory further stores instructions for controlling the one or more processors to cause the first alarm to not reactivate responsive to the determination that the first snooze time interval has elapsed and the further information from the sleeper presence monitoring system indicating that the first person is not located, within the first snooze time period associated with the first snooze time interval, on the first side of the mattress.

Embodiment 54

The wake-up alarm system of embodiment 47, in which the memory further stores instructions for controlling the one or more processors to not generate the first signal responsive to the information from the sleeper presence monitoring system indicating that no person was located, within the first time period associated with the first wake time, on the first side of the mattress.

Embodiment 55

The wake-up alarm system of embodiment 54, in which the memory further stores instructions for controlling the one or more processors to: determine that a second wake time associated with the second alarm has been met; obtain information from the sleeper presence monitoring system indicating whether a second person is located, within a second time period associated with the second wake time, on a second side of the mattress associated with the second alarm; generate the second signal, at least in part, responsive to determining that the second wake time was met and the information from the sleeper presence monitoring system indicating that the second person was located, within the second time period associated with the second wake time, on the second side of the mattress; and not generate the second signal responsive to the information from the sleeper presence monitoring system indicating that no person was located, within the second time period associated with the second wake time, on the second side of the mattress.

Embodiment 56

The wake-up alarm system of embodiment 47, in which the memory further stores instructions for controlling the one or more processors to: determine that a second wake time associated with the second alarm has been met; obtain information from the sleeper presence monitoring system indicating whether a second person is located, within a second time period associated with the second wake time, on a second side of the mattress associated with the second alarm; and generate the second signal, at least in part, responsive to determining that the second wake time was met and the information from the sleeper presence monitoring system indicating that the second person was located, within the second time period associated with the second wake time, on the second side of the mattress.

Embodiment 57

The wake-up alarm system of embodiment 41, in which the one or more processors are further communicatively coupled with a sleeper identification engine, and the memory further stores instructions for controlling the one or more processors to: obtain information from the sleeper identification engine identifying a first person located on a side of the bed mattress associated with the first alarm, determine a first wake time associated with the first person, determine that the first wake time has been met, and generate the first signal, at least in part, responsive to determining that the first wake time was met.

Embodiment 58

The wake-up alarm system of embodiment 57, in which the memory further stores instructions for controlling the one or more processors to: obtain further information from the sleeper identification engine indicating that the first person is still located on the side of the bed mattress associated with the first alarm within a first time period associated with the first wake time and generate the first signal, at least in part, responsive to determining that the first wake time was met and the further information from the sleeper identification engine indicating that the first person was located on the side of the bed mattress associated with the first alarm within the first time period.

Embodiment 59

The wake-up alarm system of embodiment 58, in which the first time period is a zero-length time period that is substantially contemporaneous with the first wake time.

Embodiment 60

The wake-up alarm system of embodiment 57, in which the memory further stores instructions for controlling the one or more processors to: obtain information from the sleeper identification engine identifying a second person located on a side of the bed mattress associated with the first alarm, determine a second wake time associated with the second person, determine that the second wake time has been met, and generate the first signal, at least in part, responsive to determining that the second wake time was met.

Embodiment 61

The wake-up alarm system of embodiment 41, in which the one or more processors are further communicatively coupled with a sleeper identification engine, and the memory further stores instructions for controlling the one or more processors to: obtain information from the sleeper identification engine indicating that a dog or a cat is located on the bed mattress, and generate the first signal, at least in part, responsive to obtaining the information from the sleeper identification engine indicating that the dog or the cat is located on the bed mattress.

Embodiment 62

The wake-up alarm system of embodiment 61, in which the memory further stores instructions for controlling the one or more processors to determine that one or both of a first person and a second person are not on the bed mattress with the dog or the cat prior to generating the first signal.

Embodiment 63

The wake-up alarm system of embodiment 41, in which the one or more processors are further communicatively coupled with a sleep monitoring system configured to identify sleep states for a first person, and the memory further stores instructions for controlling the one or more processors to: obtain information from the sleep monitoring system regarding a sleep state of the first person located on the bed mattress at a second time after generating the first signal, determine that the sleep state of the first person at the second time is an awake sleep state, and generate a second signal responsive to determining that the sleep state of the first person at the second time is an awake sleep state, where the second signal is a signal that causes the first alarm to deactivate.

Embodiment 64

The wake-up alarm system of embodiment 41, in which the one or more processors are further communicatively coupled with a sleep monitoring system configured to identify sleep states for a first person located on the bed mattress, and the memory further stores instructions for controlling the one or more processors to: determine a first wake time associated with the first person, determine that the first wake time has been met, obtain information from the sleep monitoring system regarding a sleep state of the first person located on the bed mattress at a first time prior to the first wake time, determine that the sleep state of the first person at the first time is in a first proper subset of potential sleep states measurable by the sleep monitoring system, and generate, responsive to determining that the first wake time was met and to determining that the sleep state of the first person at the first time is in the first proper subset of potential sleep states measurable by the sleep monitoring system, the first signal at a second time, where the second time is later than the first wake time.

Embodiment 65

The wake-up alarm system of embodiment 64, in which the memory further stores instructions for controlling the one or more processors to: obtain information from the sleep monitoring system regarding the sleep state of the first person at a third time that is after the first time and before the second time, determine that the sleep state of the first person at the third time is in a second proper subset of potential sleep states measurable by the sleep monitoring system, and generate the first signal, at least in part, at the second time responsive to determining that the first wake time was met and that the sleep state of the first person at the third time was in the second proper subset of potential sleep states measurable by the sleep monitoring system.

Embodiment 66

The wake-up alarm system of embodiment 64, in which: the second time is offset from the first wake time by a predetermined time interval, and the memory further stores instructions for controlling the one or more processors to: obtain information from the sleep monitoring system regarding the sleep state of the first person over the predetermined time interval; determine that the sleep state of the first person, over the predetermined time interval, remains within the first proper subset of potential sleep states measurable by the sleep monitoring system; and generate the first signal, at least in part, at the second time in response to the sleep state of the first person over the predetermined time interval remaining within the first proper subset of potential sleep states measurable by the sleep monitoring system.

Embodiment 67

The wake-up alarm system of embodiment 66, in which the predetermined time interval is a user-specified time interval.

Embodiment 68

The wake-up alarm system of embodiment 67, in which the predetermined time interval is 10 minutes, 15 minutes, 20 minutes, or 30 minutes.

Embodiment 69

The wake-up alarm system of embodiment 41, in which the one or more processors are further communicatively coupled with a sleep monitoring system configured to identify sleep states for a first person located on the bed mattress, and the memory further stores instructions for controlling the one or more processors to: determine a first wake time associated with the first person; determine that the first wake time has been met; obtain information from the sleep monitoring system regarding one or more sleep states of the first person starting at a first time prior to generating the first signal, where the sleep states identifiable by the sleep monitoring system include a first proper subset of potential sleep states measurable by the sleep monitoring system and a second proper subset of potential sleep states measurable by the sleep monitoring system, where the first proper subset and the second proper subset are different; a) generate the first signal responsive to the first wake time being met and the information from the sleep monitoring system indicating that the first person is in a sleep state in the second proper subset when the first wake time is met; b) generate the first signal responsive to the first wake time being met and the information from the sleep monitoring system indicating that the first person has transitioned, after the first wake time, from a sleep state in the first proper subset to a sleep state in the second proper subset; and c) generate the first signal responsive to a second time being met and the information from the sleep monitoring system indicating that the first person remained in one or more sleep states in the first proper subset during a first predetermined time interval and did not enter into a sleep state in the second proper subset during the first predetermined time interval.

Embodiment 70

The wake-up alarm system of embodiment 69, in which: the first signal in (c) causes the first alarm to activate with a first intensity, the first signal in (a), (b), or (a) and (b) causes the first alarm to activate with a second intensity, and the first intensity is greater than the second intensity.

Embodiment 71

The wake-up alarm system of embodiment 70, in which: the first alarm includes a haptic element and a sound-emitting element, the sound-emitting element is activated when the first alarm is activated at the first intensity and is not activated when the first alarm is activated at the second intensity, and the haptic element is activated when the first alarm is activated at the second intensity.

Embodiment 72

The wake-up alarm system of embodiment 71, in which the haptic element is also activated when the first alarm is activated at the first intensity.

Embodiment 73

The wake-up alarm system of embodiment 69, in which: the first proper subset includes a Random Eye Movement (REM) sleep state and a deep sleep state, and the second proper subset includes an awake sleep state and a light sleep state.

Embodiment 74

The wake-up alarm system of embodiment 73, in which the predetermined time interval is a user-specified time interval.

Embodiment 75

The wake-up alarm system of embodiment 74, in which the predetermined time interval is 10 minutes, 15 minutes, 20 minutes, or 30 minutes.

Embodiment 76

The wake-up alarm system of embodiment 41, in which the one or more processors are further communicatively coupled with a sleep monitoring system configured to identify sleep states for a first person, and the memory further stores instructions for controlling the one or more processors to: determine a first wake time associated with the first person; determine that the first wake time has been met; obtain information from the sleep monitoring system regarding a sleep state of the first person at a first time prior to generating the first signal, where the sleep states identifiable by the sleep monitoring system include a first proper subset of potential sleep states measurable by the sleep monitoring system and a second proper subset of potential sleep states measurable by the sleep monitoring system, and where the first proper subset and the second proper subset are different; cause, responsive to determining that the first wake time was met and to determining that the sleep state of the first person at the first time is in the first proper subset of potential sleep states measurable by the sleep monitoring system, the first signal to be generated such that the first alarm is activated at a first intensity; and cause, responsive to determining that the first wake time was met and to determining that the sleep state of the first person at the first time is in the second proper subset of potential sleep states measurable by the sleep monitoring system, the first signal to be generated such that the first alarm is activated at a second intensity, where the first intensity is greater than the second intensity.

Embodiment 77

The wake-up alarm system of embodiment 41, in which the one or more processors are further communicatively coupled with a sleep monitoring system configured to characterize sleep behavior for a first person and a second person, and the memory further stores instructions for controlling the one or more processors to: determine that the first person is restless during a first time interval; determine that a sleep state of the second person is degraded during the first time interval due to the restlessness of the first person; and generate the first signal responsive to determining that the sleep state of the second person is degraded during the first time interval due to the restlessness of the first person, where the first person is located closer to the first alarm than the second person and the second person is located closer to the second alarm than the first person.

Embodiment 78

The wake-up alarm system of embodiment 41, in which the one or more processors are further communicatively coupled with a sleep monitoring system at least including one or more microphones and configured to characterize sleep behavior for a first person and a second person, and the memory further stores instructions for controlling the one or more processors to: determine, using the one or more microphones, that the first person is generating noise above a first threshold during a first time interval; determine that a sleep state of the second person is below a second threshold during the first time interval; and generate the first signal responsive to determining that the sleep state of the second person is below the second threshold during the first time interval and that the first person is generating noise above the first threshold during the first time interval, where the first person is located closer to the first alarm than the second person and the second person is located closer to the second alarm than the first person.

Embodiment 79

The wake-up alarm system of embodiment 41, in which: the first alarm includes one or more devices such as an eccentric rotating mass (ERM), a linear resonant actuator (LRA), or a haptic feedback device; the one or more processors are further communicatively coupled with a sleep monitoring system configured to identify sleep states for a first person located on a side of the bed mattress associated with the first alarm; and the memory further stores instructions for controlling the one or more processors to: generate repeated first signals at a first frequency that is between 0.1 Hz to 0.5 Hz, obtain information from the sleep monitoring system indicating that the first person has transitioned from an awake sleep state to a non-awake sleep state, and stop generating the first signals responsive to obtaining the information from the sleep monitoring system indicating that the first person has transitioned from the awake sleep state to the non-awake sleep state.

Embodiment 80

The wake-up alarm system of embodiment 41, in which the memory further stores instructions for controlling the one or more processors to determine the first frequency based on data indicative of a respiration rate of the first person measured by the sleep monitoring system while the first person is asleep during one or more previous sleep sessions.

Embodiment 81

A sleep monitoring system including: a distributed area sensor of a type such as (a) a pneumatic sensor system and/or (b) an optical fiber sensor system; one or more processors; a computer readable storage device that includes computer executable instructions that, when executed by the one or more processors, cause the one or more processors to: obtain sleep data from the distributed area sensor indicative of movement of a person lying on the distributed area sensor.

Embodiment 82

Any of the above numbered embodiments that reference one or more sensors, but including, in addition to or in place of those one or more sensors, a (a) pneumatic sensor system, (b) an optical fiber sensor system, or (c) a pneumatic sensor system and an optical fiber system.

What is claimed is:

1. A wake-up alarm system comprising:
a plurality of carriers configured to be placed above or under a bed mattress having a thickness along a first axis, a width along a second axis, and a length along a third axis, wherein the thickness is less than the width and the width is less than the length and the first axis, the second axis, and the third axis are all perpendicular to one another;
a first carrier of the plurality of carriers comprising a first alarm;
a second carrier of the plurality of carriers comprising a second alarm;
one or more processors; and
a memory, wherein:
the first alarm and the second alarm are located in positions on the first carrier and the second carrier that are spaced apart along an axis parallel to the second axis by at least 40% of the width when the one or more carriers are placed above or under the bed mattress in an in-use configuration,
the one or more processors is communicatively connected with the memory, the first alarm, and the second alarm, and
the memory stores instructions that, when executed by the one or more processors, cause the one or more processors to:
activate the first alarm responsive to a first signal, and
activate the second alarm responsive to a second signal, wherein the first signal and the second signal are independent signals.

2. The wake-up alarm system of claim 1, wherein the one or more processors are further communicatively coupled with a sleeper presence monitoring system, and the memory further stores instructions for controlling the one or more processors to:
determine that a first wake time associated with the first alarm has been met;
obtain information from the sleeper presence monitoring system indicating whether or not a first person is located, within a first time period associated with the first wake time, on a first side of the mattress associated with the first alarm; and
generate the first signal, at least in part, responsive to determining that the first wake time was met and the information from the sleeper presence monitoring system indicating that the first person was located, within the first time period associated with the first wake time, on the first side of the mattress.

3. The wake-up alarm system of claim 2, wherein the first wake time is pre-associated with the first side of the mattress.

4. The wake-up alarm system of claim 2, wherein the one or more processors are further communicatively coupled with a first input device, and the memory further stores instructions for controlling the one or more processors to:
receive a first snooze signal from the first input device after the first signal is generated and before the one or more processors cause the first alarm to deactivate;
cause the first alarm to deactivate responsive to receiving the first snooze signal;
determine when a first snooze time interval associated with the first snooze signal has elapsed;
obtain further information from the sleeper presence monitoring system indicating whether or not the first person is located, within a first snooze time period associated with the first snooze time interval, on the first side of the mattress; and
cause the first alarm to reactivate responsive to the determination that the first snooze time interval has elapsed and the further information from the sleeper presence monitoring system indicating that the first person is located, within the first snooze time period associated with the first snooze time interval, on the first side of the mattress.

5. The wake-up alarm system of claim 1, wherein the one or more processors are further communicatively coupled with a sleep monitoring system configured to identify sleep states for a first person, and the memory further stores instructions for controlling the one or more processors to:
obtain information from the sleep monitoring system regarding a sleep state of the first person located on the bed mattress at a second time after generating the first signal,
determine that the sleep state of the first person at the second time is an awake sleep state, and
generate the second signal responsive to determining that the sleep state of the first person at the second time is an awake sleep state, wherein the second signal is a signal that causes the first alarm to deactivate.

6. The wake-up alarm system of claim 1, wherein the one or more processors are further communicatively coupled with a sleep monitoring system configured to identify sleep states for a first person located on the bed mattress, and the memory further stores instructions for controlling the one or more processors to:
determine a first wake time associated with the first person,
determine that the first wake time has been met,
obtain information from the sleep monitoring system regarding a sleep state of the first person located on the bed mattress at a first time prior to the first wake time,
determine that the sleep state of the first person at the first time is in a first proper subset of potential sleep states measurable by the sleep monitoring system, and
generate, responsive to determining that the first wake time was met and to determining that the sleep state of the first person at the first time is in the first proper subset of potential sleep states measurable by the sleep monitoring system, the first signal at a second time, wherein the second time is later than the first wake time.

7. The wake-up alarm system of claim 6, wherein the memory further stores instructions for controlling the one or more processors to:
obtain information from the sleep monitoring system regarding the sleep state of the first person at a third time that is after the first time and before the second time,
determine that the sleep state of the first person at the third time is in a second proper subset of potential sleep states measurable by the sleep monitoring system, and
generate the first signal, at least in part, at the second time responsive to determining that the first wake time was met and that the sleep state of the first person at the third time was in the second proper subset of potential sleep states measurable by the sleep monitoring system.

8. The wake-up alarm system of claim 6, wherein:
the second time is offset from the first wake time by a predetermined time interval, and
the memory further stores instructions for controlling the one or more processors to:
obtain information from the sleep monitoring system regarding the sleep state of the first person over the predetermined time interval;
determine that the sleep state of the first person, over the predetermined time interval, remains within the first proper subset of potential sleep states measurable by the sleep monitoring system; and
generate the first signal, at least in part, at the second time in response to the sleep state of the first person over the predetermined time interval remaining within the first proper subset of potential sleep states measurable by the sleep monitoring system.

9. The wake-up alarm system of claim 8, wherein the predetermined time interval is a user-specified time interval.

10. The wake-up alarm system of claim 9, wherein the predetermined time interval is selected from the group consisting of 10 minutes, 15 minutes, 20 minutes, and 30 minutes.

11. The wake-up alarm system of claim 1, wherein the one or more processors are further communicatively coupled with a sleep monitoring system configured to identify sleep states for a first person located on the bed mattress, and the memory further stores instructions for controlling the one or more processors to:
determine a first wake time associated with the first person;
determine that the first wake time has been met;
obtain information from the sleep monitoring system regarding one or more sleep states of the first person starting at a first time prior to generating the first signal, wherein the sleep states identifiable by the sleep monitoring system include a first proper subset of potential sleep states measurable by the sleep monitoring system and a second proper subset of potential sleep states measurable by the sleep monitoring system, wherein the first proper subset and the second proper subset are different;
a) generate the first signal responsive to the first wake time being met and the information from the sleep monitoring system indicating that the first person is in a sleep state in the second proper subset when the first wake time is met;
b) generate the first signal responsive to the first wake time being met and the information from the sleep monitoring system indicating that the first person has transitioned, after the first wake time, from a sleep state in the first proper subset to a sleep state in the second proper subset; and
c) generate the first signal responsive to a second time being met and the information from the sleep monitoring system indicating that the first person remained in one or more sleep states in the first proper subset during a first predetermined time interval and did not enter into a sleep state in the second proper subset during the first predetermined time interval.

12. The wake-up alarm system of claim 11, wherein:
the first signal in (c) causes the first alarm to activate with a first intensity,
the first signal in (a), (b), or (a) and (b) causes the first alarm to activate with a second intensity, and
the first intensity is greater than the second intensity.

13. The wake-up alarm system of claim 12, wherein:
the first alarm includes a haptic element and a sound-emitting element,
the sound-emitting element is activated when the first alarm is activated at the first intensity and is not activated when the first alarm is activated at the second intensity, and
the haptic element is activated when the first alarm is activated at the second intensity.

14. The wake-up alarm system of claim 13, wherein the haptic element is also activated when the first alarm is activated at the first intensity.

15. The wake-up alarm system of claim 11, wherein:
the first proper subset includes a Random Eye Movement (REM) sleep state and a deep sleep state, and
the second proper subset includes an awake sleep state and a light sleep state.

16. The wake-up alarm system of claim 15, wherein the predetermined time interval is a user-specified time interval.

17. The wake-up alarm system of claim 16, wherein the predetermined time interval is selected from the group consisting of 10 minutes, 15 minutes, 20 minutes, and 30 minutes.

18. The wake-up alarm system of claim 1, wherein the one or more processors are further communicatively coupled with a sleep monitoring system configured to identify sleep states for a first person, and the memory further stores instructions for controlling the one or more processors to:
determine a first wake time associated with the first person;
determine that the first wake time has been met;
obtain information from the sleep monitoring system regarding a sleep state of the first person at a first time prior to generating the first signal, wherein the sleep states identifiable by the sleep monitoring system include a first proper subset of potential sleep states measurable by the sleep monitoring system and a second proper subset of potential sleep states measurable by the sleep monitoring system, and wherein the first proper subset and the second proper subset are different;
cause, responsive to determining that the first wake time was met and to determining that the sleep state of the first person at the first time is in the first proper subset of potential sleep states measurable by the sleep monitoring system, the first signal to be generated such that the first alarm is activated at a first intensity; and
cause, responsive to determining that the first wake time was met and to determining that the sleep state of the first person at the first time is in the second proper subset of potential sleep states measurable by the sleep monitoring system, the first signal to be generated such that the first alarm is activated at a second intensity, wherein the first intensity is greater than the second intensity.

19. The wake-up alarm system of claim 1, wherein the one or more processors are further communicatively coupled with a sleep monitoring system configured to characterize sleep behavior for a first person and a second person, and the memory further stores instructions for controlling the one or more processors to:
determine that the first person is restless during a first time interval;
determine that a sleep state of the second person is degraded during the first time interval due to the restlessness of the first person; and
generate the first signal responsive to determining that the sleep state of the second person is degraded during the first time interval due to the restlessness of the first person, wherein the first person is located closer to the first alarm than the second person and the second person is located closer to the second alarm than the first person.

20. The wake-up alarm system of claim 1, wherein the one or more processors are further communicatively coupled with a sleep monitoring system at least including one or more microphones and configured to characterize sleep behavior for a first person and a second person, and the memory further stores instructions for controlling the one or more processors to:
determine, using the one or more microphones, that the first person is generating noise above a first threshold during a first time interval;
determine that a sleep state of the second person is below a second threshold during the first time interval; and
generate the first signal responsive to determining that the sleep state of the second person is below the second threshold during the first time interval and that the first person is generating noise above the first threshold during the first time interval, wherein the first person is located closer to the first alarm than the second person and the second person is located closer to the second alarm than the first person.

* * * * *